(12) United States Patent
Qasba et al.

(10) Patent No.: US 8,703,459 B2
(45) Date of Patent: Apr. 22, 2014

(54) CATALYTIC DOMAINS OF BETA(1,4)-GALACTOSYLTRANSFERASE I HAVING ALTERED METAL ION SPECIFICITY

(75) Inventors: Pradman Qasba, Bethesda, MD (US); Elizabeth Boeggeman, Bethesda, MA (US); Boopathy Ramakrishnan, Frederick, MD (US)

(73) Assignee: The United States of America, as represented by the Secretary, Department of Health & Human Services, Washington, DC (US)

( * ) Notice: Subject to any disclaimer, the term of this patent is extended or adjusted under 35 U.S.C. 154(b) by 1651 days.

(21) Appl. No.: 10/581,942

(22) PCT Filed: Dec. 6, 2004

(86) PCT No.: PCT/US2004/040844
§ 371 (c)(1),
(2), (4) Date: Apr. 23, 2007

(87) PCT Pub. No.: WO2005/056783
PCT Pub. Date: Jun. 23, 2005

(65) Prior Publication Data
US 2008/0199905 A1    Aug. 21, 2008

Related U.S. Application Data

(60) Provisional application No. 60/527,615, filed on Dec. 5, 2003.

(51) Int. Cl.
| | | |
|---|---|---|
| *C12N 9/10* | (2006.01) | |
| *C12N 5/16* | (2006.01) | |
| *C12N 15/00* | (2006.01) | |
| *C12P 21/06* | (2006.01) | |
| *C07H 21/04* | (2006.01) | |

(52) U.S. Cl.
USPC ...... 435/193; 435/68.1; 435/69.1; 435/320.1; 435/325; 536/23.2

(58) Field of Classification Search
None
See application file for complete search history.

(56) References Cited

FOREIGN PATENT DOCUMENTS

WO    WO-2004/063344    7/2004

OTHER PUBLICATIONS

Whisstock et al. Quaterly Reviews of Biophysics, 2003, "Prediction of protein function from protein sequence and structure", 36(3): 307-340.*
Chica et al. Semi-rational approaches to engineering enzyme activity: combining the benefits of directed evolution and rational design, Curr Opin Biotechnol. Aug. 2005;16(4):378-84. Review.*
Witkowski et al. Conversion of a beta-ketoacyl synthase to a malonyl decarboxylase by replacement of the active-site cysteine with glutamine, Biochemistry. Sep. 7, 1999;38(36):11643-50.*
Vadaie et al. Identification and characterization of a *Drosophila melanogaster*, ortholog of human beta1,4-galactosyltransferase VII. Glycobiology. Oct. 2002;12(10):589-97.*
Boeggeman et al., "Mutation Met344His in bovine beta, 4-galactosyltransferase-1 broadens its primary metal ion specificity," *Glycobiology*, vol. 13, No. 11, p. 869 (2003).
Ramakrishnan et al., "Alpha-Lactalbumin (LA) stimulates milk beta-1, 4-galactosyltransferase I (beta4Gal-T1) to transfer glucose from UDP-glucose to N-acetylglucosamine", *Journal of Biological Chemistry*, vol. 276, No. 40, pp. 37665-37671 (2001).
Ramakrishnan and Qasba, "Structure-based design of beta, 4-galactosyltransferase I (beta4Gal-T1) with equally efficient N-acetylgalactosaminyltransferase activity", *Journal of Biological Chemistry*, vol. 277, No. 23, pp. 20833-20839 (2002).
Ramakrishnan et al., "Effect of the Met344His mutation on the conformational dynamics of bovine beta-1,4-galactosyltransferase: crystal structure of the Met344His mutant in complex with chitobiose", *Biochemistry*, vol. 43, No. 39, pp. 12513-12522 (2004).

* cited by examiner

*Primary Examiner* — Iqbal H Chowdhury
(74) *Attorney, Agent, or Firm* — Edwards Wildman Palmer LLP; Peter F. Corless

(57) ABSTRACT

Disclosed are mutants of galactosyltransferases that can catalyze formation of oligosaccharides in the presence of magnesium; mutants of galactosyltransferases having altered donor and acceptor specificity which can catalyze formation of oligosaccharides in the presence of magnesium; methods and compositions that can be used to synthesize oligosaccharides; methods for increasing the immunogenicity of an antigen; and methods to stabilize platelets.

12 Claims, 12 Drawing Sheets

Gal-T1

CATALYTIC DOMAINS OF BETA(1,4)-GALACTOSYLTRANSFERASE I HAVING ALTERED METAL ION SPECIFICITY

REFERENCE TO RELATED APPLICATIONS

This application claims priority under 35 U.S.C. 119(e) from U.S. Provisional Application Ser. No. 60/527,615 filed Dec. 5, 2003, which is incorporated herein by reference.

GOVERNMENT FUNDING

The invention described herein was developed with support from the Department of Health and Human Services grant number N01-C0-12400. The U.S. Government may have certain rights in the invention.

FIELD OF THE INVENTION

The invention relates generally to β(1,4)-galactosyltransferase I mutants having altered metal ion specificity, and methods of use thereof. In addition, the invention relates to methods for using the β(1,4)-galactosyltransferase I mutants to increase the immunogenicity of an antigen, such as a vaccine, for synthesizing saccharide compositions, and for stabilizing platelets.

BACKGROUND OF THE INVENTION

Oligosaccharides are chains composed of saccharide units, which are commonly known as sugars. Of the biological polymer families, oligosaccharides are the least studied, due in part to the difficulty of sequencing and synthesizing their complex sugar chains. Currently, no generally applicable synthetic techniques for synthesizing oligosaccharides are available.

Intensive research efforts have been devoted to carbohydrates and molecules comprising carbohydrate fragments, such as glycolipids and glycoproteins. Research interest in these moieties has been largely due to the recognition that interaction between proteins and carbohydrates are involved in a wide array of biological recognition events, including fertilization, molecular targeting, intracellular recognition, and viral, bacterial, and fungal pathogenesis. It is now widely appreciated that the oligosaccharide portions of glycoproteins and glycolipids mediate cell-cell interactions, cell-ligand interactions, cell-extracellular matrix interactions, and cell-pathogen interactions.

It is thought that many of these interactions can be inhibited by oligosaccharides that have the same sugar sequence and stereochemistry found on the active portion of a glycoprotein or glycolipid involved in the interactions. The oligosaccharides are believed to compete with the glycoproteins and glycolipids for binding sites on the receptor proteins. For example, the disaccharide galactosyl-β(1,4)-N-acetylglucosamine is believed to be one component of the glycoprotein which interacts with receptors in the plasma membrane of liver cells. Thus, oligosaccharides and other saccharide compositions that mimic ligands recognized and bound by cellular receptors are thought to be useful in applications that include diagnostics and therapeutics.

In addition to mediating numerous cellular interactions, many oligosaccharides are recognized by the immune system. For example, Anti-Gal, a naturally occurring antibody present in all humans, specifically interacts with the carbohydrate epitope Gal-α(1-3)Gal-β(1-4)GlcNAc-R (α-galactosyl epitope). This antibody does not interact with any other known carbohydrate epitope produced by mammalian cells (Galili, *Springer Seminar Immunopathology*, 15:153 (1993)). Anti-Gal constitutes approximately 1% of circulating IgG (Galili et al., *J. Exp. Med.*, 160:1519 (1984)) and is also found in the form of IgA and IgM (Davine et al., *Kidney Int.*, 31:1132 (1987); Sandrin et al., *Proc. Natl. Acad. Sci.*, 90:11391 (1993)). It is produced by 1% of circulating B-lymphocytes (Galili et al., *Blood*, 82:2485 (1993)). Accordingly, the ability of carbohydrates to elicit an immune response can be utilized to increase the effectiveness of vaccines against many types of pathogens by linking such a carbohydrate to a vaccine to increase the immune response to the vaccine.

There has been relatively little effort to test oligosaccharides as therapeutic agents for humans or animal diseases however, as methods to synthesize oligosaccharides have been unavailable. Limited types of small oligosaccharides can be custom-synthesized by organic chemical methods, but the cost of such compounds is typically prohibitively high. In addition, it is very difficult to synthesize oligosaccharides stereospecifically and the addition of some sugars, such as sialic acid and fucose, has not been effectively accomplished because of the extreme lability of their bonds. Improved, generally applicable methods for oligosaccharide synthesis are thereby desired or the production of large amounts of widely varying oligosaccharides for therapeutic purposes. Accordingly, the present invention provides enzymes and methods that can be used to promote the chemical linkage of numerous sugars that have previously been difficult to link.

SUMMARY OF THE INVENTION

The invention provides altered β(1,4)-galactosyltransferase I catalytic domains that transfer galactose from a donor, UDP-galactose, to an acceptor, N-acetylglucosamine, to form a galactose-β(1,4)-N-acetylglucosamine bond in the presence of a wide range of metal ions, including but not limited to magnesium (Mg) and Zinc (Zn). This broad metal utilization contrasts with that of the corresponding wild-type enzyme that utilizes manganese. The invention also provides β(1,4)-galactosyltransferase I catalytic domains that catalyze formation of glucose-β(1,4)-N-acetylglucosamine; N-acetylgalactosamine-β(1,4)-N-acetylglucosamine bonds; N-acetylgalactosamine-β(1,4)-glucose bonds; N-acetylglucosamine-β(1,4)-N-acetylglucosamine bonds; mannose-β(1,4)-N-acetylglucosamine bonds; and galactose-β(1,4)-N-acetylglucosamine-6-$SO_3$ bonds in the presence of a wide range of metal ions. The invention also provides polypeptides that contain each of the aforementioned catalytic domains.

The invention provides nucleic acid segments that encode the aforementioned β(1,4)-galactosyltransferase I catalytic domains. Expression cassettes and cells that include nucleic acid segments that encode the aforementioned β(1,4)-galactosyltransferase I catalytic domains are also provided.

Additionally provided are methods to synthesize a galactose-β(1,4)-N-acetylglucosamine moiety; a glucose-β(1,4)-N-acetylglucosamine moiety; an N-acetylgalactosamine-β(1,4)-N-acetylglucosamine moiety, an N-acetylgalactosamine β(1,4)-glucose moiety; an N-acetylglucosamine-β(1,4)-N-acetylglucosamine moiety; a mannose-β(1,4)-N-acetylglucosamine moiety; and a galactose-β(1,4)-N-acetylglucosamine-6-$SO_3$ moiety in the presence of a wide range of metal ions, including but not limited to zinc (Zn) and magnesium (Mg), at such concentrations including from about 0.25, 0.5, 0.75, 1.0, 1.25, 1.5, 1.75, 2.0, 2.25, 2.5, 2.75, 3.0, 3.25, 3.5, 3.75, 4.0, 4.25, 4.5, 4.75, 5.0, 5.25, 5.5, 5.75, 6.0, 7.0, 8.0, 9.0 mM and higher such as about 10, 15, 20 30, 40, 50, 60 70, 80, 90, 100, 150, 200, 300, 400, 500, 600 mM and so on.

The invention also provides methods to increase the immunogenicity of an antigen, and methods to prepare an oligosaccharide composition, including those having a defined sequence.

Further provided by the invention are oligosaccharides produced through use of the catalytic domains and methods disclosed herein.

The invention also provides a method for stabilizing platelets.

DETAILED DESCRIPTION OF THE INVENTION

Figure 1A:
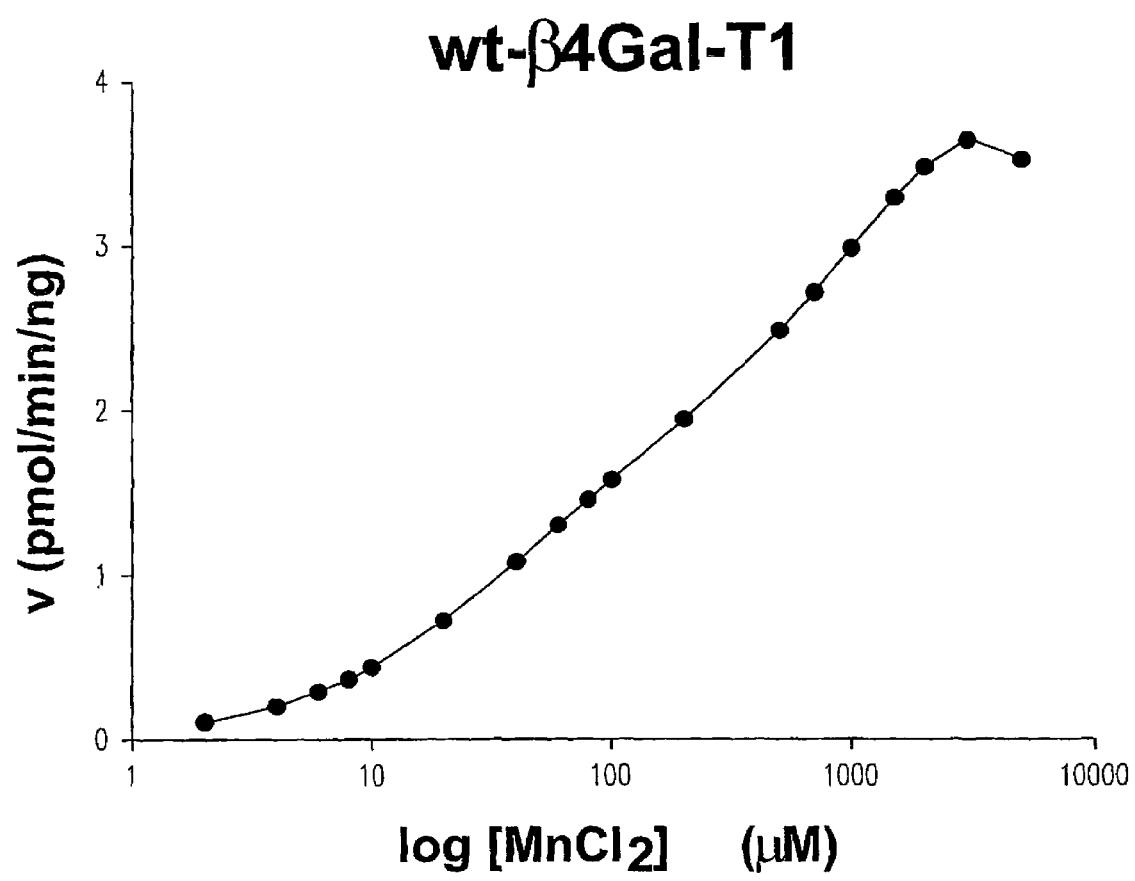
FIG. 1A illustrates a metal ion activation curve of wild-type enzyme in the presence of $Mn^{2+}$ where the metal ion concentration is plotted on a log scale.

β(1,4)-galactosyltransferase I catalyzes the transfer of galactose from the donor, UDP-galactose, to an acceptor, N-acetylglucosamine, to form a galactose-β(1,4)-N-acetylglucosamine bond. This reaction allows galactose to be linked to an N-acetylglucosamine that may itself be linked to a variety of other molecules. Examples of these molecules include other sugars and proteins. The reaction can be used to make many types of molecules having great biological significance. For example, galactose-β(1,4)-N-acetylglucosamine linkages are important for many recognition events that control how cells interact with each other in the body, and how cells interact with pathogens. In addition, numerous other linkages of this type are also very important for cellular recognition and binding events as well as cellular interactions with pathogens, such as viruses. Therefore, methods to synthesize these types of bonds have many applications in research and medicine to develop pharmaceutical agents and improved vaccines that can be used to treat disease.

The present invention is based on the surprising discovery that the metal specificity of a β(1,4)-galactosyltransferase can be altered such that the enzyme can utilize magnesium as a cofactor during the catalytic process instead of manganese. This alteration allows the mutated enzyme to catalyze the transfer of a sugar from a donor to an acceptor through formation of a β(1,4) linkage in the presence of magnesium. Such enzymes are active under physiological conditions where magnesium is present in sufficient concentration to allow the enzyme to function, and where manganese concentrations may not be adequate. Furthermore, such enzymes are useful during in vitro synthesis of β(1,4) linkages where magnesium is preferred over manganese. Such instances may exist when other magnesium utilizing enzymes are used during the synthetic process.

Enzymes having altered metal utilization may be mutated such that they can transfer many different types of donors to many different types of acceptors. Therefore, the mutated β(1,4)-galactosyltransferases of the invention can be used to synthesize a variety of products in the presence of magnesium, that until now, have been very difficult and expensive to produce.

Definitions

Abbreviations: catalytic domain of β(1,4)-Galactosyltransferase I (CDβ4Gal-T1); β(1,4)-Galactosyltransferase I (β4Gal-T1); catalytic domain (CD); wild-type (wt); galactosyltransferase activity (Gal-T); beta-mercaptoethanol (β-ME); N-acetylgalactosamine transferase activity (GalNAc-T); α-Lactalbumin (LA).

The term "acceptor" refers to a molecule or structure onto which a donor is actively linked through action of a catalytic domain of a galactosyltransferase, or mutant thereof. Examples of acceptors include, but are not limited to, carbohydrates, glycoproteins, and glycolipids.

The term "catalytic domain" refers to an amino acid segment which folds into a domain that is able to catalyze the linkage of a donor to an acceptor. For example, a catalytic domain may be from, but is not limited to bovine β(1,4)-Galactosyltransferase I (Seq ID NO: 6), the catalytic domain from human β(1,4)-Galactosyltransferase I (Seq ID NO: 4), or the catalytic domain from mouse β(1,4)-Galactosyltransferase I (Seq ID NO: 5). A catalytic domain may have an amino acid sequence found in a wild-type enzyme, or may have an amino acid sequence that is different from a wild-type sequence. For example, a catalytic domain may have an amino acid sequence that corresponds to amino acid residues 130-402 of SEQ ID NO: 6, expect that the methionine is exchanged with histidine at amino acid position 344.

The term "donor" refers to a molecule that is actively linked to an acceptor molecule through the action of a catalytic domain of a galactosyltransferase, or mutant thereof. A donor molecule can include a sugar or a sugar derivative. Examples of donors include, but are not limited to UDP-galactose, UDP-mannose, UDP-N-acetylglucosamine, UDP-glucose, GDP-mannose, UDP-N-acetylgalactosamine, UDP-glucuronic acid, GDP-Fucose, and CMP-N-acetylneuraminic acid. Donors include sugar derivatives that include active groups, such as cross-linking agents or labeling agents. Accordingly, oligosaccharides may be prepared according to the methods of the invention that include a sugar derivative having a desired characteristic.

"Expression cassette" as used herein means a DNA sequence capable of directing expression of a particular nucleotide sequence in an appropriate host cell, including a promoter operably linked to the nucleotide sequence of interest that is operably linked to termination signals. It also typically includes sequences required for proper translation of the nucleotide sequence. The expression cassette may be one that is naturally occurring but has been obtained in a recombinant form useful for heterologous expression. The expression of the nucleotide sequence in the expression cassette may be under the control of a constitutive promoter or of an inducible promoter that initiates transcription only when the host cell is exposed to some particular external stimulus. In the case of a multicellular organism, the promoter can also be specific to a particular tissue or organ or stage of development.

The term "Magnesium" as used herein refers to divalent magnesium ion ($Mg^{+2}$). Magnesium can be derived from numerous magnesium salts. Examples of magnesium salts include magnesium chloride, magnesium acetate, magnesium nitrate, and the like.

The terms "Oligosaccharide" and "Polysaccharide" are used interchangeably herein. These terms refer to saccharide chains having two or more linked sugars. Oligosaccharides and polysaccharides may be homopolymers and heteropolymers having a random sugar sequence or a preselected sugar sequence. Additionally, oligosaccharides and polysaccharides may contain sugars that are normally found in nature, derivatives of sugars, and mixed polymers thereof.

"Polypeptides" and "Proteins" are used interchangeably herein. Polypeptides and proteins can be expressed in vivo through use of prokaryotic or eukaryotic expression systems. Many such expressions systems are known in the art and are commercially available. (Clontech, Palo Alto, Calif.; Stratagene, La Jolla, Calif.). Examples of such systems include, but are not limited to the T7-expression system in prokaryotes and the bacculovirus expression system in eukaryotes. Polypeptides can also be synthesized in vitro, e.g., by the solid phase peptide synthetic method or by in vitro transcription/translation systems. Such methods are described, for example, in U.S. Pat. Nos. 5,595,887; 5,116,750; 5,168,049 and 5,053,133; Olson et al., *Peptides,* 9, 301, 307 (1988). The solid phase peptide synthetic method is an established and widely used method, which is described in the following references: Stewart et al., *Solid Phase Peptide Synthesis,* W.H. Freeman Co., San Francisco (1969); Merrifield, *J. Am. Chem. Soc.,* 85 2149 (1963); Meienhofer in "Hormonal Proteins and Peptides," ed.; C. H. Li, Vol. 2 (Academic Press, 1973), pp. 48-267; Bavaay and Merrifield, "The Peptides," eds. E. Gross and F. Meienhofer, Vol. 2 (Academic Press, 1980) pp. 3-285; and Clark-Lewis et al., *Meth. Enzymol.* 287, 233 (1997). These polypeptides can be further purified by fractionation on immunoaffinity or ion-exchange columns; ethanol precipitation; reverse phase HPLC; chromatography on silica or on an anion-exchange resin such as DEAE; chromatofocusing; SDS-PAGE; ammonium sulfate precipitation; gel filtration using, for example, Sephadex G-75; or ligand affinity chromatography.

The polypeptides of the invention include polypeptides having amino acid exchanges, i.e., variant polypeptides, so long as the polypeptide variant is biologically active. The variant polypeptides include the exchange of at least one amino acid residue in the polypeptide for another amino acid residue, including exchanges that utilize the D rather than L form, as well as other well known amino acid analogs, e.g., N-alkyl amino acids, lactic acid, and the like. These analogs include phosphoserine, phosphothreonine, phosphotyrosine, hydroxyproline, gamma-carboxyglutamate; hippuric acid, octahydroindole-2-carboxylic acid, statine, 1,2,3,4,-tetrahydroisoquinoline-3-carboxylic acid, penicillamine, ornithine, citruline, N-methyl-alanine, para-benzoyl-phenylalanine, phenylglycine, propargylglycine, sarcosine, N-acetylserine, N-formylmethionine, 3-methylhistidine, 5-hydroxylysine, and other similar amino acids and imino acids and tert-butylglycine.

Conservative amino acid exchanges are preferred and include, for example; aspartic-glutamic as acidic amino acids; lysine/arginine/histidine as basic amino acids; leucine/isoleucine, methionine/valine, alanine/valine as hydrophobic amino acids; serine/glycine/alanine/threonine as hydrophilic amino acids. Conservative amino acid exchange also includes groupings based on side chains. Members in each group can be exchanged with another. For example, a group of amino acids having aliphatic side chains is glycine, alanine, valine, leucine, and isoleucine. These may be exchanged with one another. A group of amino acids having aliphatic-hydroxyl side chains is serine and threonine. A group of amino acids having amide-containing side chains is asparagine and glutamine. A group of amino acids having aromatic side chains is phenylalanine, tyrosine, and tryptophan. A group of amino acids having basic side chains is lysine, arginine, and histidine. A group of amino acids having sulfur-containing side chains is cysteine and methionine. For example, replacement of a leucine with an isoleucine or valine, an aspartate with a glutamate, a threonine with a serine, or a similar replacement of an amino acid with a structurally related amino acid may be accomplished to produce a variant polypeptide of the invention.

I. β(1,4)-Galactosyltransferase I Catalytic Domains of the Invention.

A. Catalytic Domains that Catalyze Formation of a Bond Between a Donor and an Acceptor to Form galactose-β(1,4)-N-acetylglucosamine Bonds.

It has been discovered that the catalytic domain of a β(1,4)-Galactosyltransferase I can be altered such that the catalytic domain is able to utilize a wide range of metal ions, including alkaline earth metals, which do not activate the wild-type enzyme during the catalytic β(1,4) linkage of galactose to N-acetylglucosamine. The ability to utilize a wide range of metal ions, instead of manganese as used by the wild-type enzyme, allows the catalytic domains of the invention to be used in conjunction with other synthetic methods used to produce biological products. For example, polypeptides may be produced through use of in vitro transcription/translation protocols that utilize magnesium. A catalytic domain of the invention can then be added to the reaction mixture to glycosylate the polypeptide in the presence of magnesium. In addition, the catalytic domains and polypeptides of the invention can be added to blood or platelet preparations to stabilize platelets so that they can be stored under chilled conditions (Hoffmeister et al., *Science* 301:1531 (2003)).

In some embodiments, the catalytic domains of the invention have a methionine exchanged with another amino acid at an amino acid position corresponding to 344 in the bovine β(1,4)-galactosyltransferase I (SEQ ID NO: 6). The corresponding methionine in the human and mouse β(1,4)-galactosyltransferase I is located at amino acid position 340 and 341 (SEQ ID Nos: 4 and 5 respectively). In mouse, human, and bovine β(1,4)-galactosyltransferase I, the methionine is located within the amino acid sequence CRMIRH (SEQ ID NO: 1). Accordingly, those of skill in the art can readily determine an equivalent amino acid in other β(1,4)-galactosyltransferase I catalytic domains.

An example of a specific exchange is M344H. In the presence of $Mg^{2+}$, the mutant, M344H-Gal-T1, exhibited 25% of the catalytic activity observed with the wild-type enzyme in the presence of $Mn^{2+}$. It also has higher $K_m$ for the substrates. The crystal structures of M344H-Gal-T1 in complex with either UDP-Gal.$Mn^{2+}$ or UDP-Gal.$Mg^{2+}$, and the crystal structure of M344E-Gal-T1 in complex with UDP-Gal.$Mn^{2+}$, have been determined at 2.3 Å resolutions. The structures show that the coordination stereochemistry of $Mg^{2+}$ is quite similar to that of $Mn^{2+}$. Both His344 and Glu344 in the mutants exhibit stronger coordination bonds with the metal ion compared to Met344 in the wild-type enzyme. This strong metal-ion coordination in the mutants appears to reduce $k_{cat}$ by interfering with the ability of the long flexible loop to undergo the required conformational changes during the catalytic cycle, but also by interfering with the formation of the transition state complex.

Catalytic domains and polypeptides of the invention in which amino acid residues involved with metal binding are mutated can optionally include an additional mutation corresponding to amino acid position 342. Such a mutation may include exchange of cysteine at amino acid position 342 with threonine (C342T). However, other amino acids may be exchanged for cysteine that provide an active catalytic domain.

B. Catalytic Domains that Catalyze the Formation of a Bond Between a Donor and an Acceptor to Form glucose-β(1,4)-N-acetylglucosamine Bonds.

Mutation of amino acid residues involved with metal binding can be combined with mutations in the donor binding site of β(1,4)-galactosyltransferase I that broaden the donor specificity of a catalytic domain or polypeptide of the invention. More specifically, substitution of amino acid residues located in the donor binding site of β(1,4)-galactosyltransferase I to provide greater flexibility and decreased steric hindrance allow glucose to be bound and chemically bonded to N-acetylglucosamine. Such mutations provide for broadened donor binding, such as binding of glucose, while still preserving interaction with amino acid residues active during catalytic bond formation between the donor and the acceptor. Without being bound by any theory, an example of a residue thought to be important for catalysis is a glutamic acid positioned at amino acid position 317 (E317) in the bovine β(1,4)-galactosyltransferase I. This glutamic acid in bovine β(1,4)-galactosyltransferase I corresponds to a glutamic acid residue at amino acid position 313 and at amino acid position 314 in the human and mouse β(1,4)-galactosyltransferase I, respectively. Accordingly, the invention provides β(1,4)-galactosyltransferase I mutants having amino acid substitutions, insertions, and deletions that provide greater flexibility and decreased steric hindrance in the donor binding site to allow the mutated β(1,4)-galactosyltransferase I to catalyze chemical bonding of the donor to an acceptor, such as N-acetylglucosamine or glucose.

In some embodiments, the catalytic domains of the invention have an amino acid at position 344 exchanged for another amino acid, and arginine exchanged with another amino acid at an amino acid position corresponding to 228 in the bovine β(1,4)-galactosyltransferase I (SEQ ID NO: 6). An example of a specific exchange is R228K. The corresponding arginine in the human and mouse β(1,4)-galactosyltransferase I is located at amino acid position 224 and 225 (SEQ ID Nos: 4 and 5, respectively). In mouse, human, and bovine β(1,4)-galactosyltransferase I, the arginine is located within the amino acid sequence FNRAKLL (SEQ ID NO: 2). Accordingly, those of skill in the art can readily determine an equivalent amino acid in other β(1,4)-galactosyltransferase I catalytic domains.

In other embodiments, the catalytic domains of the invention have an arginine exchanged with another amino acid at an amino acid position corresponding to 228, and an alanine exchanged with another amino acid at an amino acid position corresponding to 229 in the bovine β(1,4)-galactosyltransferase I.

Such catalytic domains are exemplified by a catalytic domain of bovine β(1,4)-galactosyltransferase I having the arginine at amino acid position 228 exchanged with lysine (R228K), and the alanine at amino acid position 229 exchanged with glycine (A229G). The corresponding alanine in the human and mouse β(1,4)-galactosyltransferase I is located at amino acid position 225 and 226 (SEQ ID Nos: 4 and 5, respectively). In mouse, human, and bovine β(1,4)-galactosyltransferase I, the arginine is located within the amino acid sequence FNRAKLL (SEQ ID NO: 2). Accordingly, those of skill in the art can readily determine an equivalent amino acid in other β(1,4)-galactosyltransferase I catalytic domains.

Catalytic domains and polypeptides of the invention in which amino acid residues involved with metal binding and donor binding are mutated can optionally include an additional mutation corresponding to amino acid position 342. Such a mutation may include exchange of cysteine at amino acid position 342 with threonine (C342T). However, other amino acids may be exchanged for cysteine that provide an active catalytic domain.

C. Catalytic Domains that Catalyze the Formation of a Bond Between a Donor and an Acceptor to Form N-acetylgalactosamine-β(1,4)-N-acetylglucosamine Bonds.

Mutations that broaden the metal ion specificity of a catalytic domain or polypeptide of the invention can also be combined with mutations that alter donor specificity.

For example, it was postulated that formation of a hydrogen bond between N-acetylgalactosamine and an amino acid residue adjoining the donor binding site in β(1,4)-galactosyltransferase I is responsible for poor transfer of N-acetylgalactosamine to an acceptor. It was also postulated that mutation of one or more amino acid residues in the donor binding site in β(1,4)-galactosyltransferase I to eliminate hydrogen bond formation with N-acetylgalactosamine allows the mutated β(1,4)-galactosyltransferase I to transfer N-acetylgalactosamine from a donor to an acceptor more efficiently. Therefore, the invention includes mutants of β(1,4)-galactosyltransferase I in which the metal ion specificity is altered, and in which hydrogen bonds that reduce transfer of N-acetylgalactosamine to an acceptor, such as N-acetylglucosamine or glucose, are reduced or absent.

In some embodiments, the catalytic domains of the invention have an amino acid substitution at amino acid position 344, and also have a tyrosine exchanged with another amino acid at an amino acid position corresponding to 289 in the bovine β(1,4)-galactosyltransferase I (SEQ ID NO: 6). Examples of specific exchanges are Y289L, Y289I, and Y289N. The corresponding tyrosine in the human and mouse β(1,4)-galactosyltransferase I is located at amino acid position 285 and 286 (SEQ ID Nos: 4 and 5, respectively). In mouse, human, and bovine β(1,4)-galactosyltransferase I, the tyrosine is located within the amino acid sequence YVQYFGG (SEQ ID NO: 3). Accordingly, those of skill in the art can readily determine equivalent amino acids in other β(1,4)-galactosyltransferase I catalytic domains.

Mutants in which the tyrosine corresponding to that located at amino acid position 289 in the bovine β(1,4)-galactosyltransferase I has been exchanged by another amino acid may optionally include an additional mutation corresponding to amino acid position 342. Such a mutation may include exchange of cysteine at amino acid position 342 with threonine (C342T). However, other amino acids may be exchanged for cysteine that provide an active catalytic domain.

D. Catalytic Domains that Catalyze the Formation of a Bond Between a Donor and an Acceptor to Form N-acetylgalactosamine-β(1,4)-glucose Bonds.

β(1,4)-galactosyltransferase I catalytic domains and polypeptides of the invention, as described herein, that are able to catalyze chemical bond formation of N-acetylgalactosamine to an acceptor may be used in conjunction with α-lactalbumin to catalyze the formation of N-acetylgalactosamine-β(1,4)-glucose bonds.

α-Lactalbumin is a mammary gland-specific calcium-binding protein that alters the sugar acceptor specificity of β(1,4)-galactosyltransferase I toward glucose. Consequently, α-lactalbumin may be used to alter the acceptor specificity β(1,4)-galactosyltransferase I, and mutants thereof that are described herein, to efficiently catalyze N-acetylgalactosamine-β(1,4)-glucose bond formation. Conditions for use of α-lactalbumin in conjunction with a galactosyltransferase, or active domain thereof, have been described (Ramakrishnan et al., *J. Biol. Chem.*, 276:37665 (2001)).

E. Catalytic Domains that Catalyze the Formation of a Bond Between a Donor and an Acceptor to Form N-acetylglucosamine-β(1,4)-N-acetylglucosamine Bonds, Oligo N-acetylgalactosamine-β(1,4)-N-acetylglucosamine, and mannose-β(1,4)-N-acetylglucosamine.

The invention provides additional catalytic domains and polypeptides having mutations that broaden the metal ion specificity, and mutations that alter donor specificity.

For example, a catalytic domain obtained from bovine β(1,4)-galactosyltransferase I having exchanges at amino acid positions 228 (R228K) and 289 (Y289L) was able to catalyze the linkage of N-acetylglucosamine to N-acetylglucosamine to form a N-acetylglucosamine-β(1,4)-N-acetylglucosamine bond. The same mutant catalytic domain was able to catalyze the linkage of N-acetylgalactosamine to N-acetylglucosamine to form oligo N-acetylgalactosamine-β(1,4)-N-acetylglucosamine. The broadened donor specificity was further demonstrated by the ability of the mutant catalytic domain to catalyze the linkage of mannose to N-acetylglucosamine to form mannose-β(1,4)-N-acetylglucosamine. Accordingly, numerous mutant catalytic domains having altered donor specificity may be created by mutating amino acids corresponding to those at positions corresponding to 228 and 289 of the bovine β(1,4)-galactosyltransferase I. As described above, these amino acid positions may be readily determined in galactosyltransferase enzymes obtained from other organisms, such as humans, and mutated to produce additional catalytic domains having altered donor specificity. These amino acid mutations that alter donor specificity can be combined with mutations that broaden metal ion specificity, such as mutation of an amino acid corresponding to the methionine at amino acid position 344 in the bovine β(1,4)-galactosyltransferase I.

These catalytic domains and polypeptides of the invention can optionally include an additional mutation corresponding to amino acid position 342. Such a mutation may include exchange of cysteine at amino acid position 342 with threonine (C342T). However, other amino acids may be exchanged for cysteine that provide an active catalytic domain.

F. Catalytic Domains that Catalyze the Formation of a Bond Between a Donor and an Acceptor Having a Bulks Side-Group to Form for Example, galactose-β(1,4)-N-acetylglucosamine-6-$SO_3$ Bonds.

The invention provides additional catalytic domains and polypeptides having mutations that broaden the metal ion specificity, and mutations that alter acceptor specificity.

The metal ion specificity, and acceptor specificity of a catalytic domain obtained from a galactosyltransferase may be altered to create catalytic domains capable of transferring a donor onto an acceptor having a bulky and/or charged side-group in the presence of a broad range of metal ions.

An example of such an altered catalytic domain obtained from bovine β(1,4)-galactosyltransferase I has substitutions at amino acid positions 279 (K279S) and 280 (F280T). This altered catalytic domain is able to catalyze the transfer of galactose to N-acetylglucosamine-6-$SO_3$ to form galactose-β(1,4)-N-acetylglucosamine-6-$SO_3$. Additional catalytic domains may be created by altering one or more amino acid residues at positions corresponding to 279 and 280 of the bovine β(1,4)-galactosyltransferase I. As described above, these amino acid positions may be readily determined in galactosyltransferase enzymes obtained from other organisms, such as humans, and mutated to produce additional catalytic domains having altered acceptor specificity. These catalytic domains may be further altered to include additional amino acid exchanges that broaden the metal ion specificity of the catalytic domain.

The amino acids at positions corresponding to 279 and 280 in the bovine β(1,4)-galactosyltransferase I may be exchanged individually or together to create many different catalytic domains having altered acceptor sites able to accept numerous acceptors having bulky (sterically large) or charged side-groups. Such altered catalytic domains may be used to catalyze linkage of sugars from a donor to an acceptor having a desired side-chain.

These catalytic domains and polypeptides of the invention can optionally include an additional mutation corresponding to amino acid position 342. Such a mutation may include exchange of cysteine at amino acid position 342 with threonine (C342T). However, other amino acids may be exchanged for cysteine that provide an active catalytic domain.

II. Catalytic Domains of the Invention May be Included within Full-Length (1,4)-galactosyltransferase I Enzymes or in Recombinant Molecules Containing the Catalytic Domains.

Peptides of the invention include isolated catalytic domains, full-length β(1,4)-galactosyltransferase I enzymes containing a catalytic domain of the invention, as well as recombinant polypeptides comprising a catalytic domain of the invention that are linked to additional amino acids. Such polypeptides may be expressed from DNA constructs and expression cassettes that are produced through use of recombinant methods. Such methods have been described in, for example, Sambrook et al., Molecular Cloning: A Laboratory Manual, 3rd edition, Cold Spring Harbor Press, Cold Spring Harbor, N.Y. (2001).

Galactosyltransferase enzymes containing a catalytic domain of the invention may be produced in soluble form. Methods that may be used to produce such soluble enzymes have been described (U.S. Pat. No. 5,032,519). Briefly, a hydrophobic transmembrane anchor region of a galactosyltransferase is removed to produce an enzyme that is in soluble form.

Alternatively, β(1,4)-galactosyltransferase enzymes containing a catalytic domain of the invention may be produced such that they are anchored in the membrane of a cell that expresses the galactosyltransferase. Such enzymes may be produced that are anchored in the membranes of prokaryotic and eukaryotic cells. Methods to produce such enzymes have been described (U.S. Pat. No. 6,284,493).

Briefly, in the case of procaryotes, the signal and transmembrane sequences of the galactosyltransferase are replaced by a bacterial signal sequence, capable of effecting localization of the fusion protein to the outer membrane. Suitable signal sequences include, but are not limited to those from the major *E. coli* lipoprotein Lpp and lam B. In addition, membrane spanning regions from Omp A, Omp C, Omp F or Pho E can be used in a tripartite fusion protein to direct proper insertion of the fusion protein into the outer membrane. Any procaryotic cells can be used in accordance with the present invention including but not limited to *E. coli Bacillus* sp., and *Pseudomonas* sp. as representative examples.

In another embodiment, the native transmembrane domain of the galactosyltransferase is replaced by the transmembrane domain of a bacterial outer membrane protein. In this embodiment, the galactosyltransferase signal sequence and the bacterial transmembrane region act in concert to anchor the galactosyltransferase to the bacterial outer cell membrane. Nearly any outer membrane bound protein is suitable for this use including but not limited to Omp A, Omp C, and Omp F, Lpp, and Lam B. The catalytic portion of the galactosyltransferase should be fused to an extracellular loop in the bacterial transmembrane region in order to insure proper orientation of the fusion protein on the outer membrane surface and not in the cytoplasm or periplasm of the cell. Insertion of a protein into such a loop region has been previously reported (Charbit et al., *J. Bacteriology*, 173:262 (1991); Francisco et al., *Proc. Natl. Acad. Sci.* 89:2713 (1992)).

The present invention is also applicable for use with eukaryotic cells resulting in cell surface expression of galactosyltransferases in known culturable eucaryotic cells including but not limited to yeast cells, insect cells, chinese hamster ovary cells (CHO cells), mouse L cells, mouse A9 cells, baby hamster kidney cells, C127 cells, COS cells, Sf9 cells, and PC8 cells.

In another embodiment of the present invention, the transmembrane domain of the galactosyltransferase is replaced by the transmembrane domain of a plasma membrane protein. The transmembrane domain of any resident plasma membrane protein will be appropriate for this purpose. The transmembrane portions of the M6 P/IGF-II receptor, LDL receptor or the transferrin receptor are representative examples.

In another embodiment the Golgi retention signal of the galactosyltransferase is disrupted by site-directed mutagenesis. This approach mutates the amino acids responsible for localizing the galactosyltransferase to the Golgi compartment. The resultant galactosyltransferase is transported to the plasma membrane where it becomes anchored via its modified transmembrane sequences. Substitution of isoleucine residues for the native amino acids in the transmembrane region of the β(1,4)galactosyltransferase has been shown to preferentially localize the enzyme to the plasma membrane instead of the Golgi apparatus (Masibay et al., *J. Biol. Chem.* 268:9908 (1993)).

III. A Stem Region that Promotes the In Vitro Folding of a Catalytic Domain of a Galactosyltransferase.

β(1,4)-galactosyltransferase I is a type II Golgi resident protein with a short cytoplasmic tail, a transmembrane domain followed by a stem region and has a globular catalytic domain that faces the Golgi lumen. When a catalytic domain of β(1,4)-galactosyltransferase I is expressed in *E. coli*, it forms insoluble inclusion bodies. These inclusion bodies can be collected and then solubilized and folded in vitro to produce catalytically active domains. Thus, the in vitro folding efficiency is directly related to the quantity of active enzyme that is produced from the isolated inclusion bodies. Accordingly, methods to increase the in vitro folding efficiency would provide increased production of catalytic domains that can be used to create useful products.

The invention provides materials and methods that improve in vitro folding of catalytic domains from galactosyltransferases that are related to the use of a stem region (for example, SEQ ID NOs: 7 and 8) of β(1,4)-galactosyltransferase I. It is thought that fusion of a stem region from a β(1,4)-galactosyltransferase I to the amino-terminus of a catalytic domain of a β(1,4)-galactosyltransferase I produces increased in vitro folding efficiency of the catalytic domain. This increase in folding is thought to be universal among β(1,4)-galactosyltransferase I enzymes and was demonstrated with both the bovine and human enzymes.

It is further thought that inclusion of PEG-4000 and L-Arg in the folding reaction will result in a four-fold to seven-fold increase in catalytic domains having altered metal ion specificity that are natively folded when compared to refolding of the catalytic domain alone in the absence of PEG-4000 and L-Arg. PEG-4000 and L-arginine are thought to beneficially affect the solubility of folding intermediates of both catalytic domain-proteins (CD-proteins) and stem region/catalytic domain proteins (SRCD-proteins) during in vitro folding or protein obtained from inclusion bodies. It is thought that the SR-domain, like PEG4000 and L-arginine, helps to solubilize the folding intermediates, and hence enhanced the formation of both native and misfolded-SRCD molecules. The presence of PEG-4000 and L-arginine enhanced the solubilization of the folding intermediates of SRCD-molecules even further.

The misfolded SRCD proteins, in contrast to the majority of CD-proteins, remained soluble even in the absence of PEG4000 and L-arginine. Therefore, the misfolded SRCD-proteins were not removed as precipitates during dialysis. Misfolded SRCD-proteins can be separated from properly folded proteins through binding on UDP-agarose columns. Thus, the SR-domain is thought to act as a solubilizing agent both for the misfolded and folded catalytic domain. It is thought that the increased solubility of SRCD-proteins is produced by preventing aggregation of misfolded proteins. In this respect its mode of action is thought to resemble the action of chaperone proteins. The positive effect of the N-terminal stem region in the folding and stability of the native protein is very useful for producing large quantities of other galactosyltransferase family members.

The in vitro folding efficiency of bovine β(1,4)-galactosyltransferase I was further increased by substituting the cysteine at amino acid position 342 with a threonine (C342T). Analogous mutations can be made in β(1,4)-galactosyltransferase I enzymes from other organisms.

It has been determined that the wild-type bovine SRCDβ4Gal-T1, folded and purified from inclusion bodies, was cleaved at Ser96 within the stem region over a short period of time. Therefore, to decrease degradation of bovine SRCDβ4Gal-T1, the serine at amino acid position 96 can be exchanged with an Ala to produce S96A-SRCDβ4Gal-T1. After folding and purification from bacterial inclusion bodies, S96A-SRCDβ4Gal-T1 was found to be more stable over a long period of time when compared to SRCDβ4Gal-T1, which did not include the S96A mutation.

Accordingly, the invention includes stem regions from members of the galactosyltransferase family that can be fused to a catalytic domain of a galactosyltransferase to provide increased in vitro folding of the catalytic domain. Such stem regions can be readily determined based on amino acid sequence homology to the bovine stem region and tested for the ability to promote folding of a galactosyltransferase catalytic domain. The invention also includes the mutants disclosed herein and their corresponding analogs in other species.

General methods for isolating and folding inclusion bodies containing galactosyltransferase catalytic domains have been previously described (Ramakrishnan et al., *J. Biol. Chem.*, 276:37665 (2001)). These methods may be used in conjunction with the stem region of the invention, PEG-4000, and L-Arg to increase the folding efficiency of a galactosyltransferase catalytic domain.

These methods are described in the examples section herein.

IV. Nucleic Acid Segments Encoding Catalytic Domains of β(1,4)-Galactosyltransferase I, Expression Cassettes that Include the Nucleic Acid Segments, and Cells that Include the Nucleic Acid Segments and Expression Cassettes.

The present invention provides isolated nucleic acid segments that encode catalytic domains of β(1,4)-galactosyltransferase I having altered metal ion, donor, or acceptor specificity. The present invention also provides nucleic acid segments that encode amino acid segments that promote proper folding of catalytic domains from galactosyltransferases, such as β(1,4)-galactosyltransferase I.

Nucleic acid sequences encoding human β(1,4)-galactosyltransferase I (SEQ ID NO: 8), as well as other β(1,4)-galactosyltransferases I from other organisms are available. These nucleic acid sequences can be modified to encode the catalytic domains and amino acid segments of the invention through use of well-known techniques (Sambrook et al., Molecular Cloning: A Laboratory Manual, 3rd edition, Cold Spring Harbor Press, Cold Spring Harbor, N.Y. (2001)). For example, a portion of the nucleic acid sequence encoding human β(1,4)-galactosyltransferase I (SEQ ID NO: 11) can be inserted into an expression vector such that an amino acid segment corresponding to the catalytic domain of human β(1,4)-galactosyltransferase I (SEQ ID NO: 9) is expressed upon transformation of a cell with the expression vector. In another example, bovine β(1,4)-galactosyltransferase I can be altered to exchange the methionine at amino acid position 344 with histidine through use of site-directed mutagenesis. Similar methods may be used to produce nucleic acid segments encoding additional mutants, catalytic domains, and polypeptides described herein.

The nucleic acid segments of the invention may be optimized for expression in select cells. Codon optimization tables are available. Harlow and Lane, *Antibodies: A Laboratory Manual* Cold Spring Harbor Laboratory Press, 1988.

The nucleic acid segments can be inserted into numerous types of vectors. A vector may include, but is not limited to, any plasmid, phagemid, F-factor, virus, cosmid, or phage in double or single stranded linear or circular form which may or may not be self transmissible or mobilizable. The vector can also transform a prokaryotic or eukaryotic host either by integration into the cellular genome or exist extrachromosomally (e.g., autonomous replicating plasmid with an origin of replication).

Preferably the nucleic acid segment in the vector is under the control of, and operably linked to, an appropriate promoter or other regulatory elements for transcription in vitro or in a host cell such as a eukaryotic cell or microbe, e.g. bacteria. The vector may be a bi-functional expression vector which functions in multiple hosts. In the case of genomic DNA, this may contain its own promoter or other regulatory elements and in the case of cDNA this may be under the control of a promoter or other regulatory sequences for expression in a host cell.

Specifically included are shuttle vectors by which is meant a DNA vehicle capable, naturally or by design, of replication in two different host organisms, which may be selected from bacteria and eukaryotic cells (e.g., mammalian, yeast or fungal).

The vector may also be a cloning vector which typically contains one or a small number of restriction endonuclease recognition sites at which nucleic acid segments can be inserted in a determinable fashion. Such insertion can occur without loss of essential biological function of the cloning vector. A cloning vector may also contain a marker gene that is suitable for use in the identification and selection of cells transformed with the cloning vector. Examples of marker genes are tetracycline resistance, hygromycin resistance or ampicillin resistance. Many cloning vectors are commercially available (Stratagene, New England Biolabs, Clonetech).

The nucleic acid segments of the invention may also be inserted into an expression vector. Typically an expression vector contains (1) prokaryotic DNA elements coding for a bacterial replication origin and an antibiotic resistance gene to provide for the amplification and selection of the expression vector in a bacterial host; (2) regulatory elements that control initiation of transcription such as a promoter; and (3) DNA elements that control the processing of transcripts such as introns, transcription termination/polyadenylation sequence.

Methods to introduce a nucleic acid segment into a vector are well known in the art (Sambrook et al., 1989). Briefly, a vector into which the nucleic acid segment is to be inserted is treated with one or more restriction enzymes (restriction endonuclease) to produce a linearized vector having a blunt end, a "sticky" end with a 5' or a 3' overhang, or any combination thereof. The vector may also be treated with a restriction enzyme and subsequently treated with another modifying enzyme, such as a polymerase, an exonuclease, a phosphatase or a kinase, to create a linearized vector that has characteristics useful for ligation of a nucleic acid segment into the vector. The nucleic acid segment that is to be inserted into the vector is treated with one or more restriction enzymes to create a linearized segment having a blunt end, a "sticky" end with a 5' or a 3' overhang, or any combination thereof. The nucleic acid segment may also be treated with a restriction enzyme and subsequently treated with another DNA modifying enzyme. Such DNA modifying enzymes include, but are not limited to, polymerases, exonucleases, phosphatases or kinases, to create a polynucleic acid segment that has characteristics useful for ligation of a nucleic acid segment into the vector.

The treated vector and nucleic acid segment are then ligated together to form a construct containing a nucleic acid segment according to methods known in the art (Sambrook, 2002). Briefly, the treated nucleic acid fragment and the treated vector are combined in the presence of a suitable buffer and ligase. The mixture is then incubated under appropriate conditions to allow the ligase to ligate the nucleic acid fragment into the vector. It is preferred that the nucleic acid fragment and the vector each have complimentary "sticky" ends to increase ligation efficiency, as opposed to blunt-end ligation. It is more preferred that the vector and nucleic acid fragment are each treated with two different restriction enzymes to produce two different complimentary "sticky" ends. This allows for directional ligation of the nucleic acid fragment into the vector, increases ligation efficiency and avoids ligation of the ends of the vector to reform the vector without the inserted nucleic acid fragment.

Suitable procaryotic vectors include but are not limited to pBR322, pMB9, pUC, lambda bacteriophage, m13 bacteriophage, and Bluescript®. Suitable eukaryotic vectors include but are not limited to PMSG, pAV009/A+, PMTO10/A+, pMAM neo-5, bacculovirus, pDSVE, YIP5, YRP17, YEP. It will be clear to one of ordinary skill in the art which vector or promoter system should be used depending on which cell type is used for a host cell.

The invention also provides expression cassettes which contain a control sequence capable of directing expression of a particular nucleic acid segment of the invention either in vitro or in a host cell. The expression cassette is an isolatable unit such that the expression cassette may be in linear form and functional in in vitro transcription and translation assays. The materials and procedures to conduct these assays are commercially available from Promega Corp. (Madison, Wis.). For example, an in vitro transcript may be produced by placing a nucleic acid segment under the control of a T7 promoter and then using T7 RNA polymerase to produce an in vitro transcript. This transcript may then be translated in vitro through use of a rabbit reticulocyte lysate. Alternatively, the expression cassette can be incorporated into a vector allowing for replication and amplification of the expression cassette within a host cell or also in vitro transcription and translation of a nucleic acid segment.

Such an expression cassette may contain one or a plurality of restriction sites allowing for placement of the nucleic acid segment under the regulation of a regulatory sequence. The expression cassette can also contain a termination signal operably linked to the nucleic acid segment as well as regulatory sequences required for proper translation of the nucleic acid segment. Expression of the nucleic acid segment in the expression cassette may be under the control of a constitutive promoter or an inducible promoter which initiates transcription only when the host cell is exposed to some particular external stimulus.

The expression cassette may include in the 5'-3' direction of transcription, a transcriptional and translational initiation region, a nucleic acid segment and a transcriptional and translational termination region functional in vivo and/or in vitro. The termination region may be native with the transcriptional initiation region, may be native with the nucleic acid segment, or may be derived from another source. Numerous termination regions are known in the art. Guerineau et al., *Mol. Gen. Genet.*, 262:141 (1991); Proudfoot, *Cell*, 64:671 (1991); Sanfacon et al., *Genes Dev.*, 5:141 (1991); Munroe et al., *Gene*, 91:151 (1990); Ballas et al., *Nucleic Acids Res.*, 17:7891 (1989); Joshi et al., *Nucleic Acid Res.* 15:9627 (1987).

The regulatory sequence can be a nucleic acid sequence located upstream (5' non-coding sequences), within, or downstream (3' non-coding sequences) of a coding sequence, and which influences the transcription, RNA processing or stability, or translation of the associated coding sequence. Regulatory sequences can include, but are not limited to enhancers, promoters, repressor binding sites, translation leader sequences, introns, and polyadenylation signal sequences. They may include natural and synthetic sequences as well as sequences which may be a combination of synthetic and natural sequences. While regulatory sequences are not limited to promoters, some useful regulatory sequences include constitutive promoters, inducible promoters, regulated promoters, tissue-specific promoters, viral promoters and synthetic promoters.

A promoter is a nucleotide sequence that controls expression of the coding sequence by providing the recognition for RNA polymerase and other factors required for proper transcription. A promoter includes a minimal promoter, consisting only of all basal elements needed for transcription initiation, such as a TATA-box and/or initiator that is a short DNA sequence comprised of a TATA-box and other sequences that serve to specify the site of transcription initiation, to which regulatory elements are added for control of expression. A promoter may be inducible. Several inducible promoters have been reported (*Current Opinion in Biotechnology* 7:168 (1996)). Examples include the tetracycline repressor system, Lac repressor system, copper-inducible systems, and salicylate-inducible systems (such as the PR1a system). Also included are the benzene sulphonamide- (U.S. Pat. No. 5,364,780) and alcohol- (WO 97/06269 and WO 97/06268) inducible systems and glutathione S-transferase promoters. In the case of a multicellular organism, the promoter can also be specific to a particular tissue or organ or stage of development.

An enhancer is a DNA sequence which can stimulate promoter activity and may be an innate element of the promoter or a heterologous element inserted to enhance the level or tissue specificity of a promoter. It is capable of operating in both orientations (normal or flipped), and is capable of functioning even when moved either upstream or downstream from the promoter. Both enhancers and other upstream promoter elements bind sequence-specific DNA-binding proteins that mediate their effects.

The expression cassette can contain a 5' non-coding sequence which is a nucleotide sequence located 5' (upstream) to the coding sequence. It is present in the fully processed mRNA upstream of the initiation codon and may affect processing of the primary transcript to mRNA, stability of the mRNA, or translation efficiency (Turner et al., *Molecular Biotechnology*, 3:225 (1995)).

The expression cassette may also contain a 3' non-coding sequence which is a nucleotide sequence located 3' (downstream) to a coding sequence and includes polyadenylation signal sequences and other sequences encoding regulatory signals capable of affecting mRNA processing or gene expression. The polyadenylation signal is usually characterized by affecting the addition of polyadenylic acid tracts to the 3' end of the mRNA precursor.

The invention also provides a construct containing a vector and an expression cassette. The vector may be selected from, but not limited to any vector previously described. Into this vector may be inserted an expression cassette through methods known in the art and previously described (Sambrook et al., 1989). In one embodiment, the regulatory sequences of the expression cassette may be derived from a source other than the vector into which the expression cassette is inserted. In another embodiment, a construct containing a vector and an expression cassette is formed upon insertion of a nucleic acid segment of the invention into a vector that itself contains regulatory sequences. Thus, an expression cassette is formed upon insertion of the nucleic acid segment into the vector. Vectors containing regulatory sequences are available commercially and methods for their use are known in the art (Clonetech, Promega, Stratagene).

The expression cassette, or a vector construct containing the expression cassette may be inserted into a cell. The expression cassette or vector construct may be carried eposomally or integrated into the genome of the cell.

A variety of techniques are available and known to those skilled in the art for introduction of constructs into a cellular host. Transformation of bacteria and many eukaryotic cells may be accomplished through use of polyethylene glycol, calcium phosphate, viral infection, phage infection, electroporation and other methods known in the art. Other transformation methods are available to those skilled in the art, such as direct uptake of foreign DNA constructs (see EP 295959), techniques of electroporation (Fromm et al. *Nature* (*London*) 319:791 (1986) or high velocity ballistic bombardment with metal particles coated with the nucleic acid constructs (Kline et al. *Nature* (*London*) 327:70 (1987), and U.S. Pat. No. 4,945,050).

The selection of an appropriate expression vector will depend upon the method of introducing the expression vector into host cells. Typically an expression vector contains (1) prokaryotic DNA elements coding for abacterial origin of replication and an antibiotic resistance gene to provide for the amplification and selection of the expression vector in a bacterial host; (2) DNA elements that control initiation of transcription, such as a promoter, (3) DNA elements that control the processing of transcripts, such as introns, transcription termination/polyadenylation sequence; and (4) a reporter gene that is operatively linked to the DNA elements to control transcription initiation. Useful reporter genes include β-galactosidase, chloramphenicol acetyl transferase, luciferase, green fluorescent protein (GFP) and the like.

V. Methods to Synthesize galactose-β(1,4)-N-acetylglucosamine Moieties; glucose-β(1,4)-N-acetylglucosamine Moieties; N-acetylgalactosamine-β(1,4)-N-acetylglucosamine Moieties; N-acetylgalactosamine-β(1,4)-glucose Moieties; N-acetylglucosamine-β(1,4)-N-acetylglucosamine Moieties; mannose-β(1,4)-N-acetylglucosamine Moieties; and galactose-β(1,4)-N-acetylglucosamine-6-SO$_3$ Moieties.

Catalytic domains of the invention having altered metal ion specificity can be used to catalyze the linkage of galactose and N-acetylglucosamine in the presence of a broad range of metal ions. Catalytic domains of the invention having altered metal ion specificity that are coupled with altered donor and/or acceptor specificity can be used to catalyze the linkage of numerous sugars from a donor to numerous acceptor sugars in the presence of a broad range of metal ions, including but not limited to magnesium and zinc. Linkage of sugar derivatives can also achieved in the presence of a broad range of metal ions through use of the altered catalytic domains of the invention due to their expanded metal ion, donor, and/or acceptor specificity.

For example, in the presence of a broad range of metal ions, the catalytic domains of section IA can be used to catalyze the linkage of galactose and N-acetylglucosamine; the catalytic domains of section IB can be used to catalyze the linkage of glucose and N-acetylglucosamine; the catalytic domains of section IC can be used to catalyze the linkage of N-acetylgalactosamine and N-acetylglucosamine; many of the catalytic domains described herein can be used in association with α-lactalbumin to catalyze linkage of a sugar to glucose, as described in section ID; the catalytic domains of section IE can be used to catalyze the linkage of N-acetylglucosamine and N-acetylglucosamine, N-acetylgalactosamine to N-acetylglucosamine, and mannose to N-acetylglucosamine; and the catalytic domains of section IE can be used to catalyze the linkage of a donor and an acceptor having a bulky side-group, such as linking galactose to N-acetylglucosamine-6-SO$_3$.

Acceptors may be free in solution or linked to another molecule. For example, an acceptor may be linked to a protein, another sugar, a sugar derivative, and the like. An acceptor may also be linked to a solid support that provides a platform to which donors may be added sequentially to form oligosaccharides, and derivatives thereof, having a specified sequence.

Generally, the linkage between a donor and an acceptor is accomplished by incubating a catalytic domain of the invention with a desired donor and a desired acceptor under conditions of appropriate temperature, pH, and divalent metal concentration to allow linkage of the donor to the acceptor.

For example, the galactose and N-acetylgalactosyltransferase activity of β(1,4)-galactosyltransferase I can be determined using the following assay conditions: a 100 µl incubation mixture containing 50 mM β-benzyl-GlcNAc, 10 mM MnCl$_2$, 10 mM Tris-HCl (pH 8.0), 500 µM UDP-Gal or UDP-GalNAc, and 20 ng of β(1,4)-galactosyltransferase I can be incubated at 37° C. for 10 minutes to promote coupling of a donor sugar to an acceptor sugar. While these conditions are provided as an example, it is understood that many other conditions may be used to chemically link a donor to an acceptor using the altered catalytic domains of the invention.

VI. Methods to Prepare Oligosaccharides.

The invention provides methods to synthesize oligosaccharides, especially oligosaccharides having preselected sequences through use of the altered catalytic domains of the invention. Generally, the methods involve the sequential addition of a sugar, or derivative thereof, to the end of a growing oligosaccharide chain. Such methods have been described using enzymes other than those of the invention (U.S. Pat. No. 6,284,493).

Briefly, a donor and an acceptor may be incubated with an altered catalytic domain of the invention under conditions that allow the donor to be linked to the acceptor. These conditions are described in the examples section herein.

In one example, the donor and the acceptor may be combined with a catalytic domain of the invention in solution. The solution is then incubated to allow the donor to be linked to the acceptor. The newly linked molecule may be isolated and then added to a second solution containing a second donor and a second transferase enzyme. This cycle may be repeated with a specific donor added at each cycle such that an oligosaccharide having a specific sequence is produced.

In another example, an acceptor may be linked to a solid support. The solid support may then be immobilized in a structure such as a column or a tray. A donor and a catalytic domain of the invention can then be incubated with the immobilized acceptor under conditions that allow the donor to be linked to the acceptor. The solid support is then washed to remove any unlinked donor and catalytic domain present. A second donor and a second transferase enzyme can then be added and incubated under conditions that allow the donor to be linked to the acceptor. This cycle can be repeated to allow for the rapid and large-scale production of oligosaccharides having defined sequences. In addition, this method may be readily adapted for use in an automated system. This system may be used without the need for protecting groups on the acceptor or the donor due to the use of enzymes that catalyze the linkage of a given donor to a given acceptor. Accordingly, an advantage of this method is that mild reaction conditions may be used that do not damage the growing oligosaccharide chain. Another advantage of the method is the short cycling time required to add monomers onto the growing oligosaccharide chain due to the lack of a need to protect and deprotect the growing oligosaccharide chain.

Other methods for using the catalytic domains of the invention to synthesize sequences of predetermined oligosaccharides and derivatives thereof may also be used. However, these methods will utilize a galactosyltransferase having an altered acceptor site, an altered donor site, or altered donor and acceptor sites.

VII. Methods to Increase the Immunogenicity of an Antigen.

The invention also provides methods to increase the immunogenicity of an antigen. Generally, the methods involve incubating an antigen with a catalytic domain of the invention such that a sugar is transferred from a donor to an acceptor through the action of a catalytic domain.

The methods of the invention may be used in association with nearly any acceptor containing material against which an immune response is desired. For example, sugars may be transferred from a donor to an acceptor that is linked to a whole cell. The cell can then be killed through irradiation or chemical means and administered to an animal to elicit an immune response. Cell membranes may be used in a similar manner. Methods to create an immune response against cells and cell membranes are described in U.S. Pat. No. 6,361,775.

The immunogenicity of a virus or subunit thereof may be increased according to the methods of the invention and used as an improved vaccine. For example, for a virus that contains a glycoprotein as a component of the virion, one or more sugars may be added to the glycoprotein by propagation of the virus in a cell that expresses a catalytic domain of the invention. Alternatively, one or more sugars may be directly added to the glycoprotein using a catalytic domain of the invention. Furthermore, there exist viruses without envelopes that contain complex carbohydrates. Sugars may be added onto these carbohydrates through use of a catalytic domain of the invention.

Viral subunits may be obtained from virions using biochemical methods or they can be expressed by recombinant means in suitable eukaryotic cells. Methods of expressing viral subunits are common in the art. These methods may vary according to the type of virus used. For example, methods of expressing viral subunits are described in the following articles and in the references cited therein: Possee, *Virus Research* 5:43 (1986); Kuroda et. al., *EMBO J.,* 5: 1359 (1986); Doerfler, *Curr. Topics Microbiol. Immunol.,* 131:51 (1986); Rigby, *J. Gen. Virol.,* 64:255 (1983); Mackett et al., In: DNA Cloning, A Practical Approach, Vol II, Ed. D. M. Glover, IRL Press, Washington, D.C. (1985); Rothestein, In: DNA Cloning, A Practical Approach, Supra (1985); Kinney et al., *J. Gen. Virol.,* 69:3005 (1988); Panical et al., *Proc. Natl. Acad. Sci.,* 80:5364 (1983); Small et al., In: Vaccinia Viruses as Vectors for Vaccine Antigens, pp. 175-178, Ed. J. Quinnan, Elsevier, N.Y. (1985).

Viruses for which vaccines are currently available and whose immunogenicity can be improved according to the methods of the invention include influenza virus (Orthomyxovirus); rabies virus (Rhabdovirus); hepatitis B virus (Hepadnavirus); eastern, western and Venezuelan equine encephalitis virus (Togavirus/Alphavirus genus); and, Japanese encephalitis virus, tick-borne encephalitis virus and Russian spring-summer encephalitis virus (Flavivirus); Rift Valley fever virus (Bunyavirus)(reviewed: Melnick, In: High Technology Route to Virus Vaccines Ed. Dreesman, Bronson and Kennedy, American Society for Microbiology, Washington, D.C. (1985); Ogra et al., *Prog. Med. Virol.,* 37:156 (1990)). Viruses for which vaccines are not yet commercially available but which may also be useful with the methods of the invention include, but are not limited to human immunodeficiency and human T-cell leukemia viruses (Retrovirus); respiratory syncytial virus and other paramyxoviruses (Paramyxovirus); herpes simplex viruses types 1 and 2, varicella zoster virus, cytomegalovirus and other herpes viruses (Herpesviruses); dengue virus and Saint Louis encephalitis virus (Flavivirus); hantaan virus (Bunyavirus); Lassa virus (Arenavirus); and, rotavirus (Reovirus). In addition, there exist viral vaccines comprising live attenuated viruses, the administration of which to humans is associated with some measure of risk of mild to severe side effects. It is now possible according to the methods of the invention to enhance the immunogenicity of killed virus vaccines which may serve to reduce the use of their live, more risk-associated counterparts. Thus, vaccines which currently comprise live virus, such as measles virus, mumps virus, rubellavirus etc. are all encompassed by the invention.

Vaccines are prepared by suspension of a suitable concentration of an antigen that has been linked to a sugar, through the action of a catalytic domain of the invention, in a pharmaceutically acceptable carrier. The composition of the carrier will depend upon the type of vaccine and the route of administration and will be readily apparent to one skilled in the art. The vaccine may be administered in a dose of $10^2$ to $10^9$ cells per dose (in the case of whole cells) or a similar equivalent of cell membranes. In the case of viral vaccines, virus may be administered in dose ranging from 1 μg to 50 mg of virus per dose, or a similar equivalent of subunit. Determination of the appropriate dosage of vaccine will be apparent to one of skill in the art and will depend upon the antigens comprising the vaccine, the age of the patient and their general and immunological health.

In order to improve the efficacy of vaccines prepared according to the methods of the invention, patients may be pretreated with adjuvant at the site of vaccination several days prior to administration of vaccine. Pretreatment with adjuvant serves to induce migration of macrophages to the site of inoculation, thereby enhancing the rate of phagocytosis of treated antigens. In the case of viral vaccines, patients may be treated with adjuvant and vaccine simultaneously. Adjuvants suitable for this purpose include aluminum hydroxide and like adjuvants.

Vaccines are administered to a mammal, particularly a human, either subcutaneously, intramuscularly, orally, intravenously, intradermally, intranasally or intravaginally. Prior to oral administration, the vaccine can be mixed with a solution containing a sufficient amount of sodium bicarbonate or other suitable compound capable of neutralizing stomach acid (approximately 2 grams). Alternatively, the vaccine, usually in lyophilized form, can be formulated as tablets which are treated with a coating capable of resisting stomach acid.

VIII. Method to Stabilize Platelets

The invention provides a method to stabilize blood platelets. Use of the method allows blood platelets to be stored in the cold, which increases the shelf life of the platelets and reduces bacterial contamination. It is thought that cooling of platelets irreversibly reorganizes the von Willebrand factor receptor [the $(GPIb_{\alpha\beta} IX)_2V$ complex] into clusters on the platelet surface. The integrin receptor $\alpha_M\beta_2$, (complement receptor type 3/Mac-1) of hepatic macrophages recognizes clustered GPIbα, and the macrophages ingest the platelets. The interaction of GPIbα and macrophages can be blocked by galactosylation of exposed β-N-acetylglucosamine (Hoffmeister et al., Science, 301:1531 (2003)).

Accordingly, the method involves utilizing a catalytic domain or polypeptide of the invention to link a donor onto an acceptor that is attached to a platelet. The method of the invention offers an advantage in that the catalytic domains and polypeptides of the invention utilize magnesium instead of manganese during catalysis. Accordingly, the catalytic domains and polypeptides of the invention are active in blood, or in solutions of platelets obtained from blood.

It is thought that numerous donors may be used which will block interaction between GPIbα and macrophages. These donors can be readily determined through use of methods known and described in the art (Hoffmeister et al., Science, 301:1531 (2003)). In a particular embodiment, UDP-galactose is utilized as a donor.

Numerous acceptors are also thought capable of being used to block interaction of GPIbα and macrophages. These acceptors can be readily determined through use of methods known and described in the art (Hoffmeister et al., Science 301:1531 (2003)). In a particular embodiment, β-N-acetylglucosamine is utilized as an acceptor.

In one example, the following method may be used to determine a donor that can be used to stabilize platelets. Platelets can be treated before or after being chilled with a candidate donor and a catalytic domain or polypeptide of the invention. The treated platelets can be incubated with macrophages to determine if treatment with the donor causes the platelets to be resistant to ingestion by the macrophages. Acceptors can be identified by following the above described procedure and then identifying the acceptor onto which a donor was linked to defeat interaction of the platelet with a macrophage.

TABLE I

Exemplary Amino Acid Sequences

| SEQ ID NO | Accession Number | Description | Amino Acid Sequence |
|---|---|---|---|
| 4 | BAA06188 | Human β(1,4)galactosyl-tranferase (398 AA) | MRLREPLLSRSAAMPGASLQRACRLLVAVCA LHLGVTLVYYLAGRDLSRLPQLVGVSTPLQG GSNSAAAIGQSSGDLRTGGARPPPPLGASSQ PRPGGDSSPVVDSGPGPASNLTSVPVPHTTAL SLPACPEESPLLVGPMLIEFNMPVDLELVAKQN NPNVKMGGRYAPRDCVSPHKVAIIIPFRNRQE HLKYWLYYLHPVLQRQQLDYGIYVINQAGDT IFNRAKLLNVGFQEALKDYDYTCFVFSDVDL IPMNDHNAYRCFSQPRHISVAMDKFGFSLPY VQYFGGVSASSKQQFLTINGFPNNYWGWGG EDDDIFNRLVFRGMSISRPNAVVGTCRMIRHS RDKKNEPNPQRFDRIAHTKETMLSDGLNSLT YQVLDVQRYPLYTQITVDIGTPS |
| 5 | A33396 | Mouse β(1,4)galactosyl-transferase (399 AA) | MRFREQFLGGSAAMPGATLQRACRLLVAVC ALHLGVTLVYYLSGRDLSRLPQLVGVSSTLQ GGTNGAAASKQPPGEQRPRGARPPPPLGVSP KPRPGLDSSPGAASGPGLKSNLSSLPVPTTTG LLSLPACPEESPLLVGPMLIDFNIAVDLELLAK KNPEIKTGGRYSPKDCVSPHKVAIIIPFRNRQE HLKYWLYYLHPILQRQQLDYGIYVINQAGDT MFNRAKLLNIGFQEALKDYDYNCFVFSDVDL IPMDDRNAYRCFSQPRHISVAMDKFGFSLPY VQYFGGVSALSKQQFLAINGFPNNYWGWGG EDDDIFNRLVHKGMSISRPNAVVGRCRMIRH SRDKXNEPNPQRFDRIAHTKETMRFDGLNSL TYKVLDVQRYPLYTQITVDIGTPR |
| 6 | S05018 | Bovine β(1,4)galactosyl-transferase (402 AA) | MKFREPLLGGSAAMPGASLQRACRLLVAVC ALHLGVTLVYYLAGRDLRRLPQLVGVHPPLQ GSSHGAAAIGQPSGELRLRGVAPPPPLQNSSK PRSRAPSNLDAYSHPGPGPGPGSNLTSAPVPS TTTRSLTACPEESPLLVGPMLIEFNIPVDLKLIE QQNPKVKLGGRYTPMDCISPHKVAIIILFRNR QEHLKYWLYYLHPMVQRQQLDYGIYVINQA GESMFNRAKLLNVGFKEALKDYDYNCFVFS DVDLIPMNDHNTYRCFSQPRHISVAMDKFGF SLPYVQYFGGVSALSKQQFLSINGFPNNYWG WGGEDDDIYNRLAFRGMSVSRPNAVIGKCR MIRHSRDKKNEPNPQRFDRIAHTKETMLSDG LNSLTYMVLEVQRYPLYTKITVDIGTPS |

TABLE I-continued

Exemplary Amino Acid Sequences

| SEQ ID NO | Accession Number | Description | Amino Acid Sequence |
|---|---|---|---|
| 7 | | Human Stem Region of β(1,4)galactosyl-transferase | RDLSRLPQLVGVSTPLQGGSNSAAAIGQSSGD LRTGGARPPPPLGASSQPRPGGDSSPVVDSGP GPASNLTSVPVPHTTALSLPACPEESPLLVGP MLIEFNMPVDLELVAKQ |
| 8 | | Bovine Stem Region of β(1,4)galactosyl-transferase | RDLRRLPQLVGVHPPLQGSSHGAAAIGQPSG ELRLRGVAPPPPLQNSSKPRSRAPSNLDAYSH PGPGPGPGSNLTSAPVPSTTTR |
| 9 | | Human Catalytic Domain of β(1,4)galactosyl-transferase | SLPACPEESPLLVGPMLIEFNMPVDLELVAKQ NPNVKMGGRYAPRDCVSPHKVAIIIPFRNRQE HLKYWLYYLHPVLQRQQLDYGIYVINQAGD TIFNRAKLLNVGFQEALKDYDTCFVFSDVD LIPMNDHNAYRCFSQPRIHSVAMDKFGFSLP YVQYFGGVSASSKQQFLTINGFPNNYWGWG GEDDDIFNRLVFRGMSISRPNAVVGTCRMIR HSRDKKNEPNPQRFDRIAHTKETMLSDGLNS LTYQVLDVQRYPLYTQITVDIGTPS |
| 10 | | Bovine Catalytic Domain of β(1,4)galactosyl-transferase | SLTACPEESPLLVGPMLIEFNIPVDLKLIEQQ NPKVKLGGRYTPMDCISPHKVAIIILFRNRQEH LKYWLYYLHPMVQRQQLDYGIYVINQAGES MFNRAKLLNVGFKEALKDYDYNCFVFSDVD LIPMNDHNTYRCFSQPRHISVAMDKFGFSLPY VQYFGGVSALSKQQFLSINGFPNNYWGWGG EDDDIYNRLAFRGMSVSRPNAVIGKCRMIRH SRDKKNEPNPQRFDRIAHTKETMLSDGLNSL TYMVLEVQRYPLYTKITVDIGTPS |

TABLE II

| SEQ ID NO | Accession Number | Description | Nucleic Acid Sequence |
|---|---|---|---|
| 11 | D29805 | Human β(1,4)galactosyl-transferase | ATGAGGCTTCGGGAGCCGCTCCTGAGCCGGA GCGCCGCGATGCCAGGCGCGTCCCTACAGCG GGCCTGCCGCCTGCTCGTGGCCGTCTGCGCTC TGCACCTTGGCGTCACCCTCGTTTACTACCTG GCTGGCCGCGACCTGAGCCGCCTGCCCCAAC TGGTCGGAGTCTCCACACCGCTGCAGGGCGG GTCGAACAGTGCCGCCGCCATCGGGCAGTCC TCCGGGGACCTCCGGACCGGAGGGGCCCGGC CGCCGCCTCCTCTAGGCGCCTCCTCCCAGCCG CGCCCGGGTGGCGACTCCAGCCCAGTCGTGG ATTCTGGCCCTGGCCCCGCTAGCAACTTGACC TCGGTCCCAGTGCCCCACACCACCGCACTGTC GCTGCCCGCCTGCCCTGAGGAGTCCCCGCTG CTTGTGGGCCCCATGCTGATTGAGTTTAACAT GCCTGTGGACCTGGAGCTCGTGGCAAAGCAG AACCCAAATGTGAAGATGGGCGGCCGCTATG CCCCCAGGGACTGCGTCTCTCCTCACAAGGT GGCCATCATCATTCCATTCCGCAACCGGCAG GAGCACCTCAAGTACTGGCTATATTATTTGCA CCCAGTCCTGCAGCGCCAGCAGCTGGACTAT GGCATCTATGTTATCAACCAGGCGGGAGACA CTATATTCAATCGTGCTAAGCTCCTCAATGTT GGCTTTCAAGAAGCCTTGAAGGACTATGACT ACACCTGCTTTGTGTTTAGTGACGTGGACCTC ATTCCAATGAATGATCATAATGCGTACAGGT GTTTTTCACAGCCACGGCACATTTCCGTTGCA ATGGATAAGTTTGGATTCAGCCTACCTTATGT TCAGTATTTTGGAGGTGTCTCTGCTTCAAGTA AACAACAGTTTCTAACCATCAATGGATTTCCT AATAATTATTGGGGCTGGGGAGGAGAAGATG ATGACATTTTTAACAGATTAGTTTTTAGAGGC ATGTCTATATCTCGCCCAAATGCTGTGGTCGG GACGTGTCGCATGATCCGCCACTCAAGAGAC AAGAAAAATGAACCCAATCCTCAGAGGTTTG ACCGAATTGCACACACAAAGGAGACAATGCT |

TABLE II-continued

| SEQ ID NO | Accession Number | Description | Nucleic Acid Sequence |
|---|---|---|---|
| | | | CTCTGATGGTTTGAACTCACTCACCTACCAGG TGCTGGATGTACAGAGATACCCATTGTATAC CCAAATCACAGTGGACATCGGGACACCGAGCC TAG |

EXAMPLES

Introduction

β-1,4-Galactosyltransferases (β4Gal-T,1 EC 2.4.1.90/38) are a Golgi resident, type II membrane-bound family of enzymes (β4Gal-T1-T7) that transfer galactose (Gal) in the presence of manganese ion, from UDP-Gal to N-acetylglucosamine (GlcNAc), either free or bound to an oligosaccharide of a glycoprotein or a glycolipid (Brew, K. et al., Proc. Natl. Acad. Sci. USA, 59:491-497 (1968); Takase, K and Ebner K., Curr. Top. Cell Regul. 24:51-62 (1984); Powell, J. T. and Brew, K., J. Biol. Chem., 251:3645-3652 (1976)). The family members exhibit a high level of sequence identity in their catalytic domains (Lo, N. et al., Glycobiology, 8:517-526 (1998); Amado, M. et al. Biochim. Biophys. Acta, 1473:35-53 (1998)). Although they have the same donor sugar specificity, many of these are expected to transfer Gal to different oligosaccharides containing GlcNAc at their nonreducing end. Recent crystallographic studies on β4Gal-T1 have provided detailed information about the structure and function of the enzyme (Gastinel, L. et al., EMBO J., 18:3546-3557 (1999); Ramakrishnan, B. and Qasba, P. K., J. Mol. Biol., 310:205-218 (2001); Ramakrishnan, B. et al., J. Biol. Chem., 276:37665-37671 (2001); Ramakrishnan, B. and Qasba, P. K. J. Biol. Chem. 277:20833-20839 (2002); Ramakrishnan, B. et al., J. Mol. Biol., 318:491-502 (2002); and Ramakrishnan, B. and Qasba, P. K., J. Biomol. Struct. Dyn. 21:1-8 (2003)). These studies have shown that upon substrate binding β4Gal-T1 undergoes conformational changes that involve two loops: a short loop, residues 313-315 containing Trp314, and a longer loop comprising residues 345-365. The conformational changes of these two loops are highly coordinated. Trp314 in the small loop plays a major role in the conformational state of the long loop, in the binding of the substrates, and in the catalytic mechanism of the enzyme (Ramakrishnan, B. et al. J. Biol. Chem., 276: 37665-37671 (2001); Gunasekaran, K. et al., Biochemistry, 42:3674-3687 (2003); Ramasamy, V., J. Mo. Biol., 331:1065-1076 (2003). In the unbound state (open conformation), the side chain of Trp is exposed to the solvent (Gastinel, L. et al., EMBO J. 18:3546-3557 (1999); Ramasamy, V., J. Mo. Biol., 331:1065-1076 (2003)), and the conformation of the long loop is such that the UDP-Gal and the metal binding sites are exposed. Once the substrate binds, the side chain of Trp314 moves into the catalytic pocket to lock the sugar nucleotide in its binding site. Simultaneously, the long loop changes to its closed conformation, masking the sugar nucleotide binding site (Ramakrishnan, B. and Qasba, P. K., J. Mol. Biol., 310: 205-218 (2001), Ramakrishnan, B. and Qasba, P. K., J. Biomol. Struct. Dyn., 21:1-8 (2003), Ramasamy, V., J. Mo. Biol., 331:1065-1076 (2003)). Furthermore, this conformational change in the long flexible loop repositions the amino acid residues at the N-terminal region, creating a metal ion binding site, and at the C-terminal region, creating an oligosaccharide-binding cavity that is also a protein-protein interaction site for R-lactalbumin (LA) (Gastinel, L. et al., EMBO J. 18:3546-3557 (1999), Ramakrishnan, B. and Qasba, P. K., J. Biol. Chem., 277:20833-20839 (2002), Ramakrishnan, B. and Qasba, P. K., J. Biomol. Struct. Dyn. 21:1-8 (2003)). LA is a mammary gland-specific protein that modulates the acceptor specificity of the enzyme toward glucose (Brodbeck, U. et al., J. Biol. Chem., 242:1391-1397 (1967)). LA binds at the extended sugar binding site, present only in the closed conformer of β4Gal-T1, leaving the monosaccharide binding site of the enzyme available for the binding of Glc or GlcNAc. Since LA competes with the oligosaccharide for binding to the extended sugar binding site (Bell, J. E., et al., J. Biol. Chem., 251:3003-3013 (1976); Powell, J. T. and Brew, K., J. Biol. Chem., 251:3653-3663 (1976)), it is very difficult to crystallize β4Gal-T1 in the presence of LA with a bound oligosaccharide acceptor. The wild-type enzyme also does not crystallize in the presence of UDP or UDPhexanolamine, $Mn^{2+}$, and oligosaccharides, thereby restricting structural or biochemical studies on the interactions of oligosaccharides with β4Gal-T1. It has been shown that the sugar moiety of the sugar nucleotide is necessary for efficiently inducing a conformational change in β4Gal-T1 (Geren, C. R., et al., Biochemistry, 14:1461-1463 (1975)).

Of the six ligands that coordinate $Mn^{2+}$, three are from β4Gal-T1: Asp254, Met344, and His347 (Ramakrishnan and Qasba, J. Mol. Biol., 310:205-218 (2001); Ramakrishnan and Qasba, J. Biomol. Struct. Dyn., 21:1-8 (2003); Boeggeman, E. et al., Glycobiology. 12:395-407 (2002)). Residues Met344 and His347, separated by the hinge residue Ile345, are at the N-terminal region of the long flexible loop. The complete metal binding site is created only after His347 has moved during the conformational change to coordinate with the metal ion. To influence the conformational dynamics of the long loop, the residues of the metal binding region were mutated. Mutation of Asp254 or His347 results in either a total or large loss of the enzyme activity, while mutation of Met344 to Ala or Gln results in an only moderate loss of activity (Boeggeman, E. et al., Glycobiology, 12:395-407 (2002)). These studies suggest that Met344 coordination with $Mn^{2+}$ might not be essential for the catalytic activity. To further understand the role of Met344 in the metal binding and conformational change in β4Gal-T1, in the study presented herein it was mutated it to His and it was determined that the mutant M344H-Gal-T1, in the presence of $Mn^{2+}$, has only 1.5% of the wild-type enzyme activity. On the other hand, the mutant M344H-Gal-T1 exhibits 25% of its catalytic activity in the presence of an alkali metal ion, $Mg^{2+}$. In contrast, $Mg^{2+}$ does not activate the wild-type enzyme. Although metal ions $Mg^{2+}$ and $Mn^{2+}$ bind to the mutant M344H-Gal-T1, their enzyme kinetics are different, indicating that the residue at position 344 and the appropriate metal ion play an important role in the conformational dynamics of the long loop in the catalytic mech anism of β4Gal-T1.

In the presence of $Mn^{2+}$ and UDP-Gal, or UDP-hexanolamine, the mutant M344H-Gal-T1 crystallizes in the closed conformation. This has enabled the crystallize the mutant in complex with chitobiose, in the presence of $Mn^{2+}$ and UDP-hexanolamine. In the crystal structure of the complex with chitobiose, the GlcNAc residue at the reducing end of the disaccharide binds to β4Gal-T1 in a manner similar to that of GlcNAc bound in the LS-GlcNAc complex (Ramakrishnan, B. and Qasba, P., *J. Mol. Biol.* 310:205-218 (2001); Ramakrishnan and Qasba, *J. Biomol. Struct. Dyn.*, 21:1-8 (2003)). The second nonreducing end GlcNAc residue of the disaccharide forms extensive hydrophobic interactions with the highly conserved Tyr286 residue.

Example 1

Site-Directed Mutagenesis

Site-directed mutagenesis was performed using the polymerase chain reaction (PCR) method. Construction of the mutants was done using plasmid pEGT-d129 as the template. The pEGT-d129 plasmid contains a BamH I/EcoR I fragment inserted into a pET23a Novagen, Madison, Wis.) vector that codes for residues 130 to 402 of bovine Gal-T1 (Boeggeman et al., *Protein Eng.*, 6:779 (1993)), and has a Cysteine to Threonine exchange at the 342 amino acid residue position (C342T).

The nucleic acid sequences of the primers corresponding to the upper DNA strand that were used to create the M344H and M344E mutations are: M344H: 5'ATCGGGAAG ACGCGTCACATCCGCCACTCGAGAGAC-3' (SEQ ID NO: 12), and M344E:5'ATCGGGAAG ACGCGTGAGATCCGCCACTCGAGAGAC-3' (SEQ ID NO: 13). The restriction site Mlu I is underlined and the mutation codon in bold italics. Typically, the Gal-T1 DNA fragment between Mlu I to EcoR I was PCR-amplified using the terminal cloning primer and the mutagenesis primer. The fragment was cut with the restriction enzymes Mlu I and EcoR I and ligated with the precut plasmid pEGT-129 DNA with the same enzymes. Mutants were screened for the presence of full Gal-T1 DNA, and then sequenced. The positive clones were transformed into BL21(DE3) pLysS cells as described previously (Ramakrishnan et al., *J. Mol. Biol.*, 310: 205 (2001)). The mutant proteins were expressed and purified according to the published method (Ramakrishnan et al., *J. Mol. Biol.*, 310:205 (2001)).

The role of the Met344 residue in the structure and function of β4Gal-T1 was investigated by mutating it to a histidine or glutamic acid residue. These amino acids were chosen to retain the coordination bond with the primary metal ion. Substitution of Met344 with Ala or Gln would have eliminated the coordination bond (Boeggeman and Qasba, *Glycobiology* 12:395 (2002)).

Example 2

Protein Expression and Purification

For protein expression BL21 (λDE3)/pLysS-competent cells were transformed with the pET vector derivatives according to the manufacturer's protocols. The transformed cells were grown in LB broth containing 50 µg/ml$^{-1}$ ampicillin to an OD600 nm of about 0.7, followed by induction with 0.4 mM IPTG. Cultures were harvested after 3-4 hours by centrifugation at 2000×g for 20 minutes. The inclusion bodies were isolated and solubilized as described (Boeggeman et al., *Protein Eng.*, 6:779-785 (1993)). From a liter of induced bacterial culture, the yield is generally 80 to 100 mg of purified inclusion bodies. Novex gels were used for SDS-PAGE analysis and the protein bands were visualized with Coomassie blue. Protein concentrations were measured with the Bio-Rad protein dye reagent with bovine serum albumin as the standard.

An S-sulfanation protocol was used for folding the protein obtained from the inclusion bodies (Boeggeman et al., *Protein Eng.*, 6:779-785 (1993)). Inclusion bodies (100 mg) were dissolved in 10 ml of 5 M guanidine hydrochloride (Gu-HCl) with 0.3 M sodium sulfite at room temperature. To sulfonate all of the free thiol groups in the protein molecule, 1 ml of 50 mM S-sulfonating agent 2-nitro-5-(sulfothio)-benzoate (NTSB) was added to the solution and stirred vigorously. Completion of sulfonation was judged by the color change of the solution from red to pale yellow. The protein solution was then diluted tenfold with water to precipitate the sulfonated protein. The sulfonated protein was re-dissolved in 5 M Gu-HCl to a protein concentration of 1 mg/ml, which has an absorption of 1.9 to 2.0 at 275 nm. The protein solution was diluted tenfold in 10 ml portions in a folding solution to give a final concentration of 100 µg/1 ml, 0.5 M Gu-HCl, 50 mM Tris-HCl (pH 8.0 at 4° C.), 5 mM EDTA, 4 mM cysteamine, and 2 mM cystamine. The protein was allowed to fold for 48 hours at 4° C. and was then dialyzed against three 4 liter changes of 50 mM Tris-HCl (pH 8.0), 5 mM EDTA, 4 mM cysteamine, 2 mM cystamine at 4° C. to remove Gu-HCl. The protein that precipitated during dialysis was removed by centrifugation and the supernatant was concentrated. Typically when 100 mg of sulfonated wild-type d129-B4GalT1 is folding in a 1 liter folding solution, it yields 3 to 5 mg of active, soluble, and pure protein. The folded active B4GalT-1 was further purified by affinity chromatography using an LA-agarose column.

Example 3

4Gal-T Enzyme Assays

Protein concentrations were measured using the Bio-Rad Protein Assay kit, based on the method of Bradford and further verified on SDS-PAGE gels using standard protein concentration markers. An in vitro assay procedure for Gal-T1 has been reported previously (Ramakrishnan et al., *J. Mol. Biol.*, 310:205 (2001)). The activities were measured using UDP-Gal as sugar nucleotide donor, and GlcNAc as the acceptor sugar. For the specific activity measurements, a 100 µL incubation mixture containing 25 mM GlcNAc, 5 mM MnCl$_2$ or MgCl$_2$, 20 mM Tris-HCl pH 8.0, 500 µM UDP-Gal, 500 ng M344H-Gal-T1 or 30 ng of C342T-Gal-T1 and 0.5 µCi $^3$H-UDP-Gal was used for each Gal-T reaction. The incubation was carried out at 30° C. for 15 minutes. The reaction was terminated by adding of 200 µl cold water, and the mixture was passed through a 0.5 mL bed volume column of AG 1-X8 cat ion resin (Bio-Rad) to remove any unreacted $^3$H-UDP-Gal. The column was washed successively with 300, 400 and 500 µl of cold water, and the column flow-through was diluted with Biosafe scintillation fluid; radioactivity was measured with a Beckman counter. A reaction without the acceptor sugar was used as a control. Only 0.1 mM concentration of ZnCl$_2$ or CoCl$_2$ was used whenever Zn$^{2+}$ or Co$^{2+}$ was used during the enzyme assay.

Previous studies have shown that ions of alkaline earth metals, such as Mg$^{2+}$, Ca$^{2+}$ or Sr$^{2+}$, do not activate the wild-type β4Gal-T1 as they do not bind to the primary metal binding site of the enzyme (Powell and Brew, *J. Biol. Chem.*, 251:3645 (1976); Boeggeman and Qasba, *Glycobiology*, 12:395 (2002)). When various Met344 mutants were tested for their catalytic activity in the presence of several metal ions, including alkaline earth metals, they showed metal ion activation specificities different from the wild-type β4Gal-T1 (Table III).

TABLE III

Catalytic Activity (picomoles per minute per nanogram) in the Presence of Various Metal Ions[a]

| metal | wild-type β4Gal-T1 | M344H | M344E | M344A | M344S | M344Q |
|---|---|---|---|---|---|---|
| Mn | 5.35 | 0.13[c] | 0.32 | 4.16 | 1.97 | 1.91 |
| Co | 0.41[b] | 0.02 | 0.24 | 0.61[b] | 0.41 | 0.80[b] |
| Zn | 1.42 | 0.08 | 0.27 | 0.64 | 0.40 | 0.71 |
| Mg | 0 | 1.42 | 0 | 0 | 0 | 0 |
| Ca | 0 | 0.06 | 0.01 | 0 | 0 | 0 |
| Sr | 0 | 0.01 | 0.02 | 0 | 0 | 0 |

[a]All assays were carried out at 500 μM UDP-Gal, 25 mM GlcNAc, and 5 mM metal ion, except for $Co^{2+}$ and $Zn^{2+}$, which were used at concentrations of 0.1 mM.
[b]At 200 μM UDP-Gal, 25 mM GlcNAc, and 0.1 mM $Co^{2+}$, the specific activities of the wild type and mutants M344A and M344Q are 0.65, 0.55, and 0.4 pmol $min^{-1}$ $ng^{-1}$, respectively.
[c]M344H was assessed at 3 mM GlcNAc since, at higher concentrations, its catalytic activity is inhibited in the presence of $Mn^{2+}$.

Surprisingly, the catalytic activity for the M344H-Gal-T1 mutant is better with the $Mg^{2+}$ than with the $Mn^{2+}$, preferred by the native enzyme. Although its specific activity using manganese ion is low compared to the wild type, its activity in the presence of the $Mg^{2+}$ is nearly one-fourth of the wild type with the $Mn^{2+}$. This value is similar to that of the wild-type enzyme in the presence of $Zn^{2+}$. Although the mutant M344E-Gal-T1 exhibits low levels of enzyme activity in the presence of $Mn^{2+}$, $Co^{2+}$ or $Zn^{2+}$, the activity with each was similar to the maximum activity observed at 100 μM concentrations of the metal ions (Table III). Similar to the behavior of the wild-type enzyme, higher concentrations of $Co^{2+}$ and $Zn^{2+}$ inhibit the activity of M344E-Gal-T1, whereas manganese does not exhibit this effect.

Figure 1B:
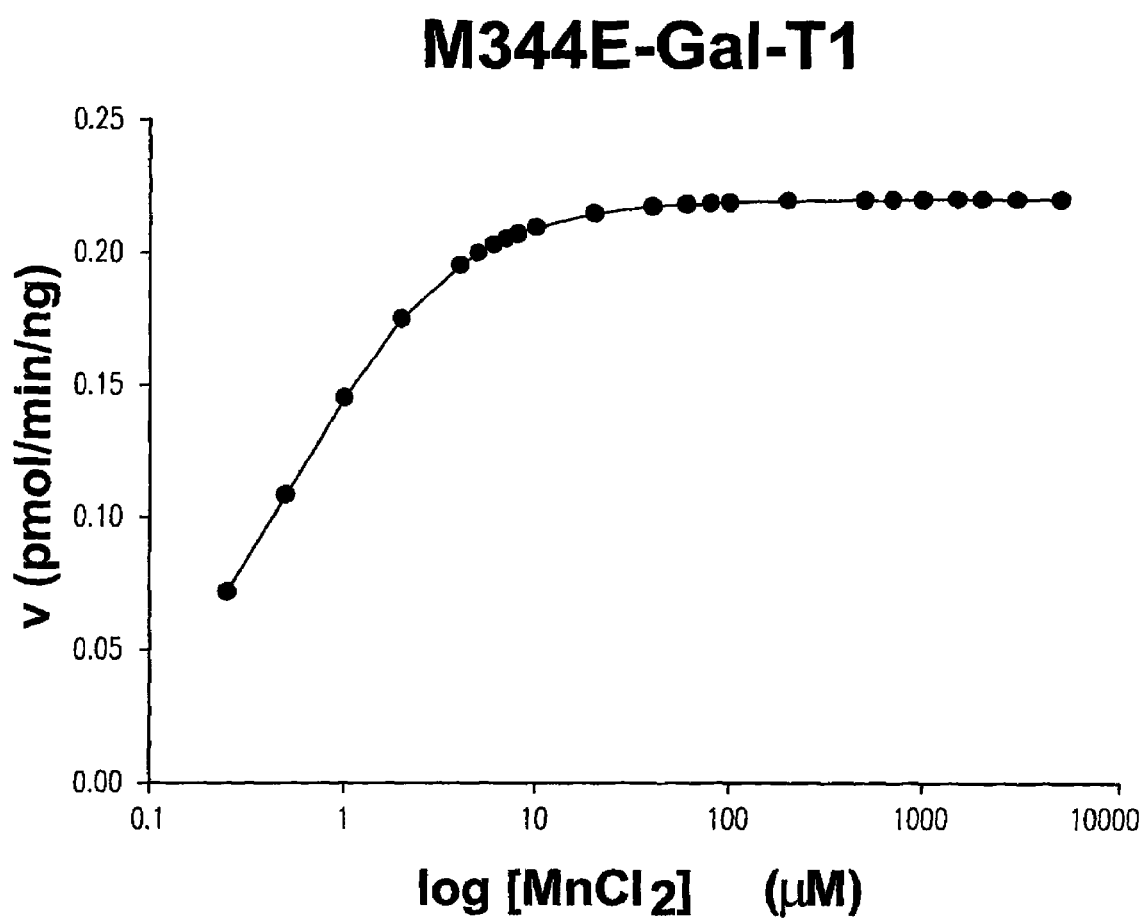
FIG. 1B illustrates a metal ion activation curve of the M344E-Gal-T1 mutant enzyme in the presence of $Mn^{2+}$ where the metal ion concentration is plotted on a log scale.
Figure 1C:
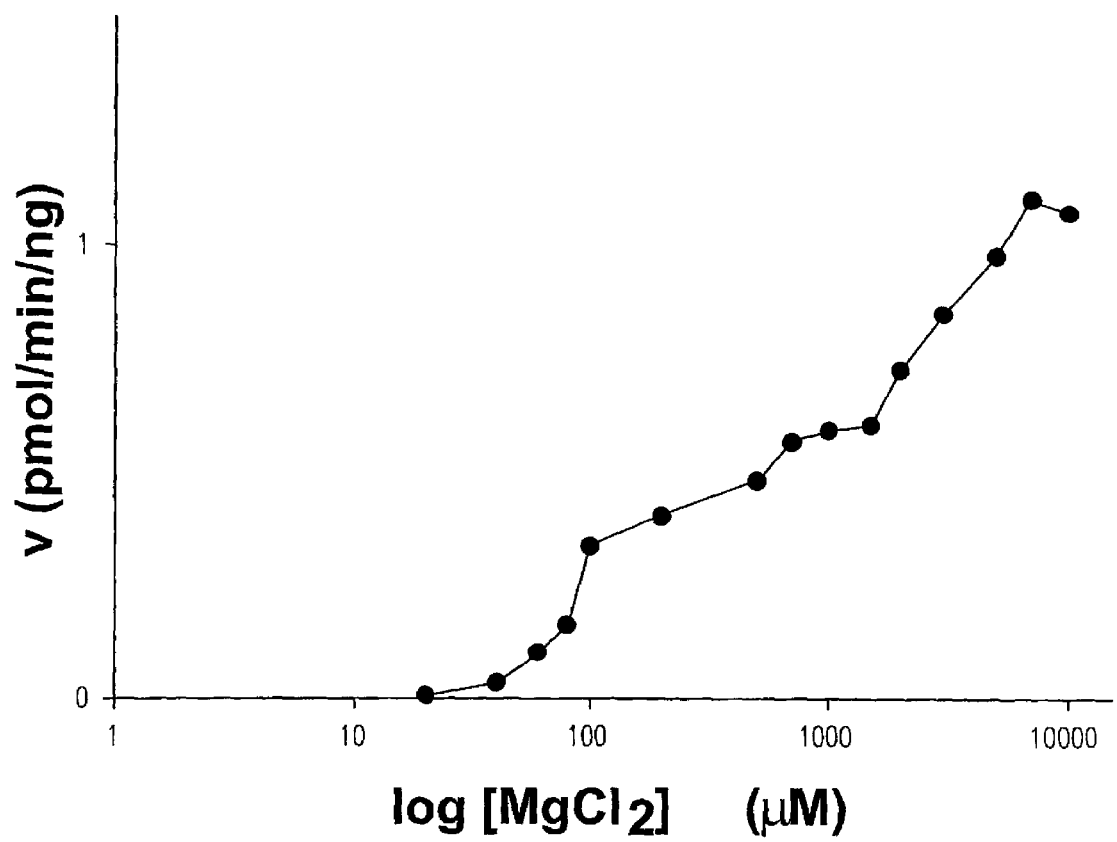
FIG. 1C illustrates a metal ion activation curve of the M344H-Gal-T1 mutant enzyme in the presence of $Mg^{2+}$ where the metal ion concentration is plotted on a log scale.

The activation curve of M344E-Gal-T1, using $Mn^{2+}$, is strikingly different from that of the wild-type enzyme (FIGS. 1A and 1B). In contrast to the wild type enzyme, the velocity curve obtained with the $Mn^{2+}$ concentration for the M344E-Gal-T1 mutant is not sigmoidal. On the other hand, the same curve for the M344H-Gal-T1 mutant in the presence of the $Mg^{2+}$ is sigmoidal (FIG. 1C). The observation that activation of the wild type enzyme by metal ions is sigmoidal has been interpreted as involving two metal binding sites in the enzyme: one with high affinity ($K_{d1}$), which is associated with low velocity, and a second site with low affinity ($K_{d2}$), which is associated with high velocity (Powell and Brew, J. Biol. Chem., 251:3645 (1976); Boeggeman and Qasba, Glycobiology, 12:395 (2002)). A similar sigmoidal velocity curve for the M344H-Gal-T1 mutant with $Mg^{2+}$ is also suggestive of two metal binding sites, with $Mg^{2+}$ binding not only to the first site but also to the second metal binding site. The values of the dissociation constant ($K_d$) for $Mn^{2+}$ of the mutant are quite different from that of the wild type (Table IV).

TABLE IV

Kinetic Parameters of the Substrates[a]

| ligand | parameter | wild-type β4Gal-T1 with $Mn^{2+}$ | M344H-Gal-T1 with $Mn^{2+}$ | M344H-Gal-T1 with $Mg^{2+}$ |
|---|---|---|---|---|
| metal ion | $K_{d1}$ (mM) | 0.030(4) | 0.0014(10) | 0.16(8) |
|  | $K_{d2}$ (mM) | 0.40(9) | 45(10) | 6.2(3) |
| UDP-Gal | $V_{max}$ (pmol $min^{-1}$ $ng^{-1}$) | 6.4(4) | 0.170(5) | 2.6(1) |
| GlcNAc | $K_{cat}$ ($s^{-1}$) | 3.6 | 0.097 | 1.44 |
|  | $K_{ia}$ | 0 | 0 | 0 |
|  | $K_A$ (μM) | 95(6) | 7(2) | 512(24) |
|  | $K_{cat}/K_A$ ($s^{-1}$ $μM^{-1}$) | 0.04 | 0.015 | 0.003 |
|  | $K_B$ (nM) | 10(1) | 0.75(6) | 25(3) |
|  | $K_{cat}/K_B$ ($s^{-1}$ $mM^{-1}$) | 0.36 | 0.13 | 0.058 |

[a]The $K_{d1}$ and $K_{d2}$ values for the metal ions were derived from FIG. 1. Standard deviations are given in the parentheses to their least significant decimal point.

The $K_{d1}$ value for $Mn^{2+}$ for the mutant is 25-fold lower than that of the wild-type enzyme, suggesting that the $Mn^{2+}$ binds tightly to the primary metal binding site of the mutant. However, the d2 for the mutant is 100-fold higher than that of the wild type, indicating that $Mn^{2+}$ binds weakly to the second metal binding site of the mutant. The binding constants for $Mn^{2+}$ binding by the mutant are only moderately high. The $K_d$ values for the binding of $Mg^{2+}$ to sites I and II are 100- and 7-fold higher, respectively, than those for binding $Mn^{2+}$ to the same mutant (Table IV), indicating that $Mg^{2+}$ compared to $Mn^{2+}$ binds weakly to the primary binding site of the mutant. Since the M344E-Gal-T1 mutant exhibits a non-sigmoidal activation curve (FIG. 1B), a single metal binding site model was used for calculating the kinetic constants. The binding constant $K_1$ for this site is 0.5 μM, fifty-fold lower than the binding to the primary site of the wild type, indicating that the $Mn^{2+}$ binds very tightly to the primary binding site of M344E-Gal-T1.

The metal ion activation curves indicate that mutation of Met344, the residue in the primary metal binding site of the wild type enzyme, affects the secondary metal binding site strongly. To understand the effect, the crystal structure analysis of the M344H-Gal-T1 mutant together with enzyme kinetics, in the presence of $Mg^{2+}$, was analyzed.

$Mn^{2+}$ at higher GlcNAc concentrations inhibits the catalytic activity of the mutant. This effect was not observed with $Mg^{2+}$. In comparison, noncompetitive inhibition was observed at high GlcNAc concentrations with the wild-type enzyme (Morrison and Ebner, J. Biol. Chem., 246:3977 (1971)).

In the presence of $Mn^{2+}$, inhibition of the catalytic activity of the M344H-Gal-T1 mutant was observed at GlcNAc concentrations of 3 to 7 mM, whereas only much higher GlcNAc concentrations are known to inhibit the catalytic activity of the wild-type enzyme (Morrison and Ebner, J. Biol. Chem., 246:3977 (1971)). Under the same measurement conditions, the catalytic activity of the mutant M344H-Gal-T1 was not inhibited due to the increased GlcNAc concentration in the presence of $Mn^{2+}$. Inhibition at excess acceptor concentrations has been shown to result from formation of a dead-end enzyme.$Mn^{2+}$.UDP.acceptor complex (Bell et al., J. Biol. Chem., 251:3003 (1976)). In this step the metal ion plays an important role which can be described on the basis of the conformational flexibility of the mutant in the presence of different metal ions.

During the catalytic cycle, upon binding of the metal ion and UDP-Gal, β4Gal-T1 undergoes a conformational change from an open to a closed structure. In the open confirmation the long loop is placed in such a way that its His347 residue is away from the metal binding site. In the closed conformation, the His residue forms a strong coordination bond with the metal ion. This creates the acceptor-binding site of the enzyme. After catalysis and product release, the closed conformation reverts to the open conformation which exposes the UDP and metal ion to the solvent environment and starts a new cycle.

Figure 6:
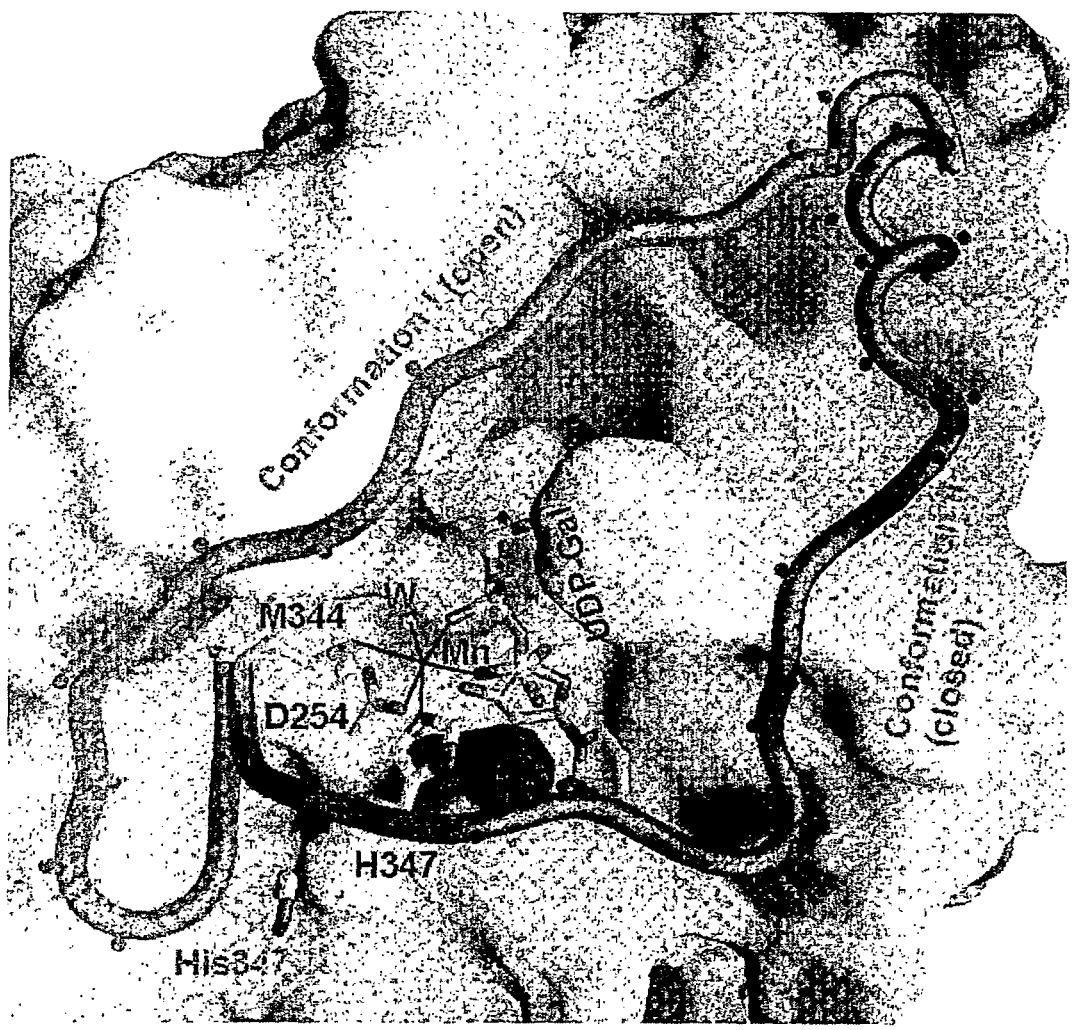
FIG. 6 shows a comparison of the conformation of the long loop region of the open and closed structures of the wild-type β4Gal-T1 (PDB: 1FGX, 1O0R). The electrostatic surface diagram of the portion of the enzyme molecule is shown except for the long loop residues 345 to 365. The negatively charged surface regions are indicated by light coloration, while the positively charged surface regions are indicated by darker coloration. The left-most tube corresponds to open conformation of the long loop, while the right-most tube is to the closed conformation.

The primary metal binding site is situated at the N-terminal hinge region of the long loop, whereas the metal binding residues, Met344 and His347, flank the hinge residue Ile345 (FIG. 6). Since His347 can coordinate with the metal ion only when β4Gal-T1 is in the closed conformation (Ramakrishnan and Qasba, *J. Mol. Biol.* 310:205 (2001)), the metal ion coordination with β4Gal-T1 changes during the catalytic cycle. In the open conformation, the metal ion has only two coordination bonds with the residues of β4Gal-T1, one with Asp254 and the other with Met344. Of these, the coordination with Met344 being weak, the product UDP and $Mn^{2+}$ are easily released.

In contrast, in the M344H-Gal-T1 mutant, the metal ion may not be released as easily as in the wild-type enzyme due to stronger coordination of $Mn^{2+}$ with the His residue. This "sticky" $Mn^{2+}$ may not only hinder the release of UDP, but may also facilitate binding of GlcNAc in the absence of UDP-Gal. Inhibition by the acceptor, even at low concentrations, may have been due to this effect. Since $Mn^{2+}$ is a less preferred metal ion than $Mn^{2+}$ for coordination with the His residue, this "sticky" effect may be absent. These results show that the metal ion plays a role in determining the $k_{cat}$ of the enzyme reaction by participating in the conformational cycling of the enzyme, as well as in the formation and stabilization of the transition state complex during catalysis.

The observation of a sigmoidal curve (FIG. 1C) for the activation of the M344H-Gal-T1 mutant by $Mg^{2+}$ can be explained by the presence of two metal binding sites. However, other factors that may also contribute to the enhanced activity at high metal concentrations. At the end of the catalytic cycle, in order to release the bound UDP and $Mg^{2+}$, the enzyme has to change to an open conformation. At this stage, the faster it releases UDP, the sooner it attains the open conformation to start a new catalytic cycle. Since UDP has a strong affinity for a metal ion, the free metal ion concentration has to be sufficiently high enough to efficiently release the bound UDP from the enzyme.$Mn^{2+}$.UDP complex. In the enzyme.$Mg^{2+}$.UDP complex of the mutant, $Mg^{2+}$ is most suitable metal ion to dislodge the bound UDP molecule. In the wild-type enzyme, a relatively high concentration of $Mn^{2+}$ enables the faster release of UDP from the enzyme. A similar mechanism may be responsible for the enhanced catalytic activity in the presence of various cations such as spermine and spermidine at low concentrations of $Mn^{2+}$ Baker and Hillegass, *Arch. Biochem. Biophys.*, 165:597 (1974); Navaratnam et al., *Biochem. Jour.*, 239:423 (1986)).

Example 4

Determination of Kinetic Constants

The enzyme activation data at various concentrations of $Mg^{2+}$ were fitted to an equation describing metal binding to a high affinity site ($K_1$) to generate an enzyme form with a low $k_{cat}$ ($V_1$) and to a second, lower affinity site ($K_2$) to generate a form with a higher $k_{cat}$ ($V_2$) (Boeggeman and Qasba, *Glycobiology*, 12:395 (2002)):

$$v = \frac{[Mg](V_1 * K_2 + V_2 * [Mg])}{(K_1 * K_2 + K_2 * [Mg] + [Mg] * [Mg])}$$

The true $K_m$ of the donor ($K_A$) and of the acceptor ($K_B$), the dissociation constant of the donor, $K_{ia}$, and $k_{cat}$, were obtained using two-substrate analyses and the primary plots of at least five concentrations of donor (UDP-Gal) and five concentrations of acceptor, and the corresponding secondary plots of the intercepts and slopes. Initial rate conditions were linear with respect to time. A suitable range of donor and acceptor concentrations was chosen, which allowed accurate Michaelis-Menten constants to be derived. The data were also analyzed for a general two-substrate system using the following equations (Herbert, Initial Rate Enzymatic Kinetics, Springer-Verlag, New York (1975)) with the software EnzFitter, a Biosoft non-linear curve fitting program for Windows:

$$v = \frac{V_{max}[A][B]}{K_{ia}K_B + K_B[A] + K_A[B] + [A][B]} \quad \text{Equation 1}$$

$$v = \frac{V_{max}[A][B]}{K_B[A] + K_A[B] + [A][B]} \quad \text{Equation 2}$$

Here v is the initial velocity and the rate equation for a sequential symmetrical, initial velocity pattern associated with equation 1, an ordered or random equilibrium mechanism in which substrate A dissociates well from the ECS complex with a dissociation constant of $K_{ia}$. Equation 2 is for an asymmetric initial velocity pattern for a double-displacement or "ping-pong" mechanism. The kinetic parameters $K_A$, $K_B$, $K_{ia}$, and $V_{max}$ were obtained from the fitted curves using the above rate equations. The graphical method and EnzFitter program gave very similar kinetic parameters. In the β4Gal-T assay, the maximum substrate concentrations used for UDP-Gal and GlcNAc were 0.2 mM and 25 mM, respectively (which are threefold higher than their $K_m$ values).

Figure 2A:
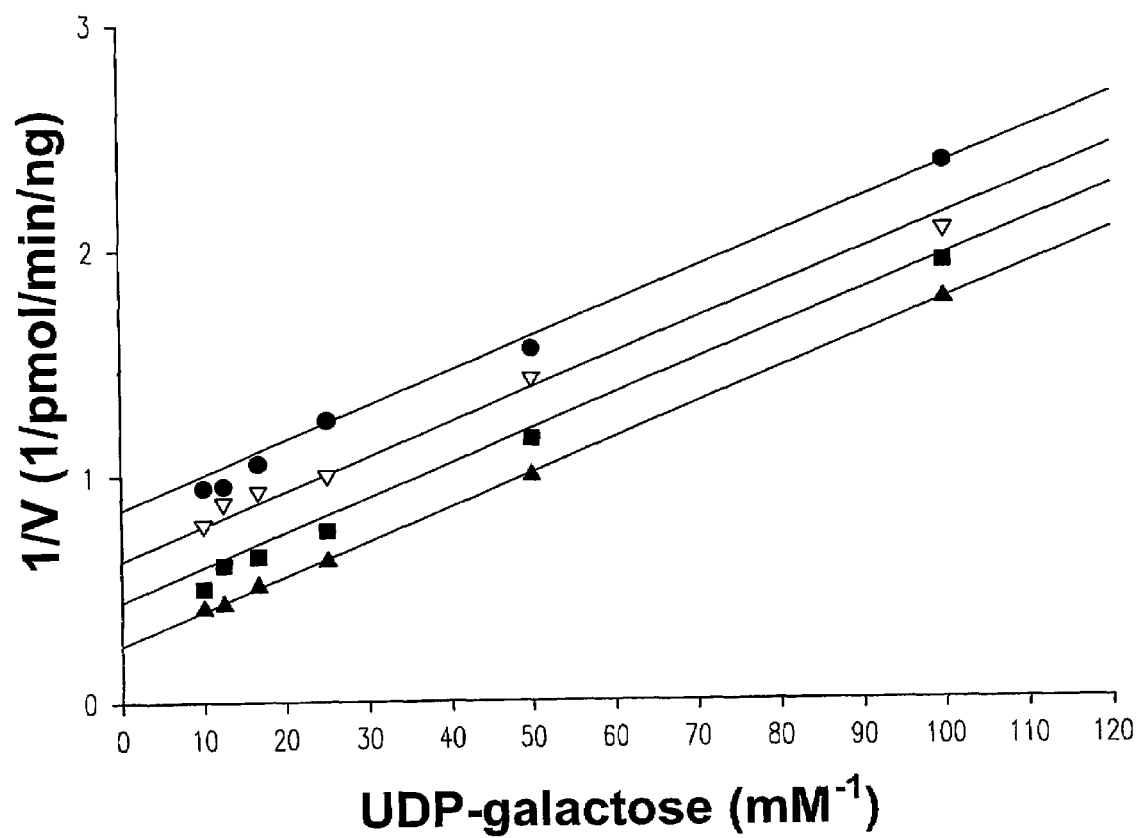
FIG. 2A is a double-reciprocal plot for galactose transfer to GlcNAc catalyzed by C342T-Gal-T1. UDP-galactose concentrations are plotted as the variable substrate at the following fixed concentrations of GlcNAc: Solid circle, 2 mM; inverted open triangle, 3 mM; solid square, 5 mM; solid triangle, 20 mM.
Figure 2B:
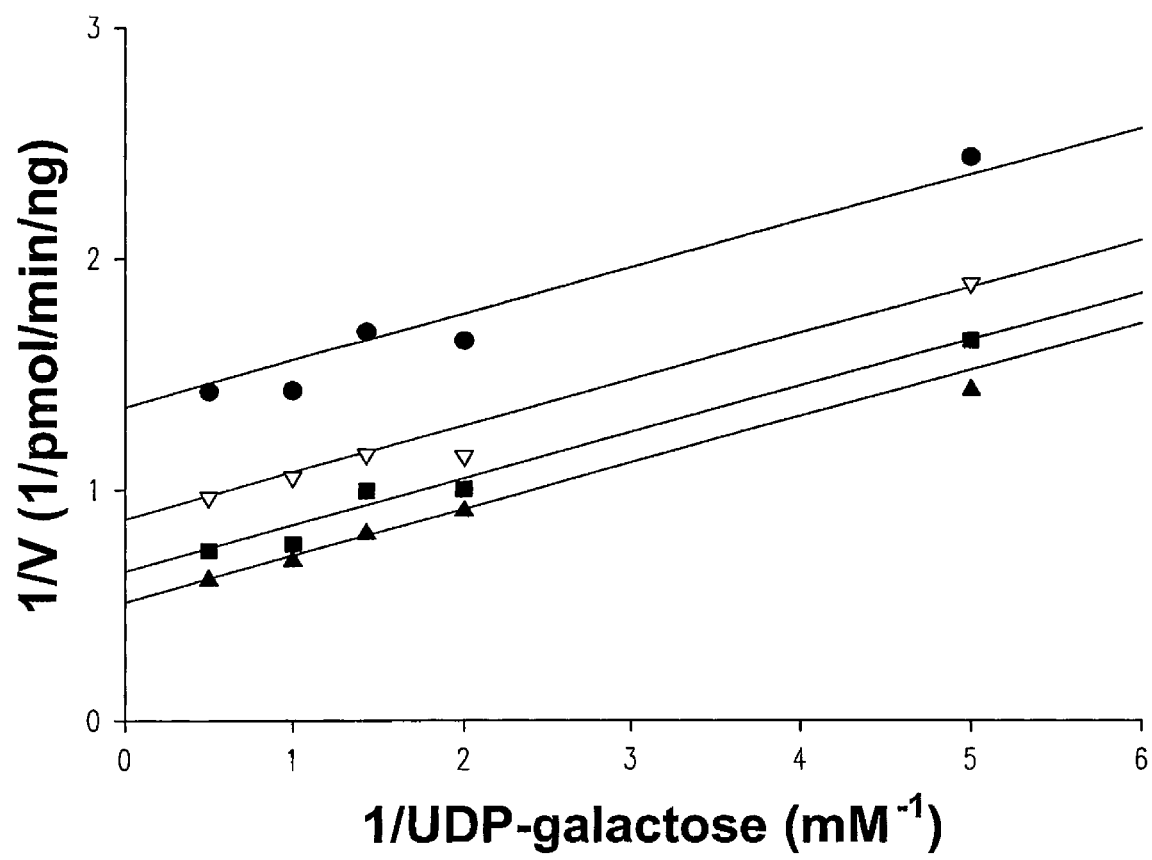
FIG. 2B is a double-reciprocal plot for galactose transfer to GlcNAc catalyzed by M344H-Gal-T1. UDP-galactose concentrations are plotted as the variable substrate at the following fixed concentrations of GlcNAc: Solid circle, 10 mM; inverted open triangle, 20 mM; solid square, 40 mM; solid triangle, 80 mM.

Since M344H-Gal-T1 exhibits high catalytic activity in the presence of $Mg^{2+}$, a double substrate kinetic study was carried out in order to determine the kinetic constants for both the donor (UDP-Gal) and acceptor (GlcNAc) molecules in the presence of the $Mn^{2+}$ and compared with those of the wild-type enzyme in the presence of the $Mn^{2+}$ (FIGS. 2A and 2B). The kinetic data fits best to a rate equation that lacks a $K_{ia}$ term Equation 2), describing an asymmetric initial velocity pattern associated with a sequential or "ping-pong" mechanism in which donor substrate does not dissociate from the enzyme-substrate complex. This is quite similar to that of the wild-type enzyme (FIG. 2B) (Takase and Ebner, *Curr. Top. Cell Regul.*, 24:51 (1984); Boeggeman and Qasba, *Glycobiology*, 12:395 (2002)). In the β4Gal-T reaction the true $K_m$ value for the acceptor and donor for the mutant are nearly two- and fivefold higher, respectively, than the wild-type β4Gal-T1 (Table IV). Although the catalytic efficiency with respect to donor and acceptor, compared to the wild-type enzyme with $Mn^{2+}$, has decreased by an order of about 13 and 6, respectively, the turnover number of the mutant, $k_{cat}$, is reduced by only 60%. The lesser effect on $k_{cat}$ could be the result of $Mg^{2+}$ participating more efficiently in the formation of the transition state complex during the transfer reaction by the mutant or minor differences in the coordination geometry of the $Mg^{2+}$ in the mutant compared to that of $Mn^{2+}$ ion in the wild-type enzyme. The crystal structure of the M344H-Gal-T1 in complex with UDP-Gal in the presence of either $Mn^{2+}$ or $Mg^{2+}$ was then determined and compared to the structure with the wild-type UDP-Gal.metal complex. Crystal structure analysis of the M344E-Gal-T1 mutant in the presence of UDP-Gal and $Mn^{2+}$ was conducted to further understand the effect of the M344E mutation on the metal-ion binding site.

Example 5

Crystal Structure Determination

The mutant M344H-Gal-T1 was co-crystallized in the presence of UDP-Gal and MnCl$_2$ or MgCl$_2$, while the M344E-Gal-T1 mutant was crystallized in the presence of UDP-Gal and MnCl$_2$. The crystals were grown at room temperature by the hanging drop method, using 30 mg/mL of the mutant protein, 17 mM of UDP-Gal, and 17 mM MgCl$_2$ or MnCl$_2$, with the precipitant containing 10% (v/v) dioxane, 100 mM mes-NaOH buffer (pH 6.5) and 2.0 M ammonium sulfate. Complete three-dimensional x-ray diffraction data were collected at beam line X9B, NSLS, Brookhaven National Laboratory (Upton, N.Y.), using a Quantum-4 ccd detector. The frames were processed using HKL2000 (Otwinowski and Minor, *Methods Enzymol.*, 276:307 (1997)).

Since the crystals were isomorphous with the C342T-Gal-T1.UDP-Gal.Mn$^{2+}$ complex crystals, that structure was used as a starting model without any substrate. An initial model containing Ala at residue 344 was used. After initial refinement, the difference Fourier electron density maps not only confirmed the mutation, but also revealed the UDP-Gal and Mn$^{2+}$ or Mg$^{2+}$ bound to the enzyme. These features were included in the further refinement. All the refinements were carried out with CNS version 1.0 (Brunger at al., *Acta Crystallogr.*, D54:905 (1998)). All figures were drawn using graphic programs MOLSCRIPT (Karulis, *J. Appl. Crystallogr.*, 24:946 (1991)), BOBSCRIPT (Esnouf, *Acta Crystallogr.* D55:938 (1999)), and Grasp (Nicholls et al., *Proteins*, 11:281 (1991)). The coordinates have been deposited in the Protein Data Bank.

Figure 3A:
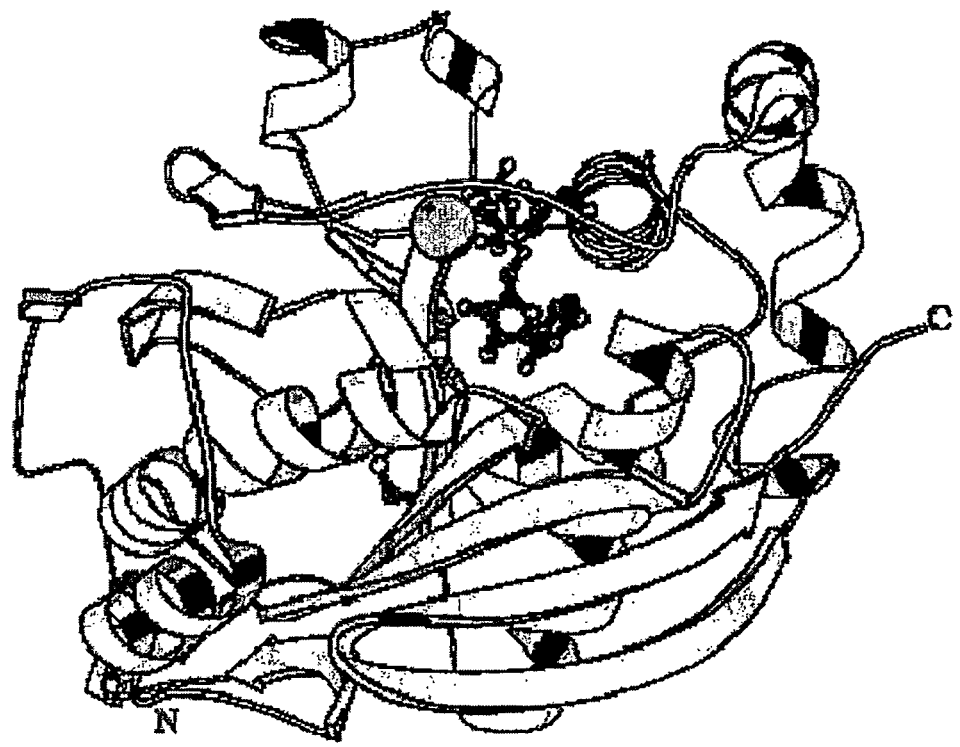
FIG. 3A illustrates the overall crystal structure of the M344H-Gal-T1 mutant in the presence of UDP-Gal and $Mg^{2+}$. The metal ion is shown as a sphere and the UDP-Gal molecule in ball-and-stick model.

The wild-type β4Gal-T1 crystallized in the presence of UDP-Gal and MnCl$_2$, while the M344-Gal-T1 mutants crystallized in the presence of UDP-Gal with either MnCl$_2$ or MgCl$_2$. The crystal structure of both mutants was determined, M344E-Gal-T1 in the complex with UDP-Gal and Mn$^{2+}$, and M344H-Gal-T1 in complex with UDP-Gal and Mn$^{2+}$ or Mg$^{2+}$. The three-dimensional crystal structures of these complexes are quite similar. The β4Gal-T1 mutant proteins were found in the closed conformation (FIG. 3A), similar to the wild-type complex with UDP-Gal.Mn$^{2+}$ (PDB: 1O0R) (Ramakrishnan et al., *J. Mol. Biol.*, 318:491 (2002); Ramakrishnan and Qasba, *J. Biomol. Struct. Dyb.*, 21:1 (2003)). The r.m.s. deviations between these structures and the closed structure of the wild-type β4Gal-T1 varies between 0.5 and 0.6 Å on the Cα atoms, indicating that neither the mutation nor the binding of Mg$^{2+}$ caused any significant change in the structure.

Figure 3B:
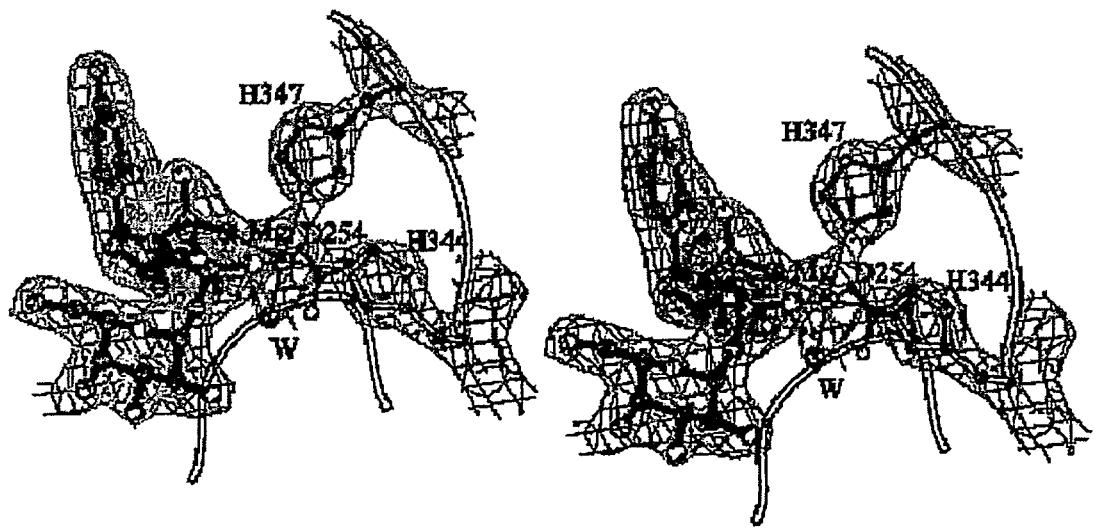
FIG. 3B is a stereo view of the final electron density maps contoured at $1.5\sigma$ level around the UDP-Gal molecule and $Mg^{2+}$ in the crystal structure of the M344H-Gal-T1-UDP-Gal $Mg^{2}$ complex. Coordination of a magnesium ion is shown to be similar to that of a manganese ion, which includes the sixth coordination with a water molecule.

The metal nucleotide complex can be clearly located in the crystal structure of the M344H-Gal-T1.UDP-Gal.Mg$^{2+}$ complex (FIG. 3B). Furthermore, in the crystal structures of M344H-Gal-T1.UDP-Gal.metal complexes, the presence of the different metal ions could easily be identified from the difference Fourier maps. When the difference Fourier electron density at the metal ion position was compared with the electron densities of the phosphate groups of UDP-Gal in M344H-Gal-T1.UDP-Gal.Mn$^{2+}$, the electron density at the metal ion position was stronger than at the phosphate groups of UDP-Gal. In M344H-Gal-T1.UDP-Gal.Mg$^{2+}$, the electron density at the metal ion position was weaker than at the phosphate groups. In these structures the metal ions exhibit six similar coordination bonds with comparable bond distances (Table V). The stereochemistry of the Mg$^{2+}$ coordination is quite similar to that of the Mn$^{2+}$ (Ramakrishnan et al., *J. Mol. Biol.* 318:491 (2002); Ramakrishnan et al., *J. Biomol. Struct. Dyn.*, 21:1 (2003)).

TABLE V

| | Metal Ion Coordination Distances (angstroms) | | | | |
|---|---|---|---|---|---|
| coordination | Mn$^{2+}$ in M344H-Gal-T1•UDP-Gal-Mn$^{2+}$ | | Mg$^{2+}$ in M344H-Gal-T1•UDP-Gal-Mg$^{2+}$ | | Mn$^{2+}$ in wild-type Gal-T1•UDP-Gal•Mn$^{2+}$ |
| residue | molecule 1 | molecule 2 | molecule 1 | molecule 2 | average value |
| P(α)-O | 2.4 | 2.1 | 2.1 | 1.9 | 2.1 |
| P(β)-O | 2.1 | 2.4 | 2.3 | 2.2 | 2.3 |
| water | 2.3 | 2.3 | 2.0 | 2.2 | 2.2 |
| D254 | 2.3 | 2.3 | 2.2 | 2.2 | 2.2 |
| H347 | 2.3 | 2.2 | 2.2 | 2.1 | 2.3 |
| Residue 344 | 2.2 | 2.2 | 2.5 | 2.2 | 2.7 |

Comparison of the crystal structures of M344H-Gal-T1.UDP-Gal.metal complexes (FIGS. 4B and 4C) show that the presence of the Mg$^{2+}$ has not perturbed the interactions between the UDP-Gal and the protein molecule, the interactions being similar to those found in the crystal structure of the wild-type protein, β4Gal-T1, in complex with UDP-Gal.Mn$^{2+}$ (PDB:1O0R) (Ramakrishnan et al., *J. Mol. Biol.*, 318:491 (2002); Ramakrishnan and Qasba, *J. Biomol. Struct. Dyb.*, 21:1 (2003)). However, the coordination distance between the atom Nε2 of the His344 to the metal ion is shorter (2.2-2.5 Å) than the corresponding coordination distance found for the sulfur atom of Met344 in the wild type (2.7 Å). These results indicate that the presence of the His residue at 344 strengthens the metal ion binding to the enzyme consistent with the K$_{d1}$ values for Mn$^{2+}$ observed with the mutant and wild type (Table III). Even though the coordination geometry of the Mn$^{2+}$ and Mg$^{2+}$ bound to the M344H-Gal-T1 mutant is very similar, the higher chelating effect by the His residue on the transition metal ion over an alkali earth metal ion could hinder formation of the enzyme transition state complex during catalysis. This is supported by the observed reduction in enzyme activity by the mutant in the presence of Mn$^{2+}$. Additionally, the role of the metal ion in determining the ability of the long loop to undergo the required open to closed, and back to open, conformation change during the catalytic cycle seems to play an important role in determining the kinetics turnover number (k$_{cat}$).

Figure 4A:
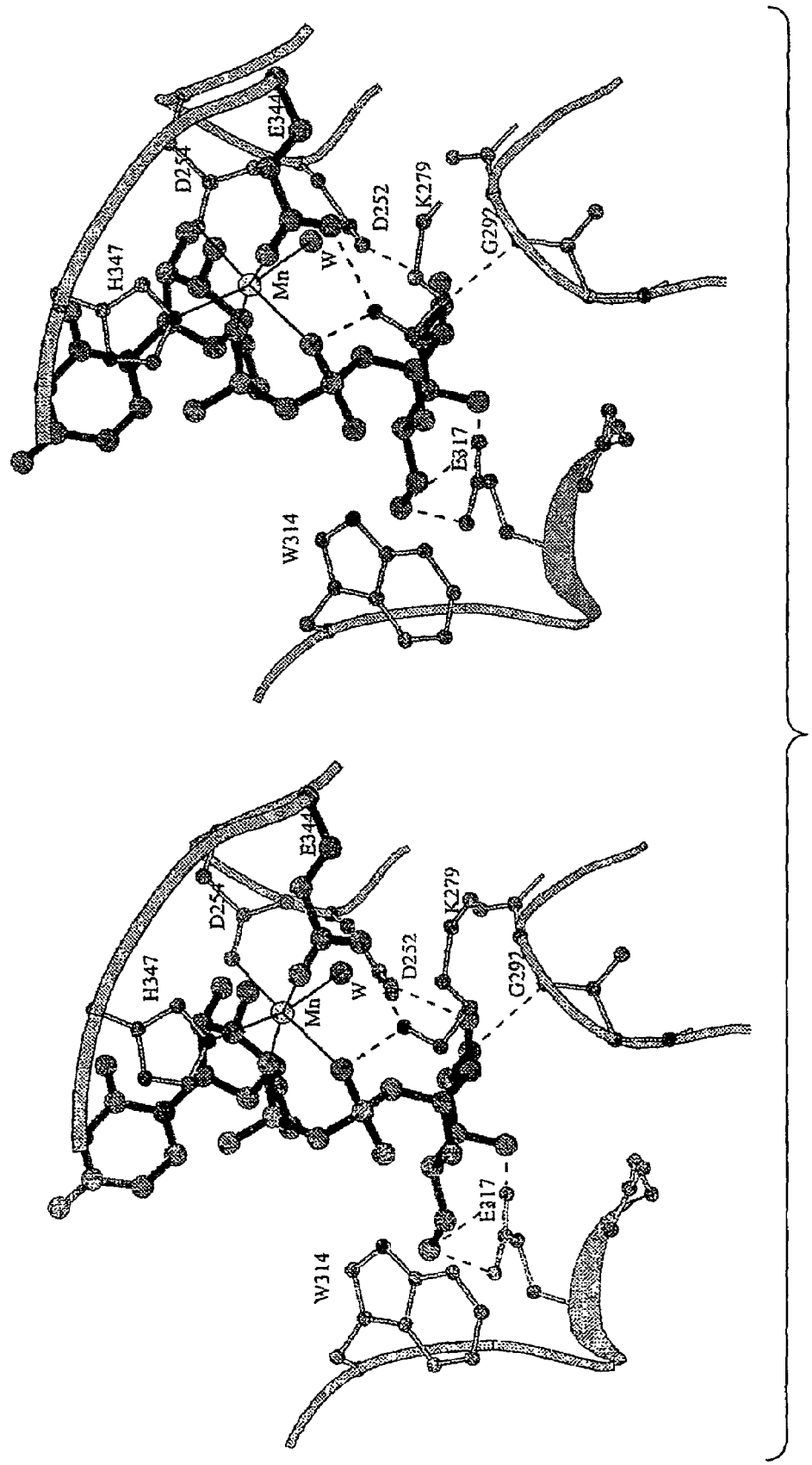
FIG. 4A is a stereo view of the binding of UDP-Gal.$Mn^{2+}$ in the M344E-Gal-T1 mutant. The UDP-Gal and the mutant residues are shown in thick bonds. W represents a water molecule.
Figure 4B:
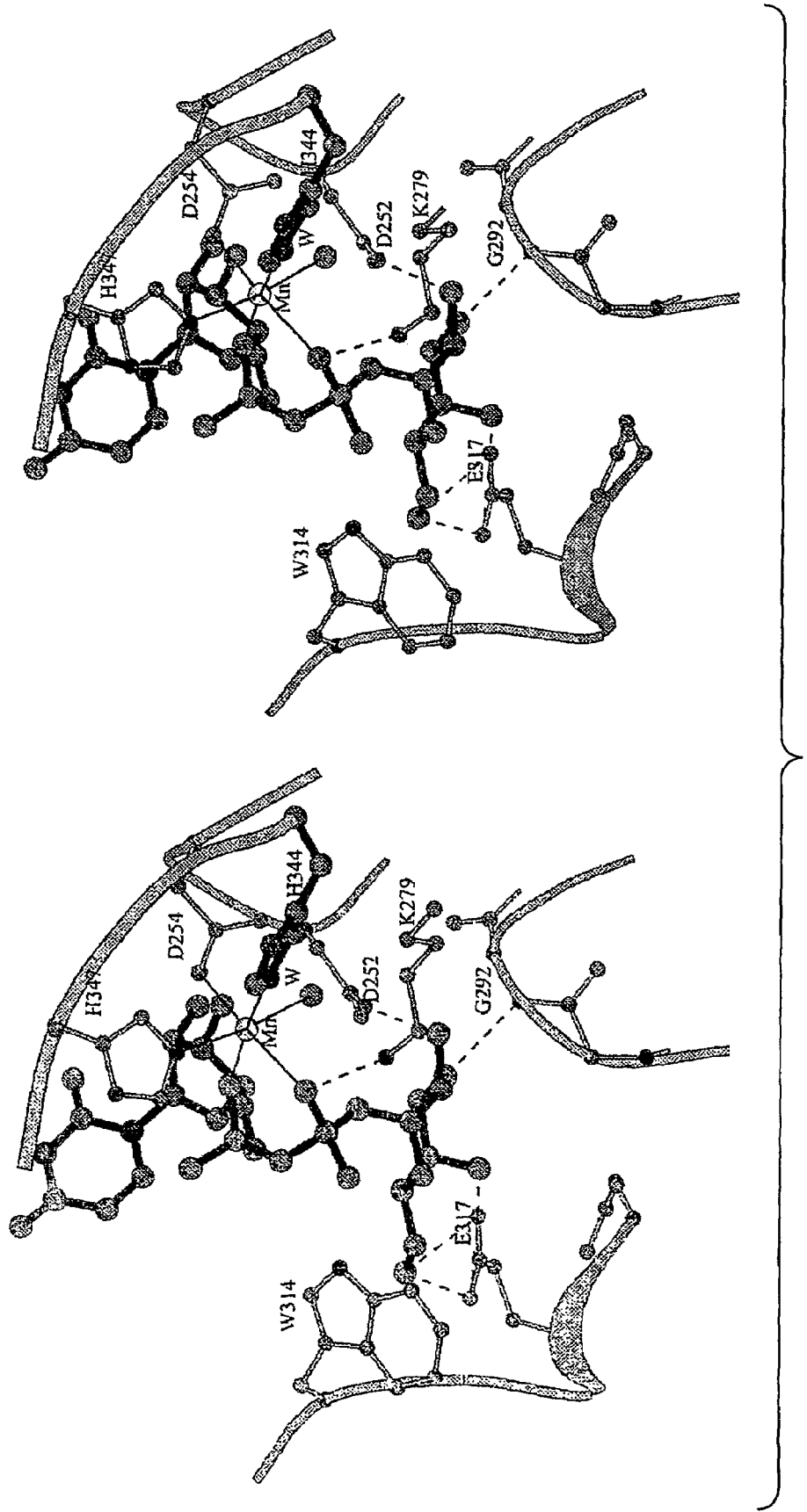
FIG. 4B is a stereo view showing binding of UDP-Gal.$Mn^{2+}$ to the M344H-Gal-T1 mutant. The UDP-Gal and the mutant residues are shown in thick bonds. W represents a water molecule.
Figure 4C:
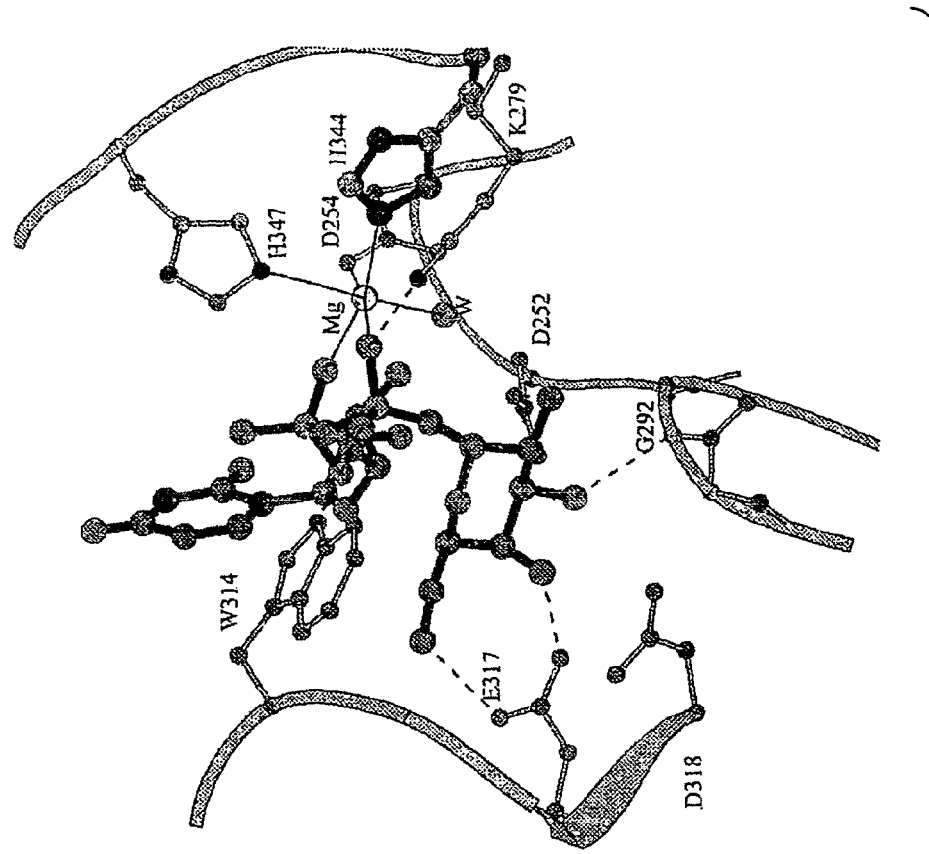
FIG. 4C is a stereo view showing binding of UDP-Gal.$Mg^{2+}$ to the M344H-Gal-T1 mutant. The UDP-Gal and the mutant residues are shown in thick bonds. W represents a water molecule.
Figure 4C:
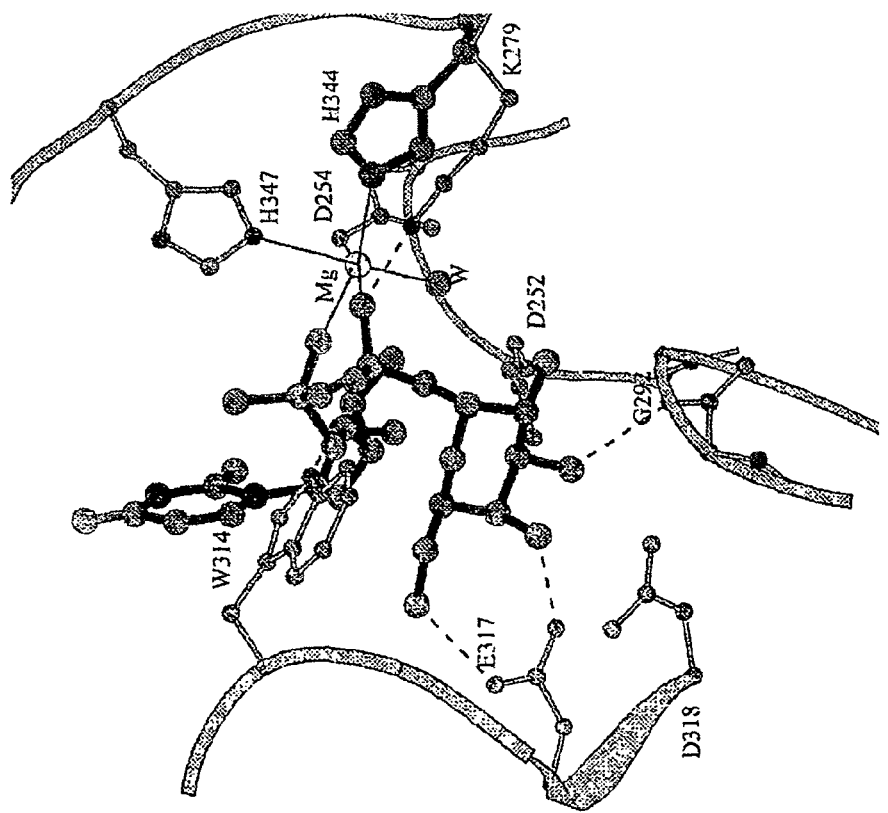
Figure 5:
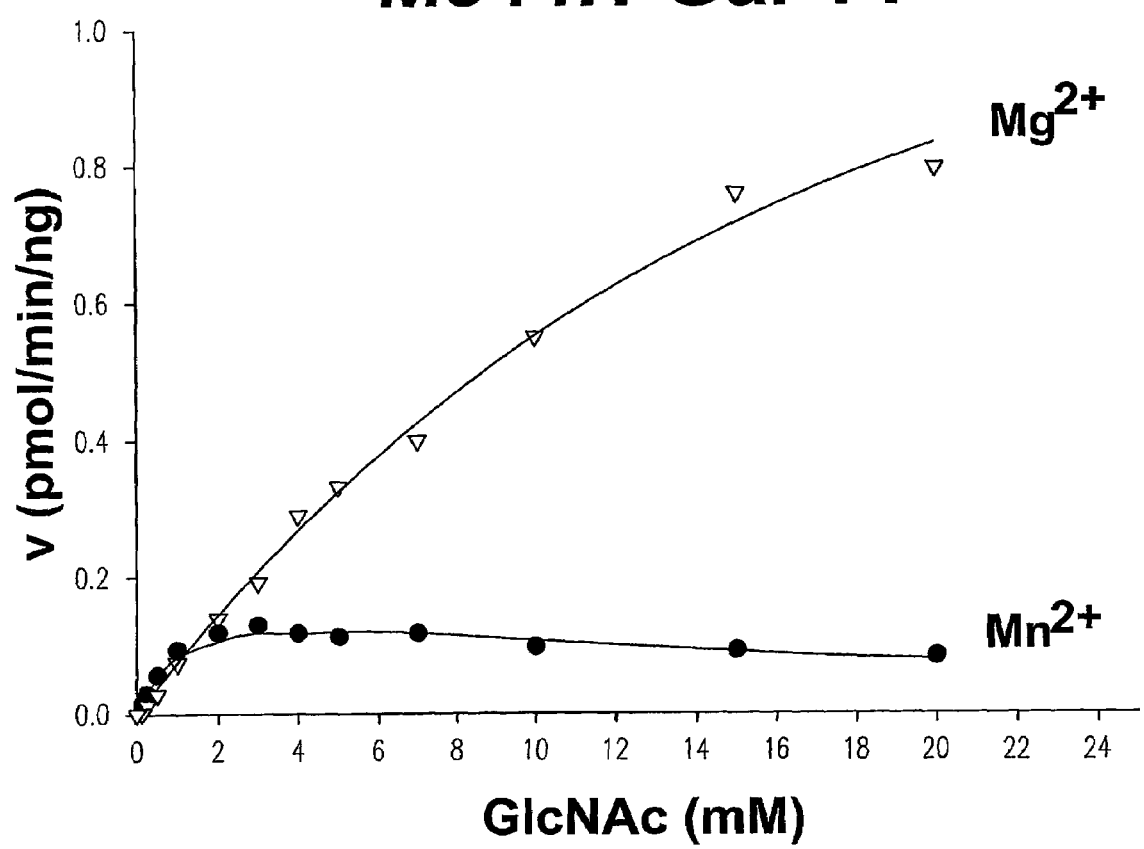
FIG. 5 is an acceptor (GlcNAc) activation curve for the M344H-Gal-T1 mutant in the presence of either $Mn^{2+}$ (closed circles) or $Mg^{2+}$ (open inverted triangles) metal ion.

In all these crystal structures, mutation of Met344 does not affect binding of UDP-Gal (FIGS. 4A, 4B, and 4C). Substitution of Met344 with Glu344 seems to have been very well accommodated in the crystal structure which enhances binding affinity, as reflected in the K$_1$ value (0.5 μM). One of the carboxylate oxygen atoms of the Glu344 forms a strong coordination bond (2.1-2.2 Å) with the Mn$^{2+}$, while the other oxygen atom forms a hydrogen bond with the Lys279 (FIG. 4A). In M344H-Gal-T1.UDP-Gal.metal complexes (FIGS. 4B and 4C) and the wild-type crystal structure with $Mn^{2+}$, the same Lys279 was found to hydrogen-bond with the β-phosphate oxygen atom of the bound UDP-Gal molecule. This may produce the high affinity of the $Mn^{2+}$ for the primary metal binding site of M344E mutant (0.5 µM, derived from FIG. 1B using single binding-site model) compared to the wild-type enzyme. The presence of a strong coordination bond between the residue 344 and the metal ion may result in the hindrance for the formation of the transition state complex during catalysis, resulting in low $k_{cat}$ values.

Example 6

Effect of the Acceptor Concentration on the Catalytic Activity of M344H-Gal-T1

Figure 7A:
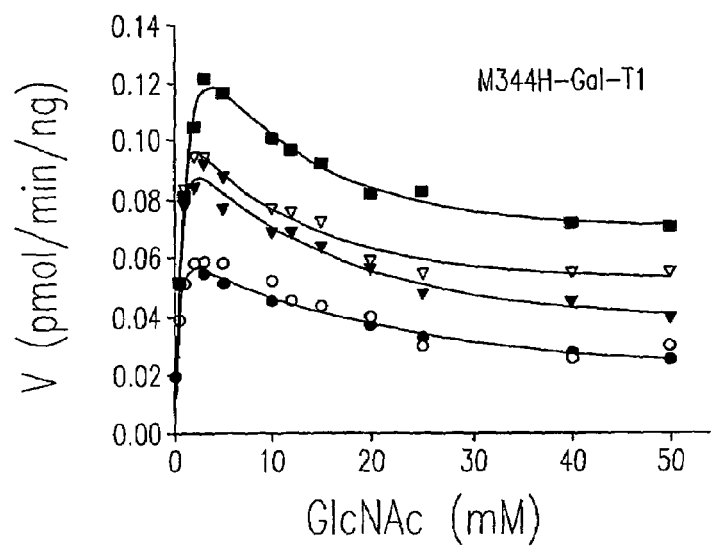
FIG. 7 depicts the effect of GlcNAc concentration on Gal-T activity of the M344H-Gal-T1 mutant (a) and wild-type enzyme, C342T-Gal-T1 (b), at different fixed concentrations of $Mn^{2+}$: (a) (●) 6 μM, (O) 20 μM, (▼) 0.5 mM, (open triangle) 1.5 mM, and (■) 5 mM and (b) (●) 6 μM, (open triangle) 80 μM, (■) 0.5 mM, (▲) 1.5 mM, and (A) 5 mM. The activity of the mutant (a) is inhibited above 2-5 mM GlcNAc at any concentrations of $Mn^{2+}$, whereas the activity of the wild type (b) is inhibited at 25-30 mM GlcNAc and above 0.5 mM $Mn^{2+}$. (c) Effect of either GlcNAc, chitobiose, or β-benzyl-GlcNAc concentration on Gal-T activity of the mutant M344H-Gal-T1 in the presence of 5 mM $Mn^{2+}$. Arrows indicate the inhibition concentration for the respective curves. It is known that the disaccharide chitobiose binds strongly to the Gal-T1 compared to the monosaccharide GlcNAc. The higher the affinity of the acceptor substrate, the lower the required inhibition concentrations.
Figure 7B:
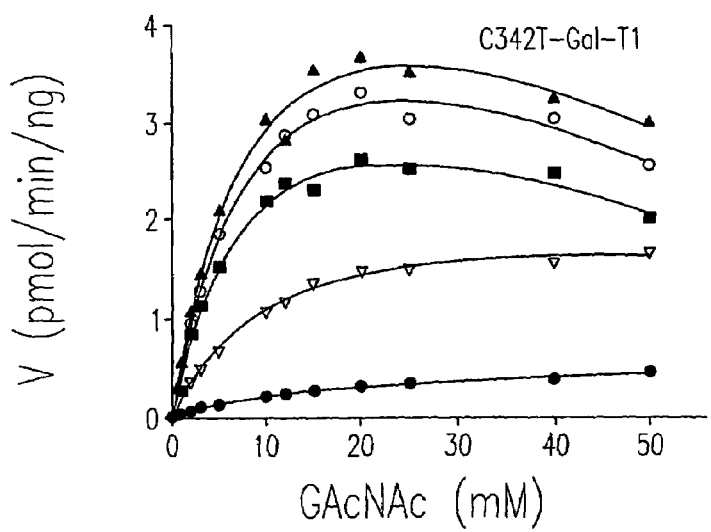
Figure 7C:
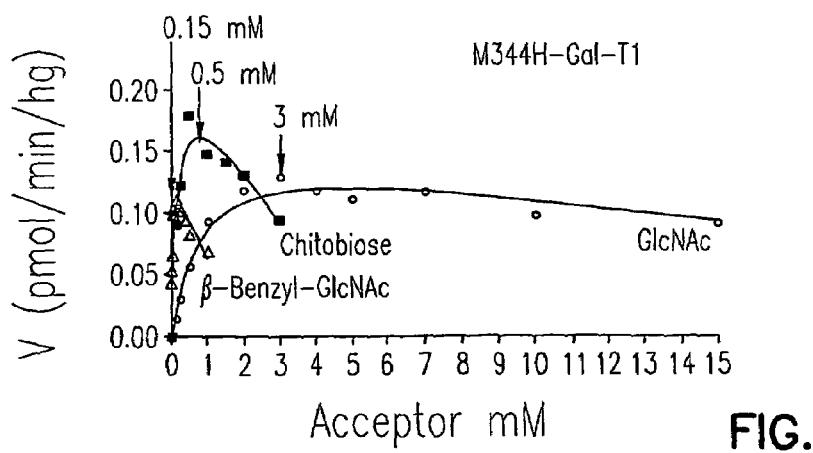

In the presence of $Mn^{2+}$, an inhibition of the catalytic activity of the M344H-Gal-T1 mutant was observed at GlcNAc concentrations of 2-5 mM (FIGS. 7A-C), whereas much higher GlcNAc concentrations (20-25 mM) were necessary to inhibit the catalytic activity of the wild-type enzyme (FIGS. 7A-C). The inhibition of the M344H-Gal-T1 mutant with higher concentrations of the acceptor is independent of the concentration of $Mn^{2+}$ used in the assay (FIGS. 7A-C), while in the wild type, low concentrations of metal have no effect on acceptor inhibition (FIGS. 7A-C). Acceptors with higher affinity such as chitobiose (βGlcNAc1-4GlcNAc) and β-benzyl-GlcNAc inhibit the catalytic activity of the M344H-Gal-T1 mutant at very low concentrations much more strongly than GlcNAc does (FIGS. 7A-C). On the other hand, in the presence of $Mg^{2+}$, under the same conditions, these acceptors do not inhibit the catalytic activity of the M344H-Gal-T1 mutant, indicating that the acceptor substrate inhibition is metal ion-dependent. Inhibition at high acceptor concentrations has been shown as noncompetitive with respect to both $Mn^{2+}$ and UDP (Morrison and Ebner, *J. Biol. Chem.*, 269:5106-5114 (1994)), and it is the result of a dead-end enzyme.$Mn^{2+}$UDP.acceptor complex in the product release phase of the reaction (Bell, J. E., et al., *J. Biol. Chem.*, 251:3003-3013 (1976)). This indicates that during the catalytic cycle, the mutant is in the closed conformation in the presence of $Mn^{2+}$ and UDP and is readily stabilized by the acceptor compared to the wild-type enzyme. This is consistent with a 13-fold reduction in the $K_m$ for GlcNAc of the mutant M344H-Gal-T1, in the presence of $Mn^{2+}$ compared to that of the wild type (Table III). There is also a 37-fold reduction in the $k_{cat}$ of the M344HGal-T1 mutant, which is related to the transition state complex and measures a 3-fold decrease in the catalytic efficiency ($k_{cat}/K_B$) compared to that of the wild-type enzyme. Since the acceptor binds to only the closed conformation, and UDP alone cannot cause an efficient conformational change from the open to the closed conformation (Geren, C. R., et al., *Biochemistry* 14:1461-1463 (1975)), both the sugar acceptor and the metal ion seem to play roles in the conformational changes in the mutant. This property seems to enable crystallization of the M344H-Gal-T1 mutant with the disaccharide acceptor, chitobiose, in the presence of $Mn^{2+}$ and UDP-hexanolamine (see below).

Example 7

Structure-Based Explanation for the Role of Metal Ion in the Conformational Dynamics of M344H-Gal-T1

During the catalytic cycle, upon metal ion and UDP-Gal binding, β14Gal-T1 undergoes a conformational change, from an open to a closed structure. This creates the acceptor-binding site of the enzyme. After catalysis and release of the product disaccharide or oligosaccharide, the closed conformation reverts to the open conformation, exposing the UDP and metal ion to the solvent for environment for their release, and a new round of the catalytic cycle follows. The primary metal binding site is situated in the hinge region of the long loop, where the metal binding residues, Met344 and His347, flank the hinge residue, Ile345. In the open conformation, the metal ion coordinates with Asp254 and Met344 in β4Gal-T1. His347 coordinates with the metal ion only when β4Gal-T1 is in the closed conformation (Ramakrishnan and Qasba, *J. Mol. Biol.*, 310:205-218 (2001)). Asp254 and His347 are strong metal ligands, while the coordination with Met344 is weak; thus, the product UDP and $Mn^{2+}$ are easily released after the catalytic event. The manganese ion binds to the mutant M344H-Gal-T1 20-fold tighter than to the wild-type enzyme (Table III; $K_{d1}$) 1.3 µM). Thus, in the product release phase, the release of UDP and $Mn^{2+}$ may be delayed by keeping the enzyme in the closed conformation and facilitating the binding of the sugar acceptor with the formation of a dead-end molecule. This explains a strong inhibition of the $Mn^{2+}$-dependent catalytic activity of the M344H mutant at low concentrations of various sugar acceptors compared to the wild-type enzyme. This is further evident in the fact that the M344H-Gal-T1 mutant readily crystallizes in the presence of UDP-hexanolamine (UDPH), chitobiose, and $Mn^{2+}$ in the closed conformation, while the wild type has not so far crystallized under similar conditions. Furthermore, magnesium binds weakly to the mutant M344H-Gal-T1 with a dissociation constant ($K_{d1}$) that is 100-fold higher than the $K_{d1}$ for binding of manganese to the mutant. This allows the M344H-Gal-T1 mutant to undergo an efficient conformational change in the presence of $Mg^{2+}$, with the release of a final product thus exhibiting no inhibition at low substrate acceptor concentrations.

Example 8

Crystallization and Determination of the Structure of the M344H-Gal-T1.UDP.$MN^{2+}$ Chitobiose Complex The crystals of the complex were grown by hanging drop methods using the mother liquid containing 20 mg/mL protein, 2 mM chitobiose, 17 mM $MnCl_2$, and UDP-hexanolamine, with the precipitant containing 1.8 M ammonium sulfate, 100 mM Mes-NaOH buffer (pH 6.5), and 10% dioxane. The three-dimensional X-ray diffraction data were collected at 100 K, using an in-house X-ray generator equipped with a mar345 image plate. The data processing and the structure solution were carried out in a manner similar to methods described elsewhere herein. In addition to finding a chitobiose molecule in the active site of the M344H-Gal-T1 molecule, an additional chitobiose molecule was found away from the active site, wedged between two protein molecules.

In the crystal structure, there are two M344H-Gal-T1 molecules in the asymmetric unit, and they are found in the closed conformation. One molecule each of $Mn^{2+}$, UDP-hexanolamine, and chitobiose are bound to each protein molecule. The overall rms deviation of the Cα atoms of the current structure with the M344H-Gal-T1.UDP-Gal.$Mn^{2+}$ structure is only 0.6 Å, indicating the binding of the acceptor substrate has not significantly changed the overall structure of the molecule (Ramakrishnan et al., *Biochemistry*, 43:12513-12522 (2004)). Of the six coordinations seen for the $Mn^{2+}$, only five are quite similar to those found in the crystal structure of the M344H-Gal-T1.UDP-Gal.$MN^{2+}$ complex. The sixth coordination, with the anionic oxygen atom of the phosphate [P($\beta$)], is quite different. This is mainly due to the difference in the binding of UDP-hexanolamine to the M344H-Gal-T1 molecule. Although the overall binding of the UDP-hexanolamine is quite similar to the binding of UDP to the wild-type $\beta$4Gal-T1 in the closed conformation, the hexanolamine moiety at the anionic oxygen atom of the phosphate group [P($\beta$)] could not be accommodated inside the galactose binding pocket. Thus, the whole phosphate group is displaced from the catalytic pocket and placed above the Trp314 side chain.

The acceptor disaccharide molecule, chitobiose, can be clearly located from the difference Fourier electron density maps. Binding of the acceptor sugar, GlcNAc$\beta$1-4GlcNAc, is observed with $\beta$4Gal-T1 in the absence of LA for the first time, and the interactions of the nonreducing end GlcNAc moiety of chitobiose with the M344H-Gal-T1 molecule in the crystal structure presented herein are quite similar to those found in the $\beta$4Gal-T1.LA.GlcNAc complex (Ramakrishnan, B. et al., *J. Mol. Biol.*, 310:205-218 (2001); Ramakrishnan, B., et al., *J. Biomol. Struct. Dyn.*, 21:1-8 (2003)). The N-acetyl moiety of the GlcNAc molecule is bound in the hydrophobic pocket created by residues Arg359, Phe360, and Ile363. The side chain carboxylate group of Asp318 forms a hydrogen bond with the $\beta$4 hydroxyl group of the acceptor GlcNAc moiety of chitobiose. Although the GlcNAc residue at the reducing end does not form any direct hydrogen bond with the M344H-Gal-T1 molecule, it forms hydrophobic interactions with the aromatic side chain of Tyr286. Enzyme kinetics studies have shown that at lower concentrations of GlcNAc the presence of LA enhances the transfer of Gal to GlcNAc; however, in the presence of chitobiose, LA exhibits competitive inhibition of the catalytic activity (Bell, J. et al., *J. Biol. Chem.*, 251:3003-3013 (1976); Grobler J A. et al., *J. Biol. Chem.*, 269:5106-5114 (1994)). In the crystal structure of the $\beta$4Gal-T1.LA.GlcNAc complex, the aromatic side chain of Phe31 of the LA molecule was found to interact with the Tyr286 side chain of the $\beta$4Gal-T1 molecule (Ramakrishnan, B. et al., *J. Mol. Biol.* 310:205-218 (2001); Ramakrishnan, B., et al., *J. Biomol. Struct. Dyn.*, 21:1-8 (2003)). Thus, LA competes for the same binding site (Tyr286) on $\beta$4Gal-T1 as the extended sugar residue of the chitobiose, an observation that is in accord with the kinetic data. These extra hydrophobic interactions alone seem to reduce the $K_m$ value for chitobiose to 1 mM, compared to 5 mM for the monosaccharide, GlcNAc molecule. It is noted that among the $\beta$4Gal-T1 family members, this Tyr286 residue is highly conserved. Since $\beta$4Gal-T1 is mainly involved in the synthesis of complex N-glycan structures longer oligosaccharides are expected to utilize the predicted oligosaccharide binding site on $\beta$4Gal-T1 (Ramakrishnan, B. et al., *J. Mol. Biol.* 318:491-502 (2002)). However, $\beta$4Gal-T1 is also involved in the synthesis of short oligosaccharides attached to proteins such as core structures, and the structure presented herein serves as a model for the binding of such sugars. Using this mutant, we have been successful in crystallizing the enzyme in complex with various higher oligosaccharides. These studies are expected to reveal the binding of the oligosaccharide to $\beta$4Gal-T1.

Example 9

Platelet Protocols

Platelets can be isolated from human volunteers using a metrizamide gradient or a Sepharose column (Falet et al., *Bloods* 96:3786 (2000); Hoffmeister et al., *Cell*, 10:87 (2003)). Human platelets for use in in vitro phagocytosis assays can be suspended at a concentration of $10^9$ per milliliter in 140 mM NaCl, 3 mM KCl, 0.5 mM $MgCl_2$, 5 mM $NaHCO_3$, 10 mM glucose, and 10 mM Hepes (pH 7.4) (Buffer A). The platelets can be labeled with 1.8 µM CM-Orange for 10 minutes at 37° C. and diluted 10× with Buffer A before enzymatic galactosylation.

Murine blood can be obtained from anesthetized mice using 3.75 mg/gram of Avertin (Fluka Chemie, Steinheim, Germany) by retro-orbital eye bleeding into 0.1 volume of Aster-Jandl anticoagulant and centrifuged at 300×g for 8 minutes at room temperature to obtain platelet rich plasma (PRP). Platelets can be separated from plasma by centrifugation at 1200×g for 5 minutes and washed twice in 140 mM NaCl, 5 mM KCl, 12 mM trisodium citrate, 10 mM glucose, and 12.5 mM sucrose, 1 µg/ml $PGE_1$ (pH 6.0) (Buffer B) by centrifugation. Washed platelets can be resuspended at a concentration of $1 \times 10^9$/ml in Buffer A. The platelets can be labeled with 5 µM CMFDA for 15 minutes at 37° C., and diluted 10× with Buffer A before enzymatic galactosylation (Hoffmeister et al., *Cell*, 10:87 (2003)).

GPIb$\alpha$ can be enzymatically cleaved from the surface of chilled or room temperature maintained human platelets with 10 µg/ml of snake venom metalloprotease mocarhagin in Buffer A containing 1 mM $Ca^{+2}$ (Ward et al., *Biochemistry*, 28:8326 (1996)). After enzymatic digestion, the platelets can be washed by centrifugation and the extent of GPIb$\alpha$ removal from the platelet surface can be monitored by flow cytometry (FACScalibur Flow Cytometer, Becton Dickinson Biosciences, San Jose, Calif.) using 5 µg/ml of FITC-conjugated anti-GPIb$\alpha$ SZ2 antibody (Immunotech, Marseille, France).

Terminal $\beta$-N-acetylglucosamine and $\beta$-N-acetylgalactosamine residues can be removed from the surface of platelets using 100 U/ml $\beta$-N-Acetyl-hexosaminidase (NEB, Beverly, Mass.) in 50 mM sodium citrate buffer (pH 6.0) for 30 minutes at 37° C. Enzymatically treated platelets can be washed by centrifugation at 850×g in a 5× volume of Buffer B and resuspended at a concentration of $10^8$ cells/ml in Buffer A.

The effects of chilling on platelet survival and function of mouse or human platlets can be determined by incubating the cells at room temperature (about 25° C.) or on ice for two hours and then rewarming the cells at 37° C. before transfusion into mice or in vitro analysis.

Platelets can be enzymatically galactosylated. Human or murine platelets that are labeled with CM-Orange (about $10^8$ cells/ml) can be chilled for about 2 hours, rewarmed, and incubated with 200 µM uridine 5'-diphosphogalactose (UDP-Gal), in the presence of absence of 20 mU of active, or as a control, heat inactivated (10 minutes at 95° C.) $\beta$4-galactosyltransferase ($\beta$4GalT1) for 30 minutes at 37° C. The platelets can be washed by centrifugation at 850×g for 5 minutes with 5 volumes of Buffer B following galactosylation.

Murine platelets can be labeled with 5 µM CMFDA for 30 minutes at 37° C. can be chilled for 2 hours, rewarmed, and treated using the galactosylation protocol as described for the human platelets above. The platelets can be suspended at $3 \times 10^8$ cells/ml in Buffer A before being injected into mice.

Platelet circulation can be assayed. CMFDA-labeled murine platelets at $1 \times 10^8$ cell/ml that are chilled or room temperature can be injected via the lateral tail vein into mice of the same strain and age. Blood samples can be collected immediately (less than two minutes) and at 0.5, 2, 24, 48, and 72 hours after transfusion into 0.1 ml volume of Aster-Jandl anticoagulant. The percentage of CMFDA positive platelets, recoveries, and platelet counts can be determined through use of flow cytometry (Hoffmeister et al., *Cell*, 10:87 (2003); Baker et al., *Am. J. Hematol.* 56:17 (1997)).

In vitro phagocytic assays are known in the art. Monocytic THP-1 cells (ATCC, Manassas, Va.) can be cultured for 7 days in RPMI 1640 culture medium supplemented with 10% fetal bovine serum, 25 mM Hepes, 2 mM glutamine, and differentiated using 1 ng/ml TGFβ and 50 nM 1,25-(OH)$_2$ vitamine D3 (Calbiochem, San Diego, Calif.) for 24 hours. Differentiation is accompanied by increased expression of $α_Mβ_2$ integrin (Simon et al., *J. Exp. Med.*, 192:193 (2000)). Differentiated THP-1 cells at 2×10$^6$ cells/ml can be plated onto 24-well plates and allowed to adhere for 45 minutes at 37° C. The cells can be activated by addition of 15 ng/ml PMA for 15 minutes. CM-Orange-labeled, chilled or room temperature platelets at 10$^7$ cells/well that were previously subjected to different treatments can be added to the phagocytes in Ca$^{+2}$ and Mg$^{+2}$ containing HBSS (Gibco Invitrogen, Grand Island, N.Y.) or monosaccharide solutions dissolved in Ca$^{+2}$ and Mg$^{+2}$ containing HBSS and incubated for 30 minutes at 37° C. The phagocyte monolayer can be washed 3 times with HBSS, and adherent platelets can be removed by treatment with 0.05% trypsin/0.53 mM EDTA in HBSS at 37° C. for 5 minutes followed by 5 mM EDTA at 4° C. to detach the macrophages for flow cytometry analysis. The macrophages can be gated and 10,000 events can be acquired for each sample.

Platelets can be labeled with lectins. Chilled or room temperature maintained platelets with or without treatments as described above, can be incubated with 2 μg/ml FITC-conjugated succinylated tritium vulgaris-wheat germ agglutinin (S-WGA) or 2.5 μg/ml FITC-conjugated *ricinus communis* I lectin (RCA 1) for 30 minutes at room temperature. Platelet samples can be analyzed immediately by flow cytometry with 10,000 events being analyzed per sample.

Platelets can be immunolabeled and assessed with flow cytometry. Washed murine or human platelets that are chilled or maintained at room temperature can be exposed to 0.01, 0.1, and 6 U/ml thrombin or 0.06, 0.6, and 6 μg/ml CRP for 5 minutes at 37° C. Enzymatic galactosylation can be carried out as described herein. The samples can be diluted (1:100) in PBS (Gibco Invitrogen, Grand Island, N.Y.) and resting or activated platelets can be analyzed by flow cytometry for surface expression of CD62P by staining with FITC-conjugated mAb (5 μg/ml) for 20 minutes at room temperature with 10,000 events analyzed per sample.

Human blood can be obtained from volunteers and stored. PRP can be generated by centrifuging the blood at 250×g for 20 minutes at room temperature and allowing the cells to rest for 30 minutes at 37° C. The PRP can be separated into three equal volumes with sample 1 being untreated, sample 2 being incubated with 200 μM UDP-GAL for 30 minutes at 37° C. before being place at 4° C., and sample 3 being placed at 4° C. Galactose transfer can be performed after chilling the PRP for 1, 2, and 12 days. Prior to galactosylation, sample 3 can be rewarmed to 37° C. for 15 minutes and galactosylation can be achieved in PRP by adding 200 μM UDP-GAL and incubating the cells at 37° C. for 30 minutes. To determine S-WGA and RCA 1 binding at day 0, 1, 2, and 12, platelets from the 3 samples can be isolated by centrifugation add resuspended in Buffer A at a platelet concentration of 10$^8$ cells/ml.

For immunoblot and immunoprecipitation analysis, isolated platelets can be treated with mocarhagin as described above. Platelets can be lysed immediately with 4×SDS-PAGE loading buffer containing 5% β-mercaptoethanol (Laemmli, *Nature*, 227:680 (1970)). Mocarhagin-treated platelets can be centrifuged at 800×g for 5 minutes and the resultant pellet and supernatant can be separated. The platelet pellet can be washed 3 times by centrifugation in Buffer B and resuspended in the original volume of Buffer A. The platelet pellet and supernatant can be solubilized by addition of ¼ volume of 4×SDS-PAGE loading buffer containing 5% β-mercaptoethanol. The samples can then be boiled for 5 minutes.

For immunoprecipitation, isolated platelets can be either kept at room temperature or chilled and rewarmed. Enzymatic galactosylation transfer can be done as described herein, after which the platelets can be lysed by the addition of 0.5 volume of 3× lysis buffer (3% Nonidet P-40, 150 mM Tris/HCl (pH 7.4), 450 mM NaCl, 3 mM EGTA, 3 mM PMSF, 3 mM Na$_3$VO$_4$, 30 μg/ml leupeptin and 30 μg/ml aprotin) (Falet et al., *FEBS Lett.*, 383:165 (1996)). Insoluble material can be removed by centrifugation at 14,000×g for 10 minutes and the soluble fraction can be immunoprecipitated with 5 μg/ml monoclonal anti-GPIbα antibody WM23 bound to protein G-sepharose beads (Pharmacia). Immune complexes can be collected and solubilized in SDS-PAGE buffer containing 5% β-mercaptoethanol.

Proteins can be displayed by SDS-PAGE on an 8% polyacrylamide gel and transferred onto Immobilin-P membrane (Millipore). Membranes can be blocked with 1% BSA in 100 mM NaCl, 20 mM Tris/HCl (pH 7.4) and probed with 5 μg/ml SZ2 or WM23 of the anti-human-GPIbα antibodies followed by the appropriate peroxidase-tagged secondary antibodies or 1 μg/ml peroxidase conjugated-WGA or 0.4 μg/ml RCA-I. Detection can be performed with an enhanced chemiluminescence system (Pierce, Rockford, Ill.).

Aggregation of platelets can be assessed. Platelets that were chilled, galactosylated or not, or maintained at room temperature, can be washed once with Buffer B by centrifugation and resuspended in Buffer A. Samples of 0.3 ml of platelets can be stirred and exposed to 0.01, 0.1, and 1 U/ml thrombin or 0.06, 0.6, and 6 μg/ml collagen related peptide (CRP) at 37° C. In agglutination experiments, the washed platelets can be treated with UDP-Gal as described above, collected by centrifugation at 300×g for 5 minutes, resuspended in 0.3 ml of plasma, and exposed to 0.01, 0.1, and 1 mg/ml ristocetin at 37° C. For longterm storage, 0.3 ml samples can be removed at day 0, 1, 2, and 12 from untreated samples and samples treated with UDP-Gal. The samples can be rewarmed to 37° C. for 15 minutes and 1 U/ml of thrombin can be added to start the aggregation reaction. Light transmission can be recorded to determine aggregation (Bio/Data aggregometer, Horsham, Pa.).

Rabbit red blood cell (rRBC) phagocytosis assay. Rabbit blood can be collected into EDTA containing vacutainers (Beckton Dickinson Vacutainer Systems, Franklin Lakes, N.J.). rRBCs can be collected by centrifugation at 300×g, washed 3 times by centrifugation at room temperature with HBSS containing Ca$^{+2}$ and Mg$^{+2}$ (Gibco Invitrogen) and resuspended in the same buffer at 10$^8$ cells/ml in the presence or absence of 10 mM GlcNAc or 10 μM BGlcNAc. Galactose transfer can be performed by addition of 200 or 400 μM UDP-Gal with or without adding 20 mU bovine β4GalT1 per 10$^8$ rRBCs. S-WGA and RCA-I lectin binding can be performed by adding 0.11 g/ml lectin per 10$^7$ rRBCs for 20 minutes at room temperature and using flow cytometry. rRBCs can be preloaded with 5 μM CMFDA as described for platelets and added to the isolated human polymorphonuclear cells (Valerius et al., *Cell*, 24:195 (1981)). 100 μl of rRBCs can be added to 100 μl (10$^7$ cells/ml) polymorphonulcear cells and the cell suspensions can be gently rocked for 30 minutes at 37° C. Adherent rRBCs can be lysed by addition of 10 volumes of H$_2$O followed by the immediate addition of sufficient 20× saline to return the osmolarity to normal. The neutrophils can be checked for associated rabbit RBCs by light microscopy, stained with a CD11b-PE labeled antibody for 20 minutes on ice, and analyzed by flow cytometry. CD11b positive cells can be gated and 10,000 events acquired.

All publications, patents and patent applications are incorporated herein by reference. While in the foregoing specification this invention has been described in relation to certain preferred embodiments thereof, and many details have been set forth for purposes of illustration, it will be apparent to those skilled in the art that the invention is susceptible to additional embodiments and that certain of the details described herein may be varied considerably without departing from the basic principles of the invention.

What is claimed is:

1. A purified and isolated catalytic domain from a β(1,4)-galactosyltransferase I corresponding to SEQ ID NO: 6, and consisting of a conservative amino acid exchange at amino acid position 344 of SEQ ID NO: 6, wherein the amino acid exchange at position 344 of SEQ ID NO: 6 is selected from M344H, M344E, M344A, M344S, or M344Q, and wherein the catalytic domain catalyzes formation of galactose-β(1,4)-N-acetylglucosamine bond in the presence of magnesium, and further comprising a conservative amino acid exchange at an amino acid position corresponding to amino acid position 342 of SEQ ID NO: 6.

2. The catalytic domain according to claim 1, wherein the rate of formation of the galactose-β(1,4)-N-acetylglucosamine bond is at least two-fold, five-fold, ten-fold, or one hundred-fold greater than wild-type β(1,4)-galactosyltransferase I in the presence of magnesium.

3. The catalytic domain of claim 1, wherein histidine is exchanged for methionine at an amino acid position corresponding to amino acid position 344 of SEQ ID NO: 6.

4. The catalytic domain according to claim 1, wherein threonine is exchanged for cysteine at amino acid position 342.

5. A polypeptide comprising the catalytic domain according to claim 1.

6. A purified and isolated catalytic domain from a β(1,4)-galactosyltransferase I corresponding to SEQ ID NO: 6, and consisting of a conservative amino acid exchange at amino acid position 344 of SEQ ID NO: 6, wherein the amino acid exchange at position 344 of SEQ ID NO: 6 is selected from M344H, M344E, M344A, M344S, or M344Q, and wherein the catalytic domain catalyzes formation of an N-acetylgalactosamine-β(1,4)-N-acetylglucosamine bond in the presence of magnesium.

7. A purified and isolated catalytic domain from β(1,4)-galactosyltransferase I of claim 6 wherein the domain catalyzes formation of an N-acetylgalactosamine-13(1,4)-glucose bond in the presence of α-lactalbumin and magnesium.

8. A polypeptide comprising the catalytic domain according to claim 7.

9. A polypeptide comprising the catalytic domain according to claim 6.

10. The catalytic domain according to claim 6, further comprising a conservative amino acid substitution at an amino acid position corresponding to amino acid position 342 of SEQ ID NO: 6.

11. The catalytic domain according to claim 6, wherein threonine is exchanged for cysteine at amino acid position 342.

12. A purified and isolated catalytic domain from a β(1,4)-galactosyltransferase I corresponding to SEQ ID NO: 6, and consisting of a conservative amino acid exchange at amino acid position 344 of SEQ ID NO: 6, wherein the amino acid exchange at position 344 of SEQ ID NO: 6 is selected from M344E, M344A, M344S, or M344Q, and wherein the catalytic domain catalyzes formation of an N-acetylgalactosamine-β(1,4)-N-acetylglucosamine bond in the presence of magnesium.

\* \* \* \* \*

SEQUENCE LISTING

```
<160> NUMBER OF SEQ ID NOS: 13

<210> SEQ ID NO 1
<211> LENGTH: 6
<212> TYPE: PRT
<213> ORGANISM: Homo sapiens

<400> SEQUENCE: 1

Cys Arg Met Ile Arg His
1               5

<210> SEQ ID NO 2
<211> LENGTH: 7
<212> TYPE: PRT
<213> ORGANISM: Homo sapiens

<400> SEQUENCE: 2

Phe Asn Arg Ala Lys Leu Leu
1               5

<210> SEQ ID NO 3
<211> LENGTH: 7
<212> TYPE: PRT
<213> ORGANISM: Homo sapiens

<400> SEQUENCE: 3

Tyr Val Gln Tyr Phe Gly Gly
1               5

<210> SEQ ID NO 4
<211> LENGTH: 398
<212> TYPE: PRT
<213> ORGANISM: Homo sapiens

<400> SEQUENCE: 4

Met Arg Leu Arg Glu Pro Leu Leu Ser Arg Ser Ala Ala Met Pro Gly
1               5                   10                  15

Ala Ser Leu Gln Arg Ala Cys Arg Leu Leu Val Ala Val Cys Ala Leu
                20                  25                  30

His Leu Gly Val Thr Leu Val Tyr Tyr Leu Ala Gly Arg Asp Leu Ser
            35                  40                  45

Arg Leu Pro Gln Leu Val Gly Val Ser Thr Pro Leu Gln Gly Gly Ser
        50                  55                  60

Asn Ser Ala Ala Ala Ile Gly Gln Ser Ser Gly Asp Leu Arg Thr Gly
65                  70                  75                  80

Gly Ala Arg Pro Pro Pro Pro Leu Gly Ala Ser Ser Gln Pro Arg Pro
                85                  90                  95

Gly Gly Asp Ser Ser Pro Val Val Asp Ser Gly Pro Gly Pro Ala Ser
                100                 105                 110

Asn Leu Thr Ser Val Pro Val Pro His Thr Thr Ala Leu Ser Leu Pro
            115                 120                 125

Ala Cys Pro Glu Glu Ser Pro Leu Leu Val Gly Pro Met Leu Ile Glu
        130                 135                 140
```

Phe Asn Met Pro Val Asp Leu Glu Leu Val Ala Lys Gln Asn Pro Asn
145                 150                 155                 160

Val Lys Met Gly Gly Arg Tyr Ala Pro Arg Asp Cys Val Ser Pro His
            165                 170                 175

Lys Val Ala Ile Ile Pro Phe Arg Asn Arg Gln Glu His Leu Lys
        180                 185                 190

Tyr Trp Leu Tyr Tyr Leu His Pro Val Leu Gln Arg Gln Leu Asp
    195                 200                 205

Tyr Gly Ile Tyr Val Ile Asn Gln Ala Gly Asp Thr Ile Phe Asn Arg
210                 215                 220

Ala Lys Leu Leu Asn Val Gly Phe Gln Glu Ala Leu Lys Asp Tyr Asp
225                 230                 235                 240

Tyr Thr Cys Phe Val Phe Ser Asp Val Asp Leu Ile Pro Met Asn Asp
                245                 250                 255

His Asn Ala Tyr Arg Cys Phe Ser Gln Pro Arg His Ile Ser Val Ala
            260                 265                 270

Met Asp Lys Phe Gly Phe Ser Leu Pro Tyr Val Gln Tyr Phe Gly Gly
        275                 280                 285

Val Ser Ala Ser Ser Lys Gln Gln Phe Leu Thr Ile Asn Gly Phe Pro
290                 295                 300

Asn Asn Tyr Trp Gly Trp Gly Gly Glu Asp Asp Asp Ile Phe Asn Arg
305                 310                 315                 320

Leu Val Phe Arg Gly Met Ser Ile Ser Arg Pro Asn Ala Val Val Gly
                325                 330                 335

Thr Cys Arg Met Ile Arg His Ser Arg Asp Lys Lys Asn Glu Pro Asn
            340                 345                 350

Pro Gln Arg Phe Asp Arg Ile Ala His Thr Lys Glu Thr Met Leu Ser
        355                 360                 365

Asp Gly Leu Asn Ser Leu Thr Tyr Gln Val Leu Asp Val Gln Arg Tyr
    370                 375                 380

Pro Leu Tyr Thr Gln Ile Thr Val Asp Ile Gly Thr Pro Ser
385                 390                 395

<210> SEQ ID NO 5
<211> LENGTH: 399
<212> TYPE: PRT
<213> ORGANISM: Mus musculus

<400> SEQUENCE: 5

Met Arg Phe Arg Glu Gln Phe Leu Gly Gly Ser Ala Ala Met Pro Gly
1               5                   10                  15

Ala Thr Leu Gln Arg Ala Cys Arg Leu Leu Val Ala Val Cys Ala Leu
            20                  25                  30

His Leu Gly Val Thr Leu Val Tyr Tyr Leu Ser Gly Arg Asp Leu Ser
        35                  40                  45

Arg Leu Pro Gln Leu Val Gly Val Ser Ser Thr Leu Gln Gly Gly Thr
    50                  55                  60

Asn Gly Ala Ala Ala Ser Lys Gln Pro Pro Gly Glu Gln Arg Pro Arg
65                  70                  75                  80

Gly Ala Arg Pro Pro Pro Leu Gly Val Ser Pro Lys Pro Arg Pro
            85                  90                  95

Gly Leu Asp Ser Ser Pro Gly Ala Ala Ser Gly Pro Gly Leu Lys Ser
        100                 105                 110

Asn Leu Ser Ser Leu Pro Val Pro Thr Thr Thr Gly Leu Leu Ser Leu
    115                 120                 125

```
Pro Ala Cys Pro Glu Glu Ser Pro Leu Leu Val Gly Pro Met Leu Ile
        130                 135                 140

Asp Phe Asn Ile Ala Val Asp Leu Glu Leu Leu Ala Lys Lys Asn Pro
145                 150                 155                 160

Glu Ile Lys Thr Gly Gly Arg Tyr Ser Pro Lys Asp Cys Val Ser Pro
                165                 170                 175

His Lys Val Ala Ile Ile Pro Phe Arg Asn Arg Gln Glu His Leu
            180                 185                 190

Lys Tyr Trp Leu Tyr Tyr Leu His Pro Ile Leu Gln Arg Gln Gln Leu
                195                 200                 205

Asp Tyr Gly Ile Tyr Val Ile Asn Gln Ala Gly Asp Thr Met Phe Asn
210                 215                 220

Arg Ala Lys Leu Leu Asn Ile Gly Phe Gln Glu Ala Leu Lys Asp Tyr
225                 230                 235                 240

Asp Tyr Asn Cys Phe Val Phe Ser Asp Val Asp Leu Ile Pro Met Asp
                245                 250                 255

Asp Arg Asn Ala Tyr Arg Cys Phe Ser Gln Pro Arg His Ile Ser Val
                260                 265                 270

Ala Met Asp Lys Phe Gly Phe Ser Leu Pro Tyr Val Gln Tyr Phe Gly
    275                 280                 285

Gly Val Ser Ala Leu Ser Lys Gln Gln Phe Leu Ala Ile Asn Gly Phe
    290                 295                 300

Pro Asn Asn Tyr Trp Gly Trp Gly Gly Glu Asp Asp Asp Ile Phe Asn
305                 310                 315                 320

Arg Leu Val His Lys Gly Met Ser Ile Ser Arg Pro Asn Ala Val Val
                325                 330                 335

Gly Arg Cys Arg Met Ile Arg His Ser Arg Asp Lys Lys Asn Glu Pro
                340                 345                 350

Asn Pro Gln Arg Phe Asp Arg Ile Ala His Thr Lys Glu Thr Met Arg
                355                 360                 365

Phe Asp Gly Leu Asn Ser Leu Thr Tyr Lys Val Leu Asp Val Gln Arg
                370                 375                 380

Tyr Pro Leu Tyr Thr Gln Ile Thr Val Asp Ile Gly Thr Pro Arg
385                 390                 395

<210> SEQ ID NO 6
<211> LENGTH: 402
<212> TYPE: PRT
<213> ORGANISM: Bos taurus

<400> SEQUENCE: 6

Met Lys Phe Arg Glu Pro Leu Leu Gly Gly Ser Ala Ala Met Pro Gly
1               5                   10                  15

Ala Ser Leu Gln Arg Ala Cys Arg Leu Leu Val Ala Val Cys Ala Leu
                20                  25                  30

His Leu Gly Val Thr Leu Val Tyr Tyr Leu Ala Gly Arg Asp Leu Arg
            35                  40                  45

Arg Leu Pro Gln Leu Val Gly Val His Pro Pro Leu Gln Gly Ser Ser
        50                  55                  60

His Gly Ala Ala Ala Ile Gly Gln Pro Ser Gly Glu Leu Arg Leu Arg
65                  70                  75                  80

Gly Val Ala Pro Pro Pro Leu Gln Asn Ser Ser Lys Pro Arg Ser
                85                  90                  95

Arg Ala Pro Ser Asn Leu Asp Ala Tyr Ser His Pro Gly Pro Gly Pro
                100                 105                 110
```

```
Gly Pro Gly Ser Asn Leu Thr Ser Ala Pro Val Pro Ser Thr Thr Thr
            115                 120                 125
Arg Ser Leu Thr Ala Cys Pro Glu Glu Ser Pro Leu Leu Val Gly Pro
            130                 135                 140
Met Leu Ile Glu Phe Asn Ile Pro Val Asp Leu Lys Leu Ile Glu Gln
145                 150                 155                 160
Gln Asn Pro Lys Val Lys Leu Gly Gly Arg Tyr Thr Pro Met Asp Cys
                165                 170                 175
Ile Ser Pro His Lys Val Ala Ile Ile Leu Phe Arg Asn Arg Gln
                180                 185                 190
Glu His Leu Lys Tyr Trp Leu Tyr Tyr Leu His Pro Met Val Gln Arg
            195                 200                 205
Gln Gln Leu Asp Tyr Gly Ile Tyr Val Ile Asn Gln Ala Gly Glu Ser
            210                 215                 220
Met Phe Asn Arg Ala Lys Leu Leu Asn Val Gly Phe Lys Glu Ala Leu
225                 230                 235                 240
Lys Asp Tyr Asp Tyr Asn Cys Phe Val Phe Ser Asp Val Asp Leu Ile
                245                 250                 255
Pro Met Asn Asp His Asn Thr Tyr Arg Cys Phe Ser Gln Pro Arg His
                260                 265                 270
Ile Ser Val Ala Met Asp Lys Phe Gly Phe Ser Leu Pro Tyr Val Gln
                275                 280                 285
Tyr Phe Gly Gly Val Ser Ala Leu Ser Lys Gln Gln Phe Leu Ser Ile
            290                 295                 300
Asn Gly Phe Pro Asn Asn Tyr Trp Gly Trp Gly Gly Glu Asp Asp Asp
305                 310                 315                 320
Ile Tyr Asn Arg Leu Ala Phe Arg Gly Met Ser Val Ser Arg Pro Asn
                325                 330                 335
Ala Val Ile Gly Lys Cys Arg Met Ile Arg His Ser Arg Asp Lys Lys
                340                 345                 350
Asn Glu Pro Asn Pro Gln Arg Phe Asp Arg Ile Ala His Thr Lys Glu
            355                 360                 365
Thr Met Leu Ser Asp Gly Leu Asn Ser Leu Thr Tyr Met Val Leu Glu
            370                 375                 380
Val Gln Arg Tyr Pro Leu Tyr Thr Lys Ile Thr Val Asp Ile Gly Thr
385                 390                 395                 400
Pro Ser

<210> SEQ ID NO 7
<211> LENGTH: 113
<212> TYPE: PRT
<213> ORGANISM: Homo sapiens

<400> SEQUENCE: 7

Arg Asp Leu Ser Arg Leu Pro Gln Leu Val Gly Val Ser Thr Pro Leu
  1               5                  10                  15
Gln Gly Gly Ser Asn Ser Ala Ala Ile Gly Gln Ser Ser Gly Asp
                20                  25                  30
Leu Arg Thr Gly Gly Ala Arg Pro Pro Pro Leu Gly Ala Ser Ser
            35                  40                  45
Gln Pro Arg Pro Gly Gly Asp Ser Ser Pro Val Val Asp Ser Gly Pro
        50                  55                  60
Gly Pro Ala Ser Asn Leu Thr Ser Val Pro Val Pro His Thr Thr Ala
65                  70                  75                  80
Leu Ser Leu Pro Ala Cys Pro Glu Glu Ser Pro Leu Leu Val Gly Pro
```

```
                    85                  90                  95
Met Leu Ile Glu Phe Asn Met Pro Val Asp Leu Glu Leu Val Ala Lys
                100                 105                 110
Gln

<210> SEQ ID NO 8
<211> LENGTH: 85
<212> TYPE: PRT
<213> ORGANISM: Bos taurus

<400> SEQUENCE: 8

Arg Asp Leu Arg Arg Leu Pro Gln Leu Val Gly Val His Pro Pro Leu
1               5                   10                  15

Gln Gly Ser Ser His Gly Ala Ala Ile Gly Gln Pro Ser Gly Glu
            20                  25                  30

Leu Arg Leu Arg Gly Val Ala Pro Pro Pro Leu Gln Asn Ser Ser
        35                  40                  45

Lys Pro Arg Ser Arg Ala Pro Ser Asn Leu Asp Ala Tyr Ser His Pro
    50                  55                  60

Gly Pro Gly Pro Gly Pro Gly Ser Asn Leu Thr Ser Ala Pro Val Pro
65                  70                  75                  80

Ser Thr Thr Thr Arg
                85

<210> SEQ ID NO 9
<211> LENGTH: 273
<212> TYPE: PRT
<213> ORGANISM: Homo sapiens

<400> SEQUENCE: 9

Ser Leu Pro Ala Cys Pro Glu Glu Ser Pro Leu Leu Val Gly Pro Met
1               5                   10                  15

Leu Ile Glu Phe Asn Met Pro Val Asp Leu Glu Leu Val Ala Lys Gln
                20                  25                  30

Asn Pro Asn Val Lys Met Gly Gly Arg Tyr Ala Pro Arg Asp Cys Val
            35                  40                  45

Ser Pro His Lys Val Ala Ile Ile Ile Pro Phe Arg Asn Arg Gln Glu
    50                  55                  60

His Leu Lys Tyr Trp Leu Tyr Tyr Leu His Pro Val Leu Gln Arg Gln
65                  70                  75                  80

Gln Leu Asp Tyr Gly Ile Tyr Val Ile Asn Gln Ala Gly Asp Thr Ile
            85                  90                  95

Phe Asn Arg Ala Lys Leu Leu Asn Val Gly Phe Gln Glu Ala Leu Lys
                100                 105                 110

Asp Tyr Asp Tyr Thr Cys Phe Val Phe Ser Asp Val Asp Leu Ile Pro
            115                 120                 125

Met Asn Asp His Asn Ala Tyr Arg Cys Phe Ser Gln Pro Arg His Ile
    130                 135                 140

Ser Val Ala Met Asp Lys Phe Gly Phe Ser Leu Pro Tyr Val Gln Tyr
145                 150                 155                 160

Phe Gly Gly Val Ser Ala Ser Ser Lys Gln Gln Phe Leu Thr Ile Asn
                165                 170                 175

Gly Phe Pro Asn Asn Tyr Trp Gly Trp Gly Gly Glu Asp Asp Asp Ile
            180                 185                 190

Phe Asn Arg Leu Val Phe Arg Gly Met Ser Ile Ser Arg Pro Asn Ala
        195                 200                 205
```

```
Val Val Gly Thr Cys Arg Met Ile Arg His Ser Arg Asp Lys Lys Asn
    210                 215                 220

Glu Pro Asn Pro Gln Arg Phe Asp Arg Ile Ala His Thr Lys Glu Thr
225                 230                 235                 240

Met Leu Ser Asp Gly Leu Asn Ser Leu Thr Tyr Gln Val Leu Asp Val
                245                 250                 255

Gln Arg Tyr Pro Leu Tyr Thr Gln Ile Thr Val Asp Ile Gly Thr Pro
                260                 265                 270

Ser

<210> SEQ ID NO 10
<211> LENGTH: 273
<212> TYPE: PRT
<213> ORGANISM: Bos taurus

<400> SEQUENCE: 10

Ser Leu Thr Ala Cys Pro Glu Glu Ser Pro Leu Leu Val Gly Pro Met
  1               5                  10                  15

Leu Ile Glu Phe Asn Ile Pro Val Asp Leu Lys Leu Ile Glu Gln Gln
                 20                  25                  30

Asn Pro Lys Val Lys Leu Gly Gly Arg Tyr Thr Pro Met Asp Cys Ile
             35                  40                  45

Ser Pro His Lys Val Ala Ile Ile Leu Phe Arg Asn Arg Gln Glu
 50                  55                  60

His Leu Lys Tyr Trp Leu Tyr Tyr Leu His Pro Met Val Gln Arg Gln
 65                  70                  75                  80

Gln Leu Asp Tyr Gly Ile Tyr Val Ile Asn Gln Ala Gly Glu Ser Met
                 85                  90                  95

Phe Asn Arg Ala Lys Leu Leu Asn Val Gly Phe Lys Glu Ala Leu Lys
                100                 105                 110

Asp Tyr Asp Tyr Asn Cys Phe Val Phe Ser Asp Val Asp Leu Ile Pro
            115                 120                 125

Met Asn Asp His Asn Thr Tyr Arg Cys Phe Ser Gln Pro Arg His Ile
130                 135                 140

Ser Val Ala Met Asp Lys Phe Gly Phe Ser Leu Pro Tyr Val Gln Tyr
145                 150                 155                 160

Phe Gly Gly Val Ser Ala Leu Ser Lys Gln Gln Phe Leu Ser Ile Asn
                165                 170                 175

Gly Phe Pro Asn Asn Tyr Trp Gly Trp Gly Gly Glu Asp Asp Asp Ile
            180                 185                 190

Tyr Asn Arg Leu Ala Phe Arg Gly Met Ser Val Ser Arg Pro Asn Ala
        195                 200                 205

Val Ile Gly Lys Cys Arg Met Ile Arg His Ser Arg Asp Lys Lys Asn
    210                 215                 220

Glu Pro Asn Pro Gln Arg Phe Asp Arg Ile Ala His Thr Lys Glu Thr
225                 230                 235                 240

Met Leu Ser Asp Gly Leu Asn Ser Leu Thr Tyr Met Val Leu Glu Val
                245                 250                 255

Gln Arg Tyr Pro Leu Tyr Thr Lys Ile Thr Val Asp Ile Gly Thr Pro
                260                 265                 270

Ser

<210> SEQ ID NO 11
<211> LENGTH: 1197
<212> TYPE: PRT
<213> ORGANISM: Homo sapiens
```

<400> SEQUENCE: 11

```
Ala Thr Gly Ala Gly Gly Cys Thr Thr Cys Gly Gly Gly Ala Gly Cys
 1               5                  10                  15

Cys Gly Cys Thr Cys Cys Thr Gly Ala Gly Cys Cys Gly Gly Ala Gly
            20                  25                  30

Cys Gly Cys Cys Gly Cys Gly Ala Thr Gly Cys Cys Ala Gly Gly Cys
        35                  40                  45

Gly Cys Gly Thr Cys Cys Cys Thr Ala Cys Ala Gly Cys Gly Gly Gly
    50                  55                  60

Cys Cys Thr Gly Cys Cys Gly Cys Cys Thr Gly Cys Thr Cys Gly Thr
65                  70                  75                  80

Gly Gly Cys Cys Gly Thr Cys Thr Gly Cys Gly Cys Thr Cys Thr Gly
                85                  90                  95

Cys Ala Cys Cys Thr Thr Gly Gly Cys Gly Thr Cys Ala Cys Cys Cys
            100                 105                 110

Thr Cys Gly Thr Thr Thr Ala Cys Thr Ala Cys Cys Thr Gly Gly Cys
        115                 120                 125

Thr Gly Gly Cys Cys Gly Cys Gly Ala Cys Cys Thr Gly Ala Gly Cys
    130                 135                 140

Cys Gly Cys Cys Thr Gly Cys Cys Cys Cys Ala Ala Cys Thr Gly Gly
145                 150                 155                 160

Thr Cys Gly Gly Ala Gly Thr Cys Thr Cys Cys Ala Cys Ala Cys Cys
                165                 170                 175

Gly Cys Thr Gly Cys Ala Gly Gly Gly Cys Gly Gly Gly Thr Cys Gly
            180                 185                 190

Ala Ala Cys Ala Gly Thr Gly Cys Cys Gly Cys Cys Gly Cys Cys Ala
        195                 200                 205

Thr Cys Gly Gly Gly Cys Ala Gly Thr Cys Cys Thr Cys Cys Gly Gly
    210                 215                 220

Gly Gly Ala Cys Cys Thr Cys Cys Gly Gly Ala Cys Cys Gly Gly Ala
225                 230                 235                 240

Gly Gly Gly Gly Cys Cys Cys Gly Gly Cys Cys Gly Cys Cys Gly Cys
                245                 250                 255

Cys Thr Cys Cys Thr Cys Thr Ala Gly Gly Cys Gly Cys Cys Thr Cys
            260                 265                 270

Cys Thr Cys Cys Cys Ala Gly Cys Cys Gly Cys Gly Cys Cys Cys Gly
        275                 280                 285

Gly Gly Thr Gly Gly Cys Gly Ala Cys Thr Cys Cys Ala Gly Cys Cys
    290                 295                 300

Cys Ala Gly Thr Cys Gly Thr Gly Gly Ala Thr Thr Cys Thr Gly Gly
305                 310                 315                 320

Cys Cys Cys Thr Gly Gly Cys Cys Cys Cys Gly Cys Thr Ala Gly Cys
                325                 330                 335

Ala Ala Cys Thr Thr Gly Ala Cys Cys Thr Cys Gly Gly Thr Cys Cys
            340                 345                 350

Cys Ala Gly Thr Gly Cys Cys Cys Cys Ala Cys Ala Cys Cys Ala Cys
        355                 360                 365

Cys Gly Cys Ala Cys Thr Gly Thr Cys Gly Cys Thr Gly Cys Cys Cys
    370                 375                 380

Gly Cys Cys Thr Gly Cys Cys Cys Thr Gly Ala Gly Gly Ala Gly Thr
385                 390                 395                 400

Cys Cys Cys Cys Gly Cys Thr Gly Cys Thr Thr Gly Thr Gly Gly Gly
                405                 410                 415
```

-continued

Cys Cys Cys Cys Ala Thr Gly Cys Thr Gly Ala Thr Gly Ala Gly
                420                 425                 430

Thr Thr Thr Ala Ala Cys Ala Thr Gly Cys Cys Thr Gly Thr Gly Gly
            435                 440                 445

Ala Cys Cys Thr Gly Gly Ala Gly Cys Thr Cys Gly Thr Gly Gly Cys
450                 455                 460

Ala Ala Ala Gly Cys Ala Gly Ala Ala Cys Cys Ala Ala Ala Thr
465                 470                 475                 480

Gly Thr Gly Ala Ala Gly Ala Thr Gly Gly Cys Gly Gly Cys Cys
            485                 490                 495

Gly Cys Thr Ala Thr Gly Cys Cys Cys Cys Ala Gly Gly Gly Ala
            500                 505                 510

Cys Thr Gly Cys Gly Thr Cys Thr Cys Thr Cys Ala Cys
            515                 520                 525

Ala Ala Gly Gly Thr Gly Gly Cys Cys Thr Cys Ala Thr Cys Ala
530                 535                 540

Thr Thr Cys Cys Ala Thr Thr Cys Cys Gly Cys Ala Ala Cys Cys Gly
545                 550                 555                 560

Gly Cys Ala Gly Gly Ala Gly Cys Ala Cys Cys Thr Cys Ala Ala Gly
            565                 570                 575

Thr Ala Cys Thr Gly Gly Cys Thr Ala Thr Ala Thr Ala Thr Thr
            580                 585                 590

Thr Gly Cys Ala Cys Cys Cys Ala Gly Thr Cys Cys Thr Gly Cys Ala
595 600 605

Gly Cys Gly Cys Cys Ala Gly Cys Ala Gly Cys Thr Gly Gly Ala Cys
610 615 620

Thr Ala Thr Gly Gly Cys Ala Thr Cys Thr Ala Thr Gly Thr Thr Ala
625 630 635 640

Thr Cys Ala Ala Cys Cys Ala Gly Gly Cys Gly Gly Gly Ala Gly Ala
645 650 655

Cys Ala Cys Thr Ala Thr Ala Thr Thr Cys Ala Ala Thr Cys Gly Thr
660 665 670

Gly Cys Thr Ala Ala Gly Cys Thr Cys Cys Thr Cys Ala Ala Thr Gly
675 680 685

Thr Thr Gly Gly Cys Thr Thr Thr Cys Ala Ala Gly Ala Ala Gly Cys
690 695 700

Cys Thr Thr Gly Ala Ala Gly Gly Ala Cys Thr Ala Thr Gly Ala Cys
705 710 715 720

Thr Ala Cys Ala Cys Cys Thr Gly Cys Thr Thr Thr Gly Thr Gly Thr
725 730 735

Thr Thr Ala Gly Thr Gly Ala Cys Gly Thr Gly Gly Ala Cys Cys Thr
740 745 750

Cys Ala Thr Thr Cys Cys Ala Ala Thr Gly Ala Ala Thr Gly Ala Thr
755 760 765

Cys Ala Thr Ala Ala Thr Gly Cys Gly Thr Ala Cys Ala Gly Gly Thr
770 775 780

Gly Thr Thr Thr Thr Thr Cys Ala Cys Ala Gly Cys Cys Ala Cys Gly
785 790 795 800

Gly Cys Ala Cys Ala Thr Thr Thr Cys Cys Gly Thr Thr Gly Cys Ala
805 810 815

Ala Thr Gly Gly Ala Thr Ala Ala Gly Thr Thr Thr Gly Gly Ala Thr
820 825 830

Thr Cys Ala Gly Cys Cys Thr Ala Cys Cys Thr Thr Ala Thr Gly Thr

```
            835             840             845
Thr Cys Ala Gly Thr Ala Thr Thr Thr Gly Gly Ala Gly Gly Thr
    850                 855                 860
Gly Thr Cys Thr Cys Thr Gly Cys Thr Thr Cys Ala Ala Gly Thr Ala
865                 870                 875                 880
Ala Ala Cys Ala Ala Cys Ala Gly Thr Thr Cys Thr Ala Ala Cys
                885                 890                 895
Cys Ala Thr Cys Ala Ala Thr Gly Ala Thr Thr Thr Cys Cys Thr
            900                 905                 910
Ala Ala Thr Ala Ala Thr Thr Ala Thr Gly Gly Gly Gly Cys Thr
            915                 920                 925
Gly Gly Gly Gly Ala Gly Gly Ala Gly Ala Ala Gly Ala Thr Gly Ala
    930                 935                 940
Thr Gly Ala Cys Ala Thr Thr Thr Thr Ala Cys Ala Gly Ala
945                 950                 955                 960
Thr Thr Ala Gly Thr Thr Thr Thr Thr Ala Gly Ala Gly Gly Cys Ala
        965                 970                 975
Thr Gly Thr Cys Thr Ala Thr Ala Thr Cys Thr Cys Gly Cys Cys Cys
                980                 985                 990
Ala Ala Ala Thr Gly Cys Thr Gly Thr Gly Gly Thr Cys Gly Gly Gly
        995                 1000                1005
Ala Cys Gly Thr Gly Thr Cys Gly Cys Ala Thr Gly Ala Thr Cys Cys
    1010                1015                1020
Gly Cys Cys Ala Cys Thr Cys Ala Ala Gly Ala Gly Ala Cys Ala Ala
1025                1030                1035                1040
Gly Ala Ala Ala Ala Thr Gly Ala Ala Cys Cys Ala Ala Thr
        1045                1050                1055
Cys Cys Thr Cys Ala Gly Ala Gly Gly Thr Thr Thr Gly Ala Cys Cys
            1060                1065                1070
Gly Ala Ala Thr Thr Gly Cys Ala Cys Ala Cys Ala Ala Ala
        1075                1080                1085
Gly Gly Ala Gly Ala Cys Ala Ala Thr Gly Cys Thr Cys Thr Cys Thr
        1090                1095                1100
Gly Ala Thr Gly Gly Thr Thr Thr Gly Ala Ala Cys Thr Cys Ala Cys
1105                1110                1115                1120
Thr Cys Ala Cys Cys Thr Ala Cys Cys Ala Gly Gly Thr Gly Cys Thr
                1125                1130                1135
Gly Gly Ala Thr Gly Thr Ala Cys Ala Gly Ala Gly Ala Thr Ala Cys
            1140                1145                1150
Cys Cys Ala Thr Thr Gly Thr Ala Thr Ala Cys Cys Ala Ala Ala
            1155                1160                1165
Thr Cys Ala Cys Ala Gly Thr Gly Gly Ala Cys Ala Thr Cys Gly Gly
    1170                1175                1180
Gly Ala Cys Ala Cys Cys Gly Ala Gly Cys Thr Ala Gly
1185                1190                1195
```

<210> SEQ ID NO 12
<211> LENGTH: 36
<212> TYPE: DNA
<213> ORGANISM: Artificial Sequence
<220> FEATURE:
<223> OTHER INFORMATION: A synthetic primer

<400> SEQUENCE: 12
atcgggaaga cgcgtcacat ccgccactcg agagac                                 36

```
<210> SEQ ID NO 13
<211> LENGTH: 36
<212> TYPE: DNA
<213> ORGANISM: Artificial Sequence
<220> FEATURE:
<223> OTHER INFORMATION: A synthetic primer

<400> SEQUENCE: 13
atcgggaaga cgcgtgagat ccgccactcg agagac                             36
```